US008105602B2

(12) United States Patent
Parry et al.

(10) Patent No.: US 8,105,602 B2
(45) Date of Patent: Jan. 31, 2012

(54) UROKINASE-TYPE PLASMINOGEN ACTIVATOR RECEPTOR EPITOPE, MONOCLONAL ANTIBODIES DERIVED THEREFROM AND METHODS OF USE THEREOF

(75) Inventors: Graham Parry, San Mateo, CA (US); Andrew P. Mazar, San Diego, CA (US)

(73) Assignee: Tactic Pharma, LLC, Evanston, IL (US)

( * ) Notice: Subject to any disclaimer, the term of this patent is extended or adjusted under 35 U.S.C. 154(b) by 417 days.

(21) Appl. No.: 12/001,037

(22) Filed: Dec. 7, 2007

(65) Prior Publication Data

US 2008/0199476 A1 Aug. 21, 2008

Related U.S. Application Data

(60) Provisional application No. 60/873,627, filed on Dec. 8, 2006, provisional application No. 60/930,034, filed on May 11, 2007.

(51) Int. Cl.
*A61K 39/00* (2006.01)
(52) U.S. Cl. .................... 424/185.1; 530/300; 530/326; 435/70.21
(58) Field of Classification Search ........................ None
See application file for complete search history.

(56) References Cited

U.S. PATENT DOCUMENTS

| 4,946,778 | A | 8/1990 | Ladner et al. |
|---|---|---|---|
| 5,057,313 | A | 10/1991 | Shih et al. |
| 5,443,816 | A | 8/1995 | Zamora et al. |
| 5,519,120 | A | 5/1996 | Dano et al. |
| 5,521,290 | A | 5/1996 | Sivam et al. |
| 5,532,132 | A | 7/1996 | Wang et al. |
| 5,561,220 | A | 10/1996 | Dean et al. |
| 5,567,408 | A | 10/1996 | Zamora |
| 5,618,513 | A | 4/1997 | Srinivasan |
| 5,627,286 | A | 5/1997 | Ramalingam et al. |
| 5,869,238 | A | 2/1999 | Morrison |
| 5,891,664 | A | 4/1999 | Dano et al. |
| 6,025,142 | A | 2/2000 | Pessara et al. |
| 6,248,712 | B1 | 6/2001 | Dano et al. |
| 7,488,813 | B2 * | 2/2009 | Pollock et al. ............... 536/23.1 |
| 2003/0219837 | A1 | 11/2003 | Cress et al. |
| 2004/0115190 | A1 | 6/2004 | Blasi et al. |
| 2005/0232924 | A1 | 10/2005 | Mazar et al. |
| 2005/0233397 | A1 | 10/2005 | Atassi et al. |
| 2009/0180952 | A1 | 7/2009 | Parry et al. |

FOREIGN PATENT DOCUMENTS

| EP | 0 308 716 A2 | 3/1989 |
|---|---|---|
| EP | 0 354 408 A1 | 2/1990 |
| EP | 1 691 664 A2 | 6/2005 |
| EP | 1 765 397 | 12/2005 |
| WO | WO 86/01533 A1 | 3/1986 |
| WO | WO 92/07083 | 4/1992 |
| WO | WO 93/09808 | 5/1993 |
| WO | WO 93/24141 A1 | 12/1993 |
| WO | WO 99/48509 | 9/1999 |
| WO | WO 00/62071 | 10/2000 |
| WO | WO 02/058714 A2 | 8/2002 |
| WO | WO 03/057831 A2 | 7/2003 |
| WO | WO 03/082072 A2 | 10/2003 |
| WO | WO 2004/003183 A1 | 1/2004 |
| WO | WO 2004/099780 | 11/2004 |
| WO | WO 2005/048822 A2 | 6/2005 |
| WO | WO 2005/116077 A2 | 12/2005 |
| WO | WO 2006090389 A2 * | 8/2006 |
| WO | WO 2008/073312 A2 | 6/2008 |

OTHER PUBLICATIONS

Colman, P.M., Research in Immunology, 1994, 145:33-36.*
Mandi et al., J Biol Chem. Apr. 16, 2004;279(16):16621-8. Epub Feb. 5, 2004.*
Sidenius et al., FEBS Lett. Jun. 9, 2000;475(1):52-6.*
Resnati et al., J Immunol Methods. Jan. 20, 2006;308(1-2):192-202. Epub Dec. 19, 2005.*
Duval-Jobe et al., J Interferon Cytokine Res. Jun. 1995;15(6):557-67.*
Definition of "purification", downloaded from medical-dictionary.thefreedictionary.com/purify, on Jan. 26, 2011.*
Kenny et al., 2007, Treatment with an Anti-Urokinase Plasminogen Activator Receptor (ATN 658) Antibody Inhibits Ovarian Cancer Metastasis, EORTC-NCI-AACR International Conference, Molecular Targets and Cancer Therapeutics, San Francisco, CA (Oct. 22-26, 2007).
Pedersen et al., 1994. Prognostic impact of urokinase, urokinase receptor, and type 1 plasminogen activator inhibitor in squamous and large cell lung cancer tissue, Cancer Res., 54(17):4671-4675.
Andreasen et al., 1997, The Urokinase-type Plasminogen Activator System in Cancer Metastasis: A Review, Int J Cancer, 72: 1-22.
Henic et al., Nov. 2, 2005, EGF-Stimulated Migration in Ovarian Cancer Cells is Associated with Decreased Internalization, Increased Surface Expression, and Increased Shedding of the Urokinase Plasminogen Activator Receptor, Gyn Onc., 101: 28-39.
Behrendt et al., 1995, "The structure and function of the urokinase receptor, a membrane protein governing plasminogen activation on the cell surface." Biol Chem Hoppe-Seyeler. 376:269-279.
Bird et al., 1988, "Single-chain antigen-binding proteins." Science 242:423-426.
Blood et al., 1990, "Tumor interactions with the vasculature: angiogenesis and tumor metastasis" Biochim Biophys Acta, 1032:89-118.
Boisson-Vidal et al., 2007, "Neoangiogenesis induced by progenitor endothelial cells: effect of fucoidan from marine algae," Cardiovascular & Hematological Agents in Medicinal Chemistry. 5: 67-77.
Brinkman et al., 1991, "B3(Fv)-PE38KDEL, a single-chain immunotoxin that causes complete regression of a human carcinoma in mice." Proc Natl Acad Sci USA, 88:8616-8620.
Xing et al., 1996, "Overexpression of urokinase receptor in breast cancer cells results in increased tumor invasion, growth and metastasis." Int J Cancer., 67:423-429.
Chambers et al., 1995, "Macrophage colony-stimulating factor mediates invasion of ovarian cancer cells through urokinase." Cancer Res., 55:1578-1585.

(Continued)

Primary Examiner — Michael Szperka
(74) Attorney, Agent, or Firm — Browdy and Neimark, PLLC

(57) ABSTRACT

The present invention relates to antibodies, and antigen-binding fragments thereof, specific for urokinase-type plasminogen activator receptor (uPAR) and uses thereof for the treatment or prevention of cancer. In particular, the antibodies of the invention are specific for a particular epitope on uPAR. These antibodies interfere with uPAR signaling. Such antibodies are used in diagnostic and therapeutic methods, particularly against cancer.

23 Claims, 9 Drawing Sheets

OTHER PUBLICATIONS

Figure 2:
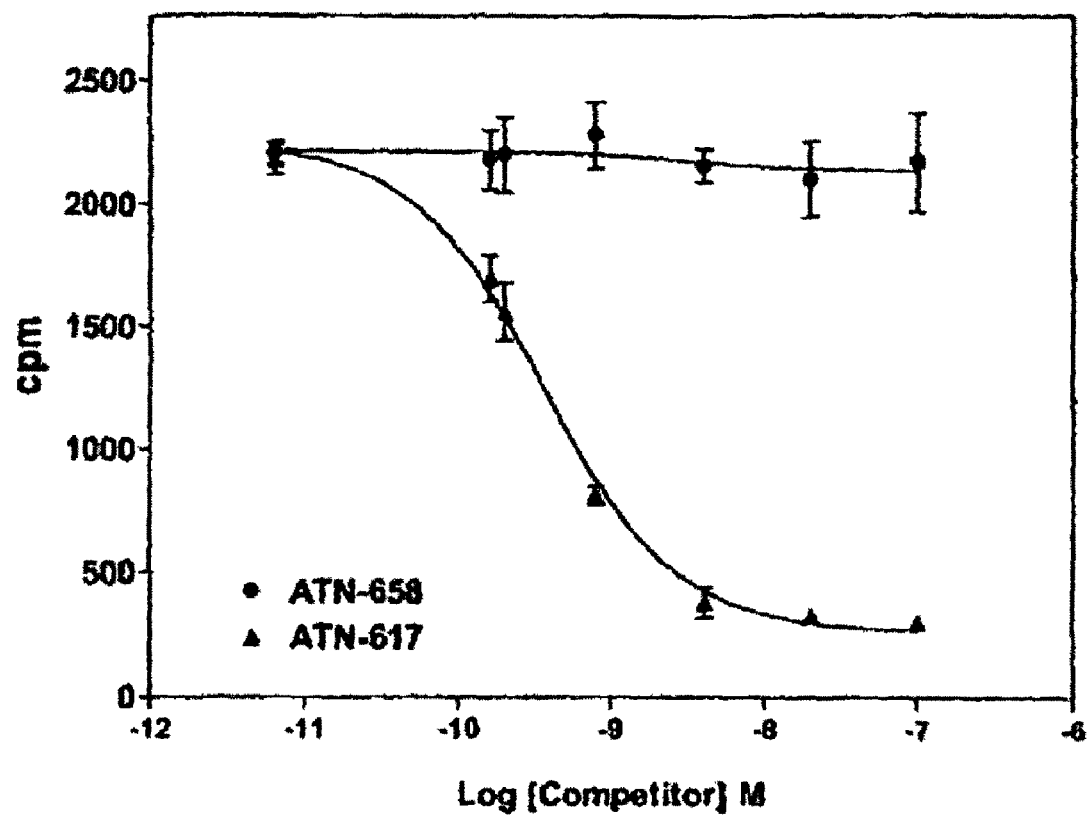

Christiansen, et al., 1996, "Immunohistochemical Localization of Urokinase-type Plasminogen Activator, type-1 Plasminogen-activator Inhibitor, Urokinase Receptor and α2-Macroglobulin Receptor in human breast carcinomas," Int J Cancer, 66: 441-452.

Conese, et al., 1995, "α-2 Macroglobulin Receptor/Ldl Receptor-related Protein (Lrp)-dependent Internalization of the Urokinase Receptor," J Cell Biol., 131: 1609-1622.

Corti et al., 1989, "Epitope mapping of the anti-urokinase monoclonal antibody 5B4 by isolated domains of urokinase," Thrombosis and Haemostasis, 62(3): 934-939.

Damle et al., 2000, "Influence of immunogenicity on the pharmacokinetics of BMS-191352 a Pseudomonas exotoxin immunoconjugate, in rats and dogs." J Pharm Pharmacol. 52:671-678.

Dano et al., 1985, "Plasminogen activators, tissue degradation, and cancer." Adv Cancer Res. 44:139-266.

Eaton, D.L. et al., 1984, "Purification of Human Fibroblast Urokinase Proenzyme and Analysis of Its Regulation by Proteases and Protease Nexin," J Biol Chem., 259: 6241-6247.

Ehnman et al., 2009, "The uPA/UPAR system regulated the bioavailability of PDGF-DD: implications for tumor growth," Oncogene, 28(4):534-44.

Ellis et al., 1989, "Plasminogen activation initiated by single-chain urokinase-type plasminogen activator. Potentiation by U937 monocytes." J Biol Chem., 264:2185-88.

Ellis, et al., 1993, "Potentiation of Plasminogen Activation by an Anti-urokinase Monoclonal Antibody Due to Ternary Complex Formation," J Biol Chem., 268(7): 4806-4813.

Fabbrini, et al.,1997, "The amino-terminal fragment of human urokinase directs a recombinant chimeric toxin to target cells: internalization is toxin mediated," The FASEB Journal, 11: 1169-1176.

Fong et al., 2002. "Random peptide bacteriophage display as a probe for urokinase receptor ligands." Biol Chem., 383(1):149-58.

Frankel et al, 2002, "Immunotoxin therapy of hematologic malignancies." Sem Oncol., 30:545-557.

Garcia-Touchard et al., 2005, "Extracellular proteases in artherosclerosis and restenosis," Arterioscler, Thromb Vasc Biol., 25:1119-1127.

Garnett, 2001, "Targeted drug conjugates: principles and progress." Adv. Drug. Delivery 53:171-216.

Ghamande et al., 2008, "A phase 2, randomized, double-blind, placebo-controlled trail of clinical activity and safety of subcutaneous Å6 in women with asymptomatic CA125 progression after first-line chemotherapy of epithelial ovarian cancer," Gynecologic Oncology, 111:89-94.

Grondahl-Hansen et al., 1987, "Immunohistochemical localization of urokinase- and tissue-type plasminogen activators in psoriatic skin," J Invest Dermatol., 88(1): 28-32.

Haggerty et al., 1999. "BR96 sFv-PE40 immunotoxin: Nonclinical Safety Assessment." Toxicol Pathol., 27(1):87-94.

Heiss et al., 1995, "Individual development and uPA-receptor expression of disseminated tumour cells in bone marrow: a reference to early systemic disease in solid cancer." Nature Med., 1:1035-1039.

Herszenyi et al., 1997, "Impaired fibrinolysis and increased protease levels in gastric and duodenal mucosa of patients with active duodenal ulcer," Am J of Gastroenterology, 92(5):843-847.

Hofmann et al., 1996, "Clinical relevance of urokinase plasminogen activator, its receptor, and its inhibitor in patients with renal cell carcinoma." Cancer, 78:487-492.

Hsieh et al., 2007. "Upregulation of urokinase-type plasminogen activator and inhibitor and gelatinase expression via 3 mitogen activated protein kinases and P13K pathways during the early development of osteoarthritis," J Rheumatol., 34:785-793.

Huston et al., 1988, "Protein engineering of antibody binding sites: Recovery of specific activity in an anti-digoxin single-chain Fv analogue produced in *Escherichia coli*." Proc Natl Acad Sci USA, 85:5879-5883.

Janeway, C.A., Travers, P., Walport, M. Shlomchick, M.J., 2001, Immunobiology, Part II, § 3-8.

Jessani, M. et al., 2002, "Enzyme activity profiles of the secreted and membrane proteome that depict cancer cell invasiveness," Proc Natl Acad Sci USA, 99: 10335-10340.

Jin et al., 2003, "Urokinase, a constitutive component of the inflamed synovial fluid, induces arthritis," Arthritis Res Ther., 5:R9-R17.

Kleinman et al., 1986, "Basement Membrane Complexes with Biological Activity" Biochem., 25:312-318.

Koh et al. 2004, "Inhibition of choroidal neovascularization in rats by the urokinase-derived peptide A6," Invest Opthamol Vis Sci., 45: 635-640.

Kreitman, R.J., 2001, "Chimeric fusion proteins—*Pseudomonas* exotoxin-based." Curr Opin Invest Drugs, 2:1282-1293.

Kreitman, R.J., 2003, "Recombinant toxins for the treatment of cancer." Curr Opin Mol Therapeutics, 5:44-51.

Kreitman, R.J., 2001, "Toxin-Labeled Monoclonal Antibodies," Curr Pharm Biotechnol., 2(4), 313-325.

Leake et al., 2003, "Expression of urokinase-type plasminogen activator and its receptor in keloids." Arch Otolaryngol Head Neck Surg., 129:1334-1338.

LeGat et al., 2003, "In vivo adenovirus-mediated delivery of a uPA/uPAR antagonist reduces retinal neovascularization in a mouse model of retinopathy," Gene Therapy, 10(25):2098-2103.

Lembessis et al., 2003, "Urokinase-type plasminogen activator and insulin-like growth factor-binding protein 3 mRNA expression in endometriotic lesions and ectopic endometrium," Ann NY Acad Sci., 997:223-228.

Lewis et al.. 1995, "Cytokine regulation of angiogenesis in breast cancer: the role of tumor-associated macrophages" J Leukoc Biol., 57:747-751.

Li et al., 2003, "Sequences within domain II of the urokinase receptor critical for differential ligand recognition." J Biol Chem., 278(32):29925-32.

List et al., 1999, "Different mechanisms are involved in the antibody mediated inhibition of ligand binding to the urokinase receptor: a study based on biosensor technology" J Immunol Methods, 222(1-2):125-33.

Luikart et al., 2002, "Urokinase is required for the formation of mactinin, an α-actinin fragment that promotes monocyte/macrophage maturation," Biochim Biophysica Acta, 1591: 99-107.

Lund et al., 1991, "Urokinase receptor mRNA level and gene transcription are strongly and rapidly increased by phorbol myristate acetate in human monocyte-like U937 cells." J Biol Chem. 266:5177-5181.

Yoshida et al., 1996, "Modulation of the receptor for urokinase-type plasminogen activator in macrophage-like U937 cells by inflammatory mediators" Inflammation, 20:319-326.

Mandriota et al., 1995, "Vascular endothelial growth factor increases urokinase receptor expression in vascular endothelial cells." J Biol Chem., 270: 9709-9716.

Mazar et al., 1992, "Domain analysis of urokinase plasminogen activator (u-PA) preparation and characterization of intact A-chain molecules," Fibrinolysis, Suppl. 1: 49-55.

McCullough, Kenneth C. & Spier, R.E., 1990 Monoclonal Antibodies in Biology and Biotechnology: Theoretical and Practical Aspects, § 1.3: 5-21.

Meyer et al., 2003, "Recent advances in antibody-drug conjugates for cancer therapy" Annu Rep Med Chem., 38:229-237.

Mignatti et al., 1991, "Expression of the urokinase receptor in vascular endothelial cells is stimulated by basic fibroblast growth factor" J Cell Biol., 113:1193-1201.

Min et al., 1996, "Urokinase receptor antagonists inhibit angiogenesis and primary tumor growth in syngeneic mice", Cancer Res., 56:2428-2433.

Mukhina, et al., 2000, "The Chemotactic Action of Urokinase on Smooth Muscle Cells is Dependent on its Kringle Domain," J Biol Chem., 275: 16450-16458.

Murdoch et al., 2002, "Roles of the ovarian surface epithelium in ovulation and carcinogenesis," Reproduction, 123:743-750.

Nicholl et al., 2006, "Plasminogen activator system and vascular disease," Current Vascular Pharmacology, 4: 101-116.

Nolli et al., 1986, "A monoclonal antibody that recognizes the receptor binding region of human urokinase plasminogen activator," Thrombosis and Haemostasis, 56(2), pp. 214-218.

Nykjaer et al., 1994, "Regions involved in binding of urokinase-type-1 inhibitor complex and pro-urokinase to the endocytic α₂-macroglobulin receptor/low density lipoprotein receptor-related protein," J Biol Chem., 269(1): 25668-25676.
O et al., 2008, "Integrin αvβ3 is not significantly implicated in the anti-migratory effect of anti-angiogenic urokinase kringle domain," Oncology Reports, 20:631-636.
Odedra et al., 1991. "Low molecular weight angiogenesis factors." Pharmac Ther., 49:111-124.
Ossowski, et al., 1983, "Antibodies to Plasminogen Activator Inhibit Human Tumor Metastasis," Cell, 5: 611-619.
Panchagnula et al., 1997, "Monoclonal antibodies in drug targeting," Journal of Clinical Pharmacy and Therapeutics, 22:7-19.
Parfyonova et al., 2004, "Contrasting effects of urokinase and tissue-type plasminogen activators on neointima formation and vessel remodelling after arterial injury," J Vasc Res., 41:268-276.
Parish et al., 1992, "A basement-membrane permeability assay which correlates with the metastatic potential of tumour cells." Int J Cancer, 52:378-383.
Passaniti et al., 1992, "A simple, quantitative method for assessing angiogenesis and antiangiogenic agents using reconstituted basement membrane, heparin, and fibroblast growth factor." Lab Invest. 67:519-528.
Pepper et al., 1993, "Upregulation of urokinase receptor expression in migrating endothelial cells," J Cell Biol., 122: 673-684.
Petersen, et al., 2001, "Localization of epitopes for monoclonal antibodies to urokinase-type plasminogen activator," Eur J Biochem., 268: 4430-4439.
Pirker et al., 1985, "Characterization or immunotoxins active against ovarian cancer cell," J Clin Invest., 76: 1261-1267.
Pöllänen et al., 1987, "Distant localizations of urokinase-type plasminogen activator and its type 1 inhibitor under cultured human fibroblasts and sarcoma cells," J Cell Biol., 104: 1085-1096.
Prager et al., 2009, "Urokinase (uPA) mediates endothelial cell survival via induction of the x-linked inhibitor of apoptosis protein (XIAP)" Blood, 113(6): 1383-90.
Zorio et al., 2008, "Fibrinolysis: the key to new pathogenetic mechanisms," Curr Med Chem., 15:923-929.
Rabbani et al., 1995, "Prevention of prostate-cancer metastasis in vivo by a novel synthetic inhihitor of urokinase-type plasminogen activator (uPA)" Int J Cancer, 63:840-845.
Schnaper et al., 1995, "Plasminogen activators augment endothelial cell organization in vitro by two distinct pathways." J Cell Physiol. 165:107-118.
Sood et al., 1999, "Topical amiloride accelerates healing and delays neovascularization in mechanically produced corneal ulcers in rabbits," Methods Find Exp Clin Pharmacol., 21(7):491-497.
Sotiriadis et al., 2007, "Fibrinolytic defects and recurrent miscarriage—A systematic review and meta-analysis" Obstetrics & Gynecology, 109(5):1146-1155.
Stephens et al., 1992, "Heparin binding to the urokinase kringle domain," Biochemistry, 31: 7572-7579.
Stoppelli et al., 1985, "Differentiation-enhanced binding of the amino-terminal fragment of human urokinase plasminogen activator to a specific receptor on U937 monocytes," Proc Natl Acad Sci USA, 82: 4939-4943.
Strauss et al., 1999, "Plasma urokinase antigen and plasminogen activator inhibitor-1 antigen levels predict angiographic coronary restenosis," Circulation, 100(15): 1616-1622.
Thewes et al., 2000, "The urokinase plasminogen activator system in angiosarcoma, Kaposi's sarcoma, granuloma pyrogenicum, and angioma: an immunohistochemical study," Intl J of Dermatology, 39:188-191.
Trail, et al., 2002, "Monoclonal antibody drug immunoconjugates for targeted treatment of cancer." Cancer Immunol Immunother., 52:328-337.
Usher et al., 2005, "Expression of urokinase plasminogen activator, its receptor and type-1 inhibitor in malignant and benign prostate tissue," Int J Cancer, 113:870-880.
Uszynski et al, 2004, "Urokinase plasminogen activator (uPA) and its receptor (uPAR) in gestational tissues measurements and clinical implications," Eur J Obstet Gynecol Reprod Biol., 114: 54-58.
Vocca et al., 2009, "Inhibition or migration of carcinoma cells by urokinase-derived antagonists of αvβ5 integrin activation." Int J Cancer, 124:316-325.

Ward et al., 1988, "Response of Complement and Neutrophils to Hydrophilized Synthetic Membranes," ASAIO Trans. 34:334-337.
Webber et al., 1995. "Urokinase-mediated Extracellular Matrix Degradation by Human Prostatic Carcinoma Cells and Its Inhibition hy Retinoic Acid," Clin Can Res., 1: 755-761.
Weissman et al., 1980, "Only high-affinity receptors for interleukin 2 mediate internalization of ligand," Proc. Natl Acad Sci USA, 83: 1463-1466.
Woo, 2002, "In vitro cytotoxicity mediated by anti-urokinase type plasminogen activator (uPA) immunoliposome," Abstract #4756, Experimental/Molecular Therapeutics, Proceedings of the American Association for Cancer Research Annual Meeting, 43: 960.
European Search Report, dated Apr. 1, 2008 of EP 1 691 664, published Jun. 2, 2005.
European Search Report, dated Apr. 9, 2009 of EP 1 765 397, published Dec. 8, 2005.
Written Opinion of the International Searching Authority, dated Nov. 1, 2005 of PCT/US2005/18322, filed May 25, 2005.
International Search Report, dated Nov. 1, 2005 of PCT/US2005/018322, filed May 25, 2005.
Written Opinion of the International Searching Authority, dated Jul. 31, 2008 of PCT/US2007/25105, filed Dec. 7, 2007.
International Preliminary Report on Patentability, dated Jun. 10, 2009 of PCT/US2007/025105, filed Dec. 7, 2007.
International Search Report. dated Aug. 31, 2006 of PCT/US2004/038617, filed Nov. 18, 2004.
International Preliminary Report on Patentability, Nov. 7, 2006 of PCT/US2004/038617, filed Nov. 18, 2004.
Written Opinion of the International Searching Authority, dated Aug. 31, 2006 of PCT/US2004/38617, filed Nov. 18, 2004.
Search Report, dated Mar. 20, 2008, for Singapore Application No. 200603335-1, filed Nov. 18, 2004.
Office Action, dated Oct. 3, 2007, for U.S. Appl. No. 10/993,007, filed Nov. 18, 2004.
Office Action, dated Nov. 2, 2007, for U.S. Appl. No. 10/993,007, filed Nov. 18, 2004.
Office Action, dated Jun. 19, 2008, for U.S. Appl. No. 10/993,007, filed Nov. 18, 2004.
Office Action, dated Feb. 20. 2009, for U.S. Appl. No. 10/993,007, filed Nov. 18, 2004.
Responsive to Communication, dated Oct. 14, 2009, for U.S. Appl. No. 11/597,689, filed May 25, 2005.
Aguirre Ghiso et al., 1999, "Tumor dormancy induced by downregulation of urokinase receptor in human carcinoma involves integrin and MAPK signaling," J Cell Biol., vol. 147:89-103.
Ahmed et al., 2005, "Ascites induces modulation of α6 β1 integrin and urokinase plasminogen activator receptor expression and associated functions in ovarian carcinoma," Br J. Cancer, vol. 92:1475-1485.
Andolfo et al., 2002, "Metalloproteases cleave the urokinase-type plasminogen activator receptor in the D1-D2 linker region and expose epitopes not present in the intact soluble receptor," Thromb Haemost, vol. 88:298-306.
Artym et al., 2002, "Molecular proximity of seprase and the urokinase-type plasminogen activator receptor on malignant melanoma cell membranes: dependence on β1 integrins and the cytoskeleton," Carcinogenesis, vol. 23:1593-1601.
Aung et al., 2005, "Bioactivation of latent transforming growth factor β1 by *Mycobacterium tuberculosis* in human mononuclear phagocytes," Scand J Immunol., vol. 61:558-565.
Baerga-Ortiz et al., 2002, "Epitope mapping of a monoclonal antibody against human thrombin by H/D-exchange mass spectrometry reveals selection of a diverse sequence in a highly conserved protein," Protein Sci., vol. 11(6):1300-8.
Bass et al., 2005, "Regulation of urokinase receptor proteolytic function by the tetraspanin CD82," J Biol Chem., vol. 280:14811-14818.
Bastholm et al., 1999, "Increased vascular endothelial growth factor in tumor cells and increased production of the receptor for urokinase plasminogen activator in endothelial cells are associated with lymph node metastasis in human breast cancer," Appl Immunohistochem Mol Morphol., vol. 7:39-47.

Bauer et al., 2005, "Insulinlike growth factor-I-mediated migration and invasion of human colon carcinoma cells requires activation of c-Met and urokinase plasminogen activator receptor," Ann Surg., vol. 241:748-758.

Bauer et al., 2005, "Targeting of urokinase plasminogen activator receptor in human pancreatic carcinoma cells inhibits c-Met- and insulin-like growth factor-I receptor-mediated migration and invasion and orthotopic tumor growth in mice," Cancer Res., vol. 65:7775-7781.

Bdeir et al., 2000, "A region in domain II of the urokinase receptor required for urokinase binding," J Biol Chem., vol. 275:28532-28538.

Behzadian et al., 2003, "VEGF-induced paracellular permeability in cultured endothelial cells involves urokinase and its receptor," FASEB J., vol. 17:U350-U371.

Bhat et al., 1999, "Urokinase-type plasminogen activator induces tyrosine phosphorylation of a 78-kDa protein in H-157 cells," Amer J Physiol., vol. 277:L301-L309.

Bianchi et al., 1996, "Integrin-dependent induction of functional urokinase receptors in primary T lymphocytes," J Clin Invest., vol. 98:1133-1141.

Bianchini et al., 2006, "Cytokine-dependent invasiveness in B16 murine melanoma cells: role of uPA system and MMP-9," Oncology Reports, vol. 15:709-714.

Brodsky et al., 2002, "Plasminogen activator inhibitor-1 promotes formation of endothelial microparticles with procoagulant potentential," Circulation, vol. 106:2372-2378.

Buo et al., 1995, "Antigen levels of urokinase plasminogen activator and its receptor at the tumor-host interface of colorectal adenocarcinomas are related to tumor aggressiveness," Human Pathol., vol. 26:1133-1138.

Busso et al., 1994, "Induction of cell migration by pro-urokinase binding to its receptor: possible mechanism for signal transduction in human epithelial cells," J Cell Biol., vol. 126:259-270.

Cao et al., 2004, "Urokinase-type plasminogen activator receptor is involved in mediating the apoptotic effect of cleaved high molecular weight kininogen in human endothelial cells," Circ Res., vol. 94:1227-1234.

Carriero et al., 1994, "Tissue distribution of soluble and receptor-bound urokinase in human breast cancer using a panel of monoclonal antibodies," Cancer Res., vol. 54:5445:5454.

Carriero et al., 1997, "Vitronectin binding to urokinase receptor in human breast cancer," Clin Cancer Res., vol. 3:1299-1308.

Cavallaro et al., 1998, "FGF-2 stimulates migration of Kaposi's sarcoma-like vascular cells by HGF-dependent relocalization of the urokinase receptor," FASEB J., vol. 12:1027-1034.

Chang et al., 1998, "Urokinase receptor-dependent upregulation of smooth muscle cell adhesion to vitronectin by urokinase," Arterioscler Thromb Vasc Biol., vol. 18:1855-1860.

Chavakis et al., 1999, "Molecular mechanisms of zinc-dependent leukocyte adhesion involving the urokinase receptor and β2-integrins," Blood, vol. 93:2976-2983.

Chucholowski, 1992, "Flow cytofluorometric analysis of the urokinase receptor (uPAR) on tumor cells by fluorescent uPA-ligand or monoclonal antibody #3936," Fibrinolysis, vol. 6:95-102.

Colman et al., 1997, "Binding of high molecular weight kininogen to human endothelial cells is mediated via a site within domains 2 and 3 of the urokinase receptor," J Clin. Invest., vol. 100:1481-1487.

Conese et al., 1994, "Protease nexin-1-urokinase complexes are internalized and degraded through a mechanism that requires both urokinase receptor and α2-macroglobulin receptor," J Biol Chem., vol. 269:17886-17892.

D'Alessio 2004, "Antisense oligodeoxynucleotides for urokinase-plasminogen activator receptor have anti-invasive and anti-proliferative effects in vitro and inhibit spontaneous metastases of human melanoma in mice," Int'l J Cancer, vol. 110:125-133.

Dano et al., 1994, "The urokinase receptor: Protein structure and role in plasminogen activation and cancer invasion," Fibrinolysis, vol. 8:189-203.

De Witte et al., 1997, "ELISA for complexes between urokinase-type plasminogen activator and its receptor in lung cancer tissue extracts," Int J Cancer, vol. 72:416-423.

De Witte et al., 1998, "Complexes between urokinase-type plasminogen activator and its receptor in blood as determined by enzyme-linked immunosorbent assay," Intl J Cancer, vol. 77:236-242.

De Witte et al., 1999, "Prognostic impact of urokinase-type plasminogen activator (uPA) and its inhibitor (PAI-1) in cytosols and pellet extracts derived from 892 breast cancer patients," Br J Cancer, vol. 79:1190-8.

Degryse et al., 2001, "Urokinase/urokinase receptor and vitronectin/α(v) β(3) integrin induce chemotaxis and cytoskeleton reorganization through different signaling pathways," Oncogene, vol. 20:2032-2043.

Del Rosso et al., 2005, "Deflazacort modulates the fibrinolytic pattern and reduces uPA-dependent chemioinvasion and proliferation in rheumatoid arthritis synoviocytes," Rheumatology, vol. 44:1255-1262.

Del Vecchio et al., 1993, "Human urokinase receptor concentration in malignant and benign breast tumors by in vitro quantitative autoradiography: comparison with urokinase levels," Cancer Res., vol. 53:3198-3206.

Ellis et al., 1997, "Vascular smooth muscle cells potentiate plasmin generation by both urokinase and tissue plasminogen activator-dependent mechanisms: evidence for a specific tissue-type plasminogen activator receptor on these cells," Blood, vol. 90:2312-2322.

Farias-Eisner et al., 2000, "The urokinase plasminogen activator receptor (UPAR) is preferentially induced by nerve growth factor in PC12 pheochromocytoma cells and is required for NGF-driven differentiation," J Neurosci., vol. 20:230-239.

Fenton et al., 2004, "Pathophysiological effects of vascular endothelial growth factor receptor-2-blocking antibody plus fractionated radiotherapy on murine mammary tumors," Cancer Res., vol. 64:5712-5719.

Gärdsvoll et al., 2006, "Characterization of the functional epitope on the urokinase receptor," J Biol Chem., vol. 201(28):19260-19272.

Gärdsvoll et al., 1999, "Mapping part of the functional epitope for ligand binding on the receptor for urokinase-type plasminogen activator by site-directed mutagenesis," J Biol Chem., vol. 274(53):37995-38003.

Graham et al., 1999, "Hypoxia-mediated stimulation of carcinoma cell invasiveness via upregulation of urokinase receptor expression," Intl J Cancer, vol. 80:617-623.

Guilbert et al., 1999, "5-Oxo-6,8,11,14-eicosatetraenoic acid induces important eosinophil transmigration through basement membrane components: comparison of normal and asthmatic eosinophils," Amer J Resp Cell & Mol Biol., vol. 21:97-104.

Gyetko et al., 1995, "Function of the urokinase receptor (CD87) in neutrophil chemotaxis," J Leukocyte Biol., vol. 58:533-538.

Hamuro et al., 2006, "Hydrogen/deuterium-exchange (H/D-Ex) of PPARγ LBD in the presence of various modulators," Protein Sci., vol. 15(8):1883-92.

Herschman et al., 2000, "Searching for depolarization-induced genes that modulate synaptic plasticity and neurotrophin-induced genes that mediate neuronal differentiation," Neurochemical Res., vol. 25:591-602.

Holmes et al., 1985, "Cloning and expression of the gene for pro-urokinase in *Escherichia coli*," Nat. Biotechnol, vol. 3:923-929.

Hoyer-Hansen et al., 1992, "Urokinase plasminogen activator cleaves its cell surface receptor releasing the ligand-binding domain," J Biol Chem., vol. 267:18224-18229.

Hsu et al., 1995, "Prognostic role of urokinase-type plasminogen activator in human gliomas," Am J Pathol., vol. 147:114-23.

Huai et al., 2008, "Crystal structures of two human vitronectin, urokinase and urokinase receptor complexes", Nat. Struct. Mol. Biol., vol. 15(4):422-423.

International Search Report dated Aug. 8, 2008, issued in International Patent Application No. PCT/US07/25105.

Khan et al., 2006, "High-molecular-weight kininogen fragments stimulate the secretion of cytokines and chemokines through uPAR, Mac-1, and gC1qR in monocytes," Arterioscler Throm Vasc Biol., vol. 26:2260-2266.

Khatib et al., 2001, "Regulation of urokinase plasminogen activator/plasmin-mediated invasion of melanoma cells by the integrin vitronectin receptor αV β3," Intl. J Cancer, vol. 91:300-308.

Koshelnick et al., 1997, "Urokinase receptor is associated with the components of the JAK1/STAT1 signaling pathway and leads to activation of this pathway upon receptor clustering in the human kidney epithelial tumor cell line TCL-598," J Biol Chem., vol. 272:28563-28567.

Krishnamachary et al., 2003, "Regulation of colon carcinoma cell invasion by hypoxia-inducible factor 1," Cancer Res., vol. 63:1138-1143.

Lanza et al., 1998, "Expression and functional role of urokinase-type plasminogen activator receptor in normal and acute leukaemic cells," Br J Haematology, vol. 103:110-123.

Lee, 2004, "Involvement of MAPK pathway in hypoxia-induced up-regulation of urokinase plasminogen activator receptor in a human prostatic cancer cell line, PC3MLN4," Exper & Molec Med., vol. 36:57-64.

Lee et al., 2006, "Hepatocyte growth factor/c-met signaling in regulating urokinase plasminogen activator in human stomach cancer: A potential therapeutic target for human stomach cancer," Korean J of Internal Medicine, vol. 21:20-27.

Li et al., 1998, "Adenovirus-mediated delivery of a uPA/uPAR antagonist suppresses angiogenesis-dependent tumor growth and dissemination in mice," Gene Ther., vol. 5:1105-1113.

Low, M.G., 1989, "Glycosyl-phosphatidylinositol: a versatile anchor for cell surface proteins," FASEB, J. vol. 3:1600-1608.

Luther et al., 1997, "Epitope-mapped monoclonal antibodies as tools for functional and morphological analyses of the human urokinase receptor in tumor tissue," Amer J Pathol., vol. 150:1231-1244.

Ma et al., 2001, "Endogenously produced urokinase-type plasminogen activator is a major determinant of the basal level of activated ERK/MAP kinase and prevents apoptosis in MDA-MB-231 breast cancer cells," J Cell Sci., vol. 114:3387-3396.

Mahdi et al., 2001, "Expression and colocalization of cytokeratin 1 and urokinase plasminogen activator receptor on endothelial cells," Blood, vol. 97:2342-2350.

Mahdi et al., 2002, "Factor XII interacts with the multiprotein assembly of urokinase plasminogen activator receptor, gC1qR, and cytokeratin 1 on endothelial cell membranes," Blood, vol. 93:3585-3596.

Mahdi, 2003, "The relative priority of prekallikrein and factors XI/XIa assembly on cultured endothelial cells," J Biol Chem., vol. 278:43983-43990.

Manuppello 1996, "Epitope mapping of monoclonal antibodies (MA) to the human urokinase receptor (CD87)," Tissue Antigens, vol. 48:368 (Abstract AS-5-19).

May et al., 1998, "Urokinase receptor (CD87) regulates leukocyte recruitment via β2 integrins in vivo," J Exp Med., vol. 188:1029-1037.

Mazar et al., 1999, "The urokinase plasminogen activator system in cancer: implications for tumor angiogenesis and metastasis," Angiogenesis, vol. 3:15-32.

Mazar, AP, 2001, "The urokinase plasminogen activator receptor (uPAR) as a target for the diagnosis and therapy of cancer," Anti-Cancer Drugs, vol. 12:387-400.

Mizukami et al., 1994, "Immunologic detection of the cellular receptor for urokinase plasminogen activator," Clin Immunol and Immunopathol., vol. 71:96-104.

Mohanam et al., 1993, "Modulation of in vitro invasion of human glioblastoma cells by urokinase-type plasminogen activator receptor antibody," Cancer Res., vol. 53:4143-4147.

Møller et al., 1992, "Structural requirements for glycosyl-phosphatidylinositol-anchor attachment in the cellular receptor for urokinase plasminogen activator," Eur J. Biochem., vol. 208:493-500.

Monaghan 2004, "The receptor for urokinase-type plasminogen activator regulates fibronectin matrix assembly in human skin fibroblasts," J Biol Chem., vol. 279:1400-1407.

Monaghan-Benson et al., 2006, "Urokinase-type plasminogen activator receptor regulates a novel pathway of fibronectin matrix assembly requiring Src-dependent transactivation of epidermal growth factor receptor", J Biol Chem. vol. 281(14):9450-9459.

Montuori et al., 2002, "The cleavage of the urokinase receptor regulates its multiple functions," J Biol Chem., vol. 277:46932-46939.

Nakata et al., 1998, "Involvement of vascular endothelial growth factor and urokinase-type plasminogen activator receptor in microvessel invasion in human colorectal cancers," Int J Cancer, vol. 79:179-186.

Nisihara et al., 2001, "Humanization and epitope mapping of neutralizing anti-human Fas ligand monoclonal antibodies: structural insights into Fas/Fas ligand interaction," J Immunol., vol. 167(6):3266-3275.

Ohtani et al., 1995, "Expression of urokinase receptor in various stromal-cell populations in human colon cancer: immunoelectron microscopical analysis," Int J Cancer, vol. 62:691-696.

Pai et al., 2004, "Deoxycholic acid activates β-catenin signaling pathway and increases colon cell cancer growth and invasiveness," Mol Biol Cell., vol. 15:2156-2163.

Pass et al., 2003, "Generation of antibodies to the urokinase receptor (uPAR) by DNA immunization of uPAR knockout mice: membrane-bound uPAR is not required for an antibody response," Scand J Immunol., vol. 58:298-305.

Pedersen et al., 1993, "A ligand-free, soluble urokinase receptor is present in the ascitic fluid from patients with ovarian cancer," J Clin Invest., vol. 92:2160-2167.

Perkins et al., 1999, "Asbestos upregulates expression of the urokinase-type plasminogen activator receptor on mesothelial cells," Am J Respir Cell Mol Biol., vol. 21:637-646.

Piguet et al., 1999, "Urokinase receptor (uPAR, CD87) is a platelet receptor important for kinetics and TNF-induced endothelial adhesion in mice," Circulation, vol. 99:3315-3321.

Ploug et al., 1991, "Cellular receptor for urokinase plasminogen activator.," J Biol Chem, vol. 266:1926-1933.

Ploug et al., 2001, "Peptide-derived antagonists of the urokinase receptor. Affinity maturation by combinatorial chemistry, identification of functional epitopes, and inhibitory effect on cancer cell intravasation," Biochemistry, vol. 40:12157-12168.

Pyke, 1993, "Receptor for urokinase is present in tumor-associated macrophages in ductal breast carcinoma," Cancer Res., vol. 53:1911-1915.

Quax et al., 1998, "Binding of human urokinase-type plasminogen activator to its receptor—Residues involved in species specificity and binding," Arterioscler Thromb Vasc Biol., vol. 18:693-701.

Rabbani and Gladu, 2002, "Urokinase receptor antibody can reduce tumor volume and detect the presence of occult tumor metastases in vivo," Cancer Res, vol. 62:2390-2397.

Rofstad et al., 2002, "Hypoxia promotes lymph node metastasis in human melanoma xenografts by up-regulating the urokinase-type plasminogen activator receptor," Cancer Res., vol. 62:1847-1853.

Rofstad et al., 2004, "Increased metastatic dissemination in human melanoma xenografts after subcurative radiation treatment: radiation-induced increase in fraction of hypoxic cells and hypoxia-induced up-regulation of urokinase-type plasminogen activator receptor," Cancer Res., vol. 64:13-18.

Rofstad et al., 2005, "The tumor bed effect: increased metastatic dissemination from hypoxia-induced up-regulation of metastasis-promoting gene products," Cancer Res., vol. 65:2387-2396.

Roguska et al., 1994, "Humanization of murine monoclonal antibodies through variable domain resurfacing," Proc Natl. Acad. Sci. USA, vol. 91:969-973.

Roldan et al., 1990. "Cloning and expression of the receptor for human urokinase plasminogen activator, a central molecule in cell surface, plasmin dependent proteolysis." EMBO J. vol. 9(2):467-474.

Ronne et al., 1991, "Cell-induced potentiation of the plasminogen activation system is abolished by a monoclonal antibody that recognizes the NH2-terminal domain of the urokinase receptor," FEBS Lett., vol. 288:233-236.

Sawai et al., 2006, "Interleukin-1α enhances the aggressive behavior of pancreatic cancer cells by regulating the α6 β1-integrin and urokinase plasminogen activator receptor expression.," BMC Cell Biol. 7:8.

Sitrin et al., 1996, "The urokinase receptor (CD87) facilitates CD11b/CD18-mediated adhesion of human monocytes," J Clin Invest., vol. 97:1942-1951.

Sloand, E.M., 2005, "Soluble urokinase activator receptor (suPAR) in stem cell mobilization," Blood, vol. 105:1847-1848.

Stahl et al., 1994, "Binding of urokinase to its receptor promotes migration and invasion of human melanoma cells in vitro," Cancer Res., vol. 54:3066-3071.

Stahl et al., 1995, "The urokinase-type plasminogen activator receptor, a GPI-linked protein, is localized in caveolae," J Cell Biol., vol. 129:335-344.

Szekanecz et al., 1997, "Differential expression of the urokinase receptor (CD87) in arthritic and normal synovial tissues," J Clin Pathol., vol. 50:314-319.

Tang et al., 2008, "Signaling through urokinase and urokinase receptor in lung cancer cells requires interactions with β1 integrins," J Cell Sci. vol. 121(Pt 22):3747-3756.

Tarui et al., 2003, "Critical role of integrin α5 β1 in urokinase (uPA)/urokinase receptor (uPAR, CD87) signaling," J Biol Chem., vol. 278: 29863-29872.

Tarui et al., 2001, "Urokinase-type plasminogen activator receptor (CD87) is a ligand for integrins and mediates cell-cell interaction," J Biol Chem., vol. 276:3983-3990.

Vajdos et al., 2002, "Comprehensive functional maps of the antigen-binding site of an anti-ErbB2 antibody obtained with shotgun scanning mutagenesis," J Mol Biol. , vol. 320(2):415-428.

Vilhardt et al., 1999, "Urokinase-type plasminogen activator receptor is internalized by different mechanisms in polarized and nonpolarized Madin-Darby canine kidney epithelial cells," Molec Biol Cell., vol. 10:179-195.

Wilhelm et al., 1999, "Cellular glycosylphosphatidylinositol-specific phospholipase D regulates urokinase receptor shedding and cell surface expression," J Cell Physiol. vol. 180:225-235.

Wong et al., 1996, "Mechanisms of pertussis toxin-induced myelomonocytic cell adhesion: role of Mac-1(CD11b/CD18) and urokinase receptor (CD87)," Immunology, vol. 88:90-97.

Xu et al., 1997, "Endothelial and macrophage upregulation of urokinase receptor expression in human renal cell carcinoma," Hum Pathol., vol. 28:206-13.

Yamamoto et al., 1994, "Expression and localization of urokinase-type plasminogen activator receptor in human gliomas," Cancer Res., vol. 54:5016-5020.

Zhang et al., 1999, "Mapping and characterization of the epitope(s) of Sch 55700, a humanized mAb, that inhibits human IL-5," Int Immunol. vol. 11(12):1935-43.

Zhu et al., 2002, "Enhanced expression of the LDL receptor family member LR11 increases migration of smooth muscle cells in vitro," Circulation, vol. 105:1830-1836.

uPAR (FL-290): sc-10815, Santa Cruz Biotechnology, Inc., [online], [retrieved on Sep. 28, 2006] Retrieved from the website of Santa Cruz Biotechnology, Inc. using Internet <URL: http://www.santacruzbiotechnology.com/table.php?table=uPAR>.

uPAR (L-17): sc-9796, Santa Cruz Biotechnology, Inc., [online], [retrieved on Sep. 28, 2006] Retrieved from the website of Santa Cruz Biotechnology, Inc. using Internet <URL: http://www.santacruzbiotechnology.com/table.php?table=uPAR>.

uPAR (10G7): sc-13522, Santa Cruz Biotechnology, Inc., [online], [retrieved on Sep. 28, 2006] Retrieved from the website of Santa Cruz Biotechnology, Inc. using Internet <URL: http://www.santacruzbiotechnology.com/table.php?table=uPAR>.

uPAR (IID7): sc-32765, Santa Cruz Biotechnology, Inc., [online], [retrieved on Sep. 28, 2006] Retrieved from the website of Santa Cruz Biotechnology, Inc. using Internet <URL: http://www.santacruzbiotechnology.com/table.php?table=uPAR>.

uPAR (N-19): sc-9793, Santa Cruz Biotechnology, Inc., [online], [retrieved on Sep. 28, 2006] Retrieved from the website of Santa Cruz Biotechnology, Inc. using Internet <URL: http://www.santacruzbiotechnology.com/table.php?table=uPAR>.

uPAR (C-16): sc-9791, Santa Cruz Biotechnology, Inc., [online], [retrieved on Sep. 28, 2006] Retrieved from the website of Santa Cruz Biotechnology, Inc. using Internet <URL: http://www.santacruzbiotechnology.com/table.php?table=uPAR>.

uPAR (IIIF10): sc-32764, Santa Cruz Biotechnology, Inc., [online], [retrieved on Sep. 28, 2006] Retrieved from the website of Santa Cruz Biotechnology, Inc. using Internet <URL: http://www.santacruzbiotechnology.com/table.php?table=uPAR>.

uPAR (M-17): sc-9795, Santa Cruz Biotechnology, Inc., [online], [retrieved on Sep. 28, 2006] Retrieved from the website of Santa Cruz Biotechnology, Inc. using Internet <URL: http://www.santacruzbiotechnology.com/table.php?table=uPAR>.

"Biotinylated anti-human uPAR antibody," R&D Systems, Inc., Catalog No. BAF807, Lot No. BBT03, Apr. 27, 2005, pp. 1-2, [online], [retrieved on Sep. 28, 2006] Retrieved from the website of R&D Systems, Inc. using Internet <URL: http://www.rndsystems.com/product_results.aspx?m=2240&c=6>.

"Monoclonal anti-human uPAR (CD87) antibody," R&D Systems, Inc., Catalog No. MAB807, Clone: 62022, Lot No. CEP01, Oct. 26, 2004, pp. 1-2, [online], [retrieved on Sep. 28, 2006] Retrieved from the website of R&D Systems, Inc. using Internet <URL: http://www.rndsystems.com/product_results.aspx?m=2240&c=6>.

"Monoclonal anti-human CD87/uPAR-phycoerythrin," R&D Systems, Inc., Catalog No. FAB807P, Clone No. 62022, Aug. 2004, pp. 1-2, [online], [retrieved on Sep. 28, 2006] Retrieved from the website of R&D Systems, Inc. using Internet <URL: http://www.rndsystems.com/product_results.aspx?m=2240&c=6>.

"Monoclonal anti-mouse uPAR/CD87 antibody," R&D Systems, Inc., Catalog No. MAB531, Clone No. 109801, Lot No. EQJ01, Jan. 11, 2005, [online], [retrieved on Sep. 28, 2006] Retrieved from the website of R&D Systems, Inc. using Internet <URL: http://www.rndsystems.com/product_results.aspx?m=2240&c=6>.

"Monoclonal antibody against human uPA receptor (CD 87)—Product No. 3936," American Diagnostica Inc., [online], [retrieved in 2006] Retrieved from the website of American Diagnostica Inc. using Internet <URL: http://www.americandiagnostica.com>.

"Monoclonal antibody against human uPAR (CD87)—Product No. 3937," American Diagnostica Inc., [online], [retrieved in 2006] Retrieved from the website of American Diagnostica Inc. using Internet <URL: http://www.americandiagnostica.com>.

"Domain specific monoclonal antibodies against human uPAR—Products No. 3931 and No. 3932," American Diagnostica Inc., [online], [retrieved in 2006] Retrieved from the website of American Diagnostica Inc. using Internet <URL: http://www.americandiagnostica.com>.

"Goat anti-human urokinase receptor IgG—Product No. 399G," American Diagnostica Inc., [online], [retrieved in 2006] Retrieved from the website of American Diagnostica Inc. using Internet <URL: http://www.americandiagnostica.com>.

"Rabbit anti-rat urokinase receptor IgG—Product No. 3920," American Diagnostica Inc., [online], [retrieved in 2006] Retrieved from the website of American Diagnostica Inc. using Internet <URL: http://www.americandiagnostica.com>.

Allgayer, H., 2010, "Translational research on u-PAR", Eur J Cancer, 46(7):1241-51.

Ateeq et al., 2007, "A selective anti-urokinase receptor (uPAR) antibody (ATN-658) blocks prostate cancer growth, migration, invasion and skeletal metastasis in vitro and in vivo", Proceedings of the Annual Meeting of the American Association for Cancer Research, 48:969-970, Abstract #4094.

Callahan et al., 2005, "In vitro and in vivo characterization of a monoclonal antibody, ATN-658, targeting the uPA system," Proceedings of the Annual Meeting of the American Association for Cancer Research, 46:1454-1455, Abstract #6179.

Mazar, A.P., 2008, "Urokinase plasminogen activator receptor choreographs multiple ligand interactions: implications for tumor progression and therapy", Clin Cancer Res., 14(18):5649-55.

Van Buren et al., 2009, "Targeting the urokinase plasminogen activator receptor with a monoclonal antibody impairs the growth of human colorectal cancer in the liver," Cancer, 115(14):3360-8.

Supplementary European Search Report, dated Jun. 14, 2010, for App. No. 07 862 653.8.

* cited by examiner

```
           10         20         30         40         50         60
    MGHPPLLPLL LLLHTCVPAS WGLRCMQCKT NGDCRVEECA LGQDLCRTTI VRLWEEGEEL 70         80         90        100        110        120
    ELVEKSCTHS EKTNRTLSYR TGLKITSLTE VVCGLDLCNQ GNSGRAVTYS RSRYLECISC 130        140        150        160        170        180
    GSSDMSCERG RHQSLQCRSP EEQCLDVVTH WIQEGEEGRP KDDRHLRGCG YLPGCPGSNG 190        200        210        220        230        240
    FHNNDTFHFL KCCNTTKCNE GPILELENLP QNGRQCYSCK GNSTHGCSSE ETFLIDCRGP 250        260        270        280        290        300
    MNQCLVATGT HEPKNQSYMV RGCATASMCQ HAHLGDAFSM NHIDVSCCTK SGCNHPDLDV 310        320        330
    QYRSGAAPQP GPAHLSLTIT LLMTARLWGG TLLWT
```

FIG. 1

```
        265                    279
        CCTKSGCNHPDLDV
```

| Human uPAR Mutation | ATN-658 Binding | ATN-617 Binding |
|---|---|---|
| WT | ++++ | ++++ |
| T267A | ++++ | ++++ |
| K268A | +++ | ++++ |
| S269A | ++++ | ++++ |
| H273A | + | ++++ |
| P274A | ++++ | nd |
| D275A | ++ | nd |
| D277A | +++ | nd |
| V278A | ++++ | nd |
| Q279A | ++++ | nd |

FIG. 6

SEQUENCE LISTING

<160> NUMBER OF SEQ ID NOS: 16

<210> SEQ ID NO 1
<211> LENGTH: 141
<212> TYPE: PRT
<213> ORGANISM: mouse
<220> FEATURE:
<223> OTHER INFORMATION: light chain variable region of antibody ATN-658

<400> SEQUENCE: 1

Asp Val Val Met Thr Gln Thr Pro Leu Thr Leu Ser Val Thr Ile Gly
1               5                   10                  15

-continued

Gln Pro Ala Ser Ile Ser Cys Lys Ser Ser Gln Ser Leu Leu Asp Ser
            20                  25                  30

Asp Gly Lys Thr Tyr Leu Asn Trp Leu Leu Gln Arg Pro Gly Gln Ser
        35                  40                  45

Pro Lys Arg Leu Ile Tyr Leu Val Ser Lys Leu Asp Ser Gly Val Pro
    50                  55                  60

Asp Arg Phe Thr Gly Ser Gly Ser Gly Thr Asp Phe Thr Leu Lys Ile
65                  70                  75                  80

Ser Arg Val Glu Ala Glu Asp Leu Gly Val Tyr Tyr Cys Trp Gln Gly
                85                  90                  95

Thr His Phe Pro Leu Thr Phe Gly Ala Gly Thr Lys Leu Glu Leu Lys
            100                 105                 110

Arg Ala Asp Ala Ala Pro Thr Val Ser Ile Phe Pro Pro Ser Ser Glu
        115                 120                 125

Gln Leu Thr Ser Gly Gly Ala Ser Val Val Cys Phe Leu
    130                 135                 140

<210> SEQ ID NO 2
<211> LENGTH: 141
<212> TYPE: PRT
<213> ORGANISM: mouse
<220> FEATURE:
<223> OTHER INFORMATION: heavy chain variable region of antibody ATN-658

<400> SEQUENCE: 2

Glu Val Gln Leu Gln Gln Ser Gly Pro Glu Leu Val Lys Thr Gly Ala
1               5                   10                  15

Ser Val Lys Ile Ser Cys Lys Ala Ser Gly Tyr Ser Phe Thr Ser Tyr
            20                  25                  30

Tyr Met His Trp Val Lys Gln Ser His Gly Lys Ser Leu Glu Trp Ile
        35                  40                  45

Gly Glu Ile Asn Pro Tyr Asn Gly Gly Ala Ser Tyr Asn Gln Lys Ile
    50                  55                  60

Lys Gly Arg Ala Thr Phe Thr Val Asp Thr Ser Ser Arg Thr Ala Tyr
65                  70                  75                  80

Met Gln Phe Asn Ser Leu Thr Ser Glu Asp Ser Ala Val Tyr Tyr Cys
                85                  90                  95

Ala Arg Ser Ile Tyr Gly His Ser Val Leu Asp Tyr Trp Gly Gln Gly
            100                 105                 110

Thr Ser Val Ser Val Ser Ser Ala Lys Thr Thr Pro Pro Ser Val Tyr
        115                 120                 125

Pro Leu Ala Pro Gly Ser Ala Ala Gln Thr Asn Ser Met
    130                 135                 140

<210> SEQ ID NO 3
<211> LENGTH: 16
<212> TYPE: PRT
<213> ORGANISM: Artificial Sequence
<220> FEATURE:
<223> OTHER INFORMATION: CDR L1 of ATN-658

<400> SEQUENCE: 3

Lys Ser Ser Gln Ser Leu Leu Asp Ser Asp Gly Lys Thr Tyr Leu Asn
1               5                   10                  15

<210> SEQ ID NO 4
<211> LENGTH: 7
<212> TYPE: PRT
<213> ORGANISM: Artificial Sequence
<220> FEATURE:

```
-continued

<223> OTHER INFORMATION: CDR L2 of ATN-658

<400> SEQUENCE: 4

Leu Val Ser Lys Leu Asp Ser
 1               5

<210> SEQ ID NO 5
<211> LENGTH: 9
<212> TYPE: PRT
<213> ORGANISM: Artificial Sequence
<220> FEATURE:
<223> OTHER INFORMATION: CDR L3 of ATN-658

<400> SEQUENCE: 5

Trp Gln Gly Thr His Phe Pro Leu Thr
 1               5

<210> SEQ ID NO 6
<211> LENGTH: 10
<212> TYPE: PRT
<213> ORGANISM: Artificial Sequence
<220> FEATURE:
<223> OTHER INFORMATION: CDR H1 of ATN-658

<400> SEQUENCE: 6

Gly Tyr Ser Phe Thr Ser Tyr Tyr Met His
 1               5                  10

<210> SEQ ID NO 7
<211> LENGTH: 17
<212> TYPE: PRT
<213> ORGANISM: Artificial Sequence
<220> FEATURE:
<223> OTHER INFORMATION: CDR H2 of ATN-658

<400> SEQUENCE: 7

Glu Ile Asn Pro Tyr Asn Gly Gly Ala Ser Tyr Asn Gln Lys Ile Lys
 1               5                  10                  15

Gly

<210> SEQ ID NO 8
<211> LENGTH: 10
<212> TYPE: PRT
<213> ORGANISM: Artificial Sequence
<220> FEATURE:
<223> OTHER INFORMATION: CDR H3 of ATN-658

<400> SEQUENCE: 8

Ser Ile Tyr Gly His Ser Val Leu Asp Tyr
 1               5                  10

<210> SEQ ID NO 9
<211> LENGTH: 19
<212> TYPE: PRT
<213> ORGANISM: Homo sapiens
<220> FEATURE:
<223> OTHER INFORMATION: amino acid 265-283 of human uPAR

<400> SEQUENCE: 9

Cys Cys Thr Lys Ser Gly Cys Asn His Pro Asp Leu Asp Val Gln Tyr
 1               5                  10                  15

Arg Ser Gly

<210> SEQ ID NO 10
<211> LENGTH: 18
<212> TYPE: PRT
```

```
<213> ORGANISM: Homo sapiens
<220> FEATURE:
<223> OTHER INFORMATION: amino acid 265-282 of human uPAR

<400> SEQUENCE: 10

Cys Cys Thr Lys Ser Gly Cys Asn His Pro Asp Leu Asp Val Gln Tyr
 1               5                  10                  15

Arg Ser

<210> SEQ ID NO 11
<211> LENGTH: 17
<212> TYPE: PRT
<213> ORGANISM: Homo sapiens
<220> FEATURE:
<223> OTHER INFORMATION: amino acid 265-281 of human uPAR

<400> SEQUENCE: 11

Cys Cys Thr Lys Ser Gly Cys Asn His Pro Asp Leu Asp Val Gln Tyr
 1               5                  10                  15

Arg

<210> SEQ ID NO 12
<211> LENGTH: 16
<212> TYPE: PRT
<213> ORGANISM: Homo sapiens
<220> FEATURE:
<223> OTHER INFORMATION: amino acid 265-280 of human uPAR

<400> SEQUENCE: 12

Cys Cys Thr Lys Ser Gly Cys Asn His Pro Asp Leu Asp Val Gln Tyr
 1               5                  10                  15

<210> SEQ ID NO 13
<211> LENGTH: 15
<212> TYPE: PRT
<213> ORGANISM: Homo sapiens
<220> FEATURE:
<223> OTHER INFORMATION: amino acid 265-279 of human uPAR

<400> SEQUENCE: 13

Cys Cys Thr Lys Ser Gly Cys Asn His Pro Asp Leu Asp Val Gln
 1               5                  10                  15

<210> SEQ ID NO 14
<211> LENGTH: 16
<212> TYPE: PRT
<213> ORGANISM: Homo sapiens
<220> FEATURE:
<223> OTHER INFORMATION: amino acid 98-114 of human uPAR

<400> SEQUENCE: 14

Cys Gly Ser Ser Asp Met Ser Cys Glu Arg Gly Arg His Gln Ser Leu
 1               5                  10                  15

<210> SEQ ID NO 15
<211> LENGTH: 335
<212> TYPE: PRT
<213> ORGANISM: Homo sapiens
<220> FEATURE:
<223> OTHER INFORMATION: human uPAR (GenBank accession No. Q03405)

<400> SEQUENCE: 15

Met Gly His Pro Pro Leu Leu Pro Leu Leu Leu Leu His Thr Cys
 1               5                  10                  15

Val Pro Ala Ser Trp Gly Leu Arg Cys Met Gln Cys Lys Thr Asn Gly
                20                  25                  30
```

```
Asp Cys Arg Val Glu Glu Cys Ala Leu Gly Gln Asp Leu Cys Arg Thr
         35                  40                  45

Thr Ile Val Arg Leu Trp Glu Glu Gly Glu Glu Leu Glu Leu Val Glu
 50                  55                  60

Lys Ser Cys Thr His Ser Glu Lys Thr Asn Arg Thr Leu Ser Tyr Arg
 65                  70                  75                  80

Thr Gly Leu Lys Ile Thr Ser Leu Thr Glu Val Val Cys Gly Leu Asp
                 85                  90                  95

Leu Cys Asn Gln Gly Asn Ser Gly Arg Ala Val Thr Tyr Ser Arg Ser
                100                 105                 110

Arg Tyr Leu Glu Cys Ile Ser Cys Gly Ser Ser Asp Met Ser Cys Glu
             115                 120                 125

Arg Gly Arg His Gln Ser Leu Gln Cys Arg Ser Pro Glu Glu Gln Cys
         130                 135                 140

Leu Asp Val Val Thr His Trp Ile Gln Glu Gly Glu Glu Gly Arg Pro
145                 150                 155                 160

Lys Asp Asp Arg His Leu Arg Gly Cys Gly Tyr Leu Pro Gly Cys Pro
                165                 170                 175

Gly Ser Asn Gly Phe His Asn Asn Asp Thr Phe His Phe Leu Lys Cys
                180                 185                 190

Cys Asn Thr Thr Lys Cys Asn Glu Gly Pro Ile Leu Glu Leu Glu Asn
            195                 200                 205

Leu Pro Gln Asn Gly Arg Gln Cys Tyr Ser Cys Lys Gly Asn Ser Thr
        210                 215                 220

His Gly Cys Ser Ser Glu Glu Thr Phe Leu Ile Asp Cys Arg Gly Pro
225                 230                 235                 240

Met Asn Gln Cys Leu Val Ala Thr Gly Thr His Glu Pro Lys Asn Gln
                245                 250                 255

Ser Tyr Met Val Arg Gly Cys Ala Thr Ala Ser Met Cys Gln His Ala
                260                 265                 270

His Leu Gly Asp Ala Phe Ser Met Asn His Ile Asp Val Ser Cys Cys
            275                 280                 285

Thr Lys Ser Gly Cys Asn His Pro Asp Leu Asp Val Gln Tyr Arg Ser
        290                 295                 300

Gly Ala Ala Pro Gln Pro Gly Pro Ala His Leu Ser Leu Thr Ile Thr
305                 310                 315                 320

Leu Leu Met Thr Ala Arg Leu Trp Gly Gly Thr Leu Leu Trp Thr
                325                 330                 335

<210> SEQ ID NO 16
<211> LENGTH: 10
<212> TYPE: PRT
<213> ORGANISM: Homo sapiens
<220> FEATURE:
<223> OTHER INFORMATION: amino acid 268-277 of human uPAR

<400> SEQUENCE: 16

Lys Ser Gly Cys Asn His Pro Asp Leu Asp
 1               5                  10
```

UROKINASE-TYPE PLASMINOGEN ACTIVATOR RECEPTOR EPITOPE, MONOCLONAL ANTIBODIES DERIVED THEREFROM AND METHODS OF USE THEREOF

CROSS REFERENCES TO RELATED APPLICATIONS

This application claims the benefit of U.S. Provisional Application No. 60/873,627 filed Dec. 8, 2006 and U.S. Provisional Application No. 60/930,034 filed May 11, 2007, each of which is incorporated by reference herein in its entirety.

1. FIELD OF THE INVENTION

The present invention relates to a urokinase-type plasminogen activator receptor (uPAR) epitope, monoclonal antibodies that immunospecifically bind this epitope, and uses thereof for the treatment or prevention of a disease, e.g., cancer. These antibodies may inhibit the interaction of uPA/uPAR complexes with additional molecules with which these complexes interact. The antibodies of the invention can be used in diagnostic and therapeutic methods, particularly for cancer.

2. BACKGROUND OF THE INVENTION

A significant body of evidence from studies in vitro and in vivo has established that the urokinase plasminogen activator (uPA) system is central to the process of metastasis, making it a promising target for cancer drug development (Mazar, A P et al. (1999) Angiogenesis 3: 15-32). In addition to uPA, its cell surface receptor (uPAR) is a suitable target for the design and development of cancer therapeutic and diagnostic agents (Mazar, A P (2001) Anti-Cancer Drugs 12: 397-400) because:

(a) uPAR is selectively expressed on some tumor cells, angiogenic endothelial cells ("ECs"), and other tumor associated cells, such as tumor associated inflammatory cells and tumor associated fibroblasts, but not on most quiescent, normal cells;

(b) uPAR is an important participant in several extracellular and intracellular pathways required for metastasis that are currently the object of intense drug development efforts; and (c) it is possible to interfere at several different points along the uPA pathway. Thus, uPA and uPAR are promising targets for the development of diagnostics and therapeutics useful against many different types of tumors/cancers.

Membrane-associated uPAR is a glycosylphosphatidylinositol-anchored (GPI)-anchored protein (Slound, E. M., *Blood* 105:1847-1848 (2005)). uPAR is composed of 3 domains; domain 1 (D1) is the N-terminal domain, domain 2 (D2) connects D1 to domain 3 (D3), and D3 is the C-terminal domain that anchors the molecule to the cell membrane through a GPI tail to $Gly^{283}$ of D3 (Montuori et al., *J. Biol. Chem.* 277:46932-46939 (2002); Dano et al., *Fibrinolysis* 8:189-203 (1994)). When uPAR is cleaved at the GPI anchor by phospholipase C (Ploug et al., *J Biol Chem.* 266:1926-1933 (1991)) or phospholipase D, soluble uPAR (suPAR) is released from the cell membrane (Wilhelm et al., *J. Cell Physiol.* 180:225-235 (1999)).

2.1. The uPA/uPAR System and Cancer

Metastasis and angiogenesis share many common functional features that characterize invasive and migratory processes of tumor cells and of ECs. These features include (1) the up-regulation of protease and integrin expression, (2) the loss of cell-cell and cell-matrix contacts, (3) increased responsiveness to growth and differentiation factors, and (4) remodeling of extracellular matrix (ECM) and basement membrane (BasM). All of these contribute to tumor progression.

The uPA "system," which comprises the serine protease uPA, its receptor uPAR, and its specific serpin inhibitor, plasminogen activator inhibitor-type 1 (PAI-1), plays a central role in many of these activities. The activity of this system is responsible for:

(1) initiating cascades that result in the activation of plasminogen, activating several pro-metalloproteases (proMMPs), (2) release and processing of latent growth factors such as fibroblast growth factor-2 (FGF-2), vascular endothelial growth factor (VEGF), hepatocyte growth factor (HGF), and transforming growth factor-β (TGFβ), (3) (a) interactions with components of the ECM such as vitronectin (Vn) and fibronectin (Fn), (b) direct interactions with several integrins including α5β1 and αvβ3, and (c) remodeling the BasM and ECM to promote cell motility. Further, the uPA system can also initiate localized fibrin turnover which may play a role in angiogenesis.

The expression of uPA and uPAR has been demonstrated in numerous tumor types including glioblastoma, prostate, breast, colon, hepatocellular, and renal cell carcinoma (Mizukami I F et al. (1994) Clin Immunol and Immunopathol 71:96-104; Hsu D W et al., (1995) Am J Pathol 147:114-23; de Witte J H et al. (1999) Br J Cancer 79:1190-8). The expression of uPA and uPAR are typically greater in more aggressive forms of disease. On tumor cells, this expression is often highest at the invasive front of the tumor (Buo, L et al., (1995) Human Pathol 26:1133-1138; Yamamoto M et al. (1994) Cancer Res 54:5016-5020). Strong immunohistochemical staining for uPAR in blood vessels associated with the invasive front of breast, colon, and renal cell carcinomas has been reported (Bastholm L et al. Appl Immunohistochem Mol Morphol 7: 39-47; Nakata S et al. (1998) Int. J. Cancer 79:179-186). In the colon carcinoma study, uPAR co-localized with VEGF. The expression of uPA and uPAR has also been observed on tumor-associated macrophages in several tumor types (Ohtani H et al. (1995) Int J Cancer 62:691-6; Xu Y et al. (1997) Hum Pathol 28:206-13). uPA is chemotactic for monocytes and mediates both adhesion and migration of these cells. Adhesion and migration require only uPAR occupancy but not uPA catalytic activity. Thus, the uPA system is believed to contribute to tumor progression by acting on multiple tumor-associated cell types.

Several recent studies have evaluated the therapeutic potential of inhibiting the binding of uPA to uPAR in syngeneic systems. The delivery of an adenovirus-encoded murine amino-terminal fragment of uPA (abbreviated "ATF"—this is the domain of uPA that contains the uPAR binding region) directly into tumors resulted in (a) suppression of neovascularization and (b) arrest of tumor growth (Li H et al. (1998) Gene Ther 5:1105-1113). Due to species "specificity," murine ATF would be expected to bind only to murine host ECs and leukocytes, not to human tumor cells. This indicates that the tumor inhibition was mediated through the suppression of the host angiogenic response. Finally, a polyclonal antibody raised against a 100-residue fragment of rat uPAR selectively localized to a rat breast tumor which grew from cells of the Mat BIII cell line (Rabbani S A et al. (2002) Cancer Res 62: 2390-97). This polyclonal antibody completely inhibited tumor growth and led to tumor regression.

Unfortunately, despite the promise of targeting the uPA system for therapeutic and diagnostic purposes, research efforts have not resulted in the development of agents suitable for the clinic. Small molecule approaches have been hampered by (1) the difficulty of potently inhibiting a protein-protein interaction (e.g., uPA-uPAR or uPAR-integrin), and (2) the lack of suitable leads or structural information amenable to medicinal chemistry efforts. Several potent peptide inhibitors of the uPA-uPAR interaction have been identified but these would suffer from the typically poor pharmacological properties of peptides and have not demonstrated the requisite levels of activity even in cell-based assays (Ploug M et al. (2001) *Biochemistry* 40:12157-68).

3. SUMMARY OF THE INVENTION

The present invention is based, in part, on the characterization of the epitope of the uPAR-specific monoclonal antibody, ATN-658. Accordingly, the present invention provides an isolated or purified peptide consisting of the amino acid sequence CCTKSGCNHPDLDVQYRSG (SEQ ID NO: 9), CCTKSGCNHPDLDVQYRS (SEQ ID NO: 10), CCTKSGCNHPDLDVQYR (SEQ ID NO: 11), CCTKSGCNHPDLDVQY (SEQ ID NO: 12), CCTKSGCNHPDLDVQ (SEQ ID NO: 13), CGSSDMSCERGRHQSL (SEQ ID NO: 14), or KSGCNHPDLD (SEQ ID NO: 16). The epitope sequence may also be part of a longer sequence, e.g., 20, 25, 30, 35, 40, 45, 50, 75, 100, 150, or 200 amino acids, where the longer sequence is a fragment of human uPAR and comprises the epitope sequence.

In one embodiment, the present invention provides methods of producing an antibody, which comprises (i) immunizing a mammal with a peptide (optionally, purified) of the invention; (ii) isolating splenocytes from said mammal; (iii) fusing said splenocytes to myeloma cells; and (iv) selecting a hybridoma. In another embodiment, the present invention provides methods of producing an antibody, which comprises (i) immunizing a mammal with a peptide comprising a conformation-dependent epitope defined by (a) CCTKSGCNHPDLDVQYRSG (SEQ ID NO: 9), CCTKSGCNHPDLDVQYRS (SEQ ID NO: 10), CCTKSGCNHPDLDVQYR (SEQ ID NO: 11), CCTKSGCNHPDLDVQY (SEQ ID NO: 12) or CCTKSGCNHPDLDVQ (SEQ ID NO: 13); and (b) CGSSDMSCERGRHQSL (SEQ ID NO: 14) of a human uPAR (SEQ ID NO: 15); (ii) isolating splenocytes from said mammal; (iii) fusing said splenocytes to myeloma cells; and (iv) selecting a hybridoma that secretes an antibody that binds said peptide. In some embodiments, the present invention provides methods of producing an antibody, which comprises (i) immunizing a mammal with a peptide comprising a conformation-dependent epitope defined by (a) KSGCNHPDLD (SEQ ID NO: 16); and (b) CGSSDMSCERGRHQSL (SEQ ID NO: 14) of a human uPAR (SEQ ID NO: 15); (ii) isolating splenocytes from said mammal; (iii) fusing said splenocytes to myeloma cells; and (iv) selecting a hybridoma that secretes an antibody that binds said peptide. In a specific embodiment, the methods of producing an antibody comprise (i) immunizing a mammal with a fragment of human uPAR (optionally, purified) comprising a conformation-dependent epitope defined by (a) KSGCNHPDLD (SEQ ID NO: 16); and (b) CGSSDMSCERGRHQSL (SEQ ID NO: 14) of a human uPAR (SEQ ID NO: 15); (ii) isolating splenocytes from said mammal; (iii) fusing said splenocytes to myeloma cells; and (iv) selecting a hybridoma that secretes an antibody that binds said fragment. In one embodiment, the methods of producing an antibody comprise (i) immunizing a mammal with a fragment of human uPAR (optionally, purified) comprising domains 2 and 3 of human uPAR (SEQ ID NO: 15); (ii) isolating splenocytes from said mammal; (iii) fusing said splenocytes to myeloma cells; and (iv) selecting a hybridoma that secretes an antibody that binds said fragment. In another embodiment, the methods of producing an antibody comprise (i) immunizing a mammal with an isolated fragment of human uPAR (SEQ ID NO: 15), in which the amino terminus of said fragment is at any one of amino acid numbers 93-98 and the carboxy terminus of said fragment is at any one of amino acids 277-283, or a derivative thereof containing only conservative substitutions relative to the sequence of said fragment; (ii) isolating splenocytes from said mammal; (iii) fusing said splenocytes to myeloma cells; and (iv) selecting a hybridoma that secretes an antibody that binds said fragment. In a particular embodiment, the mammal is a non-human mammal, e.g., mouse, rabbit, goat, rat, cat, dog, etc. In another embodiment, the mammal is a human. Methods of producing an antibody using phage display are also encompassed by the invention.

The present invention provides antibodies, or antigen-binding fragments thereof, that immunospecifically bind to an epitope defined by the amino acid sequence CCTKSGCNHPDLDVQYRSG (SEQ ID NO: 9), CCTKSGCNHPDLDVQYRS (SEQ ID NO: 10), CCTKSGCNHPDLDVQYR (SEQ ID NO: 11), CCTKSGCNHPDLDVQY (SEQ ID NO: 12) or CCTKSGCNHPDLDVQ (SEQ ID NO: 13). In certain embodiments, the antibodies, or antigen-binding fragments thereof, immunospecifically bind to an epitope defined by the amino acid sequence KSGCNHPDLD (SEQ ID NO: 16). In certain embodiments, mutating the epitope at amino acid residue 268 reduces or abolishes the immunospecific binding affinity of the antibody. It should be noted that all references in this application to amino acid numbers in the human uPAR sequence refer to numbering from the amino terminus of processed uPAR, which lacks the 22 amino terminal acids shown in FIG. 1, unless explicitly indicated otherwise. The present invention also provides antibodies, or antigen-binding fragments thereof, that immunospecifically bind to a conformation-dependent epitope defined by (i) CCTKSGCNHPDLDVQYRSG (SEQ ID NO: 9), CCTKSGCNHPDLDVQYRS (SEQ ID NO: 10), CCTKSGCNHPDLDVQYR (SEQ ID NO: 11), CCTKSGCNHPDLDVQY (SEQ ID NO: 12) or CCTKSGCNHPDLDVQ (SEQ ID NO: 13); and (ii) CGSSDMSCERGRHQSL (SEQ ID NO: 14) within the context of a human uPAR (SEQ ID NO:15). In some embodiments, the antibodies, or antigen-binding fragments thereof, immunospecifically bind to a conformation-dependent epitope defined by (i) KSGCNHPDLD (SEQ ID NO: 16); and (ii) CGSSDMSCERGRHQSL (SEQ ID NO: 14) within the context of a human uPAR (SEQ ID NO:15). In some embodiments, binding of an antibody to the epitope is demonstrated by a reduction in said binding by said antibody when the K (Lys) residue at position 268 in human uPAR is mutated to a E (Glu) residue (uPAR K268E) or to an A (Ala) residue (uPAR K268A). Preferably, the amount of binding is demonstrated by co-immunoprecipitation of the antibody and uPAR K268E or uPAR K268A. In other embodiments, binding of an antibody to the epitope is demonstrated by a reduction in said binding by said antibody when the H (His) residue at position 273 in human uPAR is mutated to an A (Ala) residue (uPAR H273A). Preferably, the amount of binding is demonstrated by co-immunoprecipitation of the antibody and uPAR H273A. In particular embodiments, binding of an antibody to the epitope is demonstrated by a reduction in said binding by said antibody when the D (Asp) residue at position 275 or 277 in human uPAR is mutated to an A (Ala) residue (uPAR D275A or uPAR D277A, respectively). Preferably, the amount of binding is demonstrated by co-immunoprecipitation of the antibody and uPAR D275A or uPAR D277A, respectively. In the above embodiments, for example, a reduction in binding by the antibody is demonstrated by a decreased amount of mutated uPAR (e.g., uPAR K268E, uPAR K268A, uPAR H273A, uPAR D275A, or uPAR D277A) that co-immunoprecipitates with the antibody relative to the amount of wild-type uPAR (e.g., membrane-bound uPAR or suPAR) or a fragment of suPAR (e.g., D2D3 suPAR) that co-immunoprecipitates with the antibody.

In certain embodiments, the binding of the antibody to an epitope of the invention is demonstrated by a deuterium exchange assay, wherein the binding of an antibody (e.g., ATN-658) to an epitope of a protein (e.g., human suPAR) decreases the ability of that epitope to exchange deuterium. In particular embodiments, human suPAR is contacted with an antibody, and binding of the antibody to an epitope of human uPAR is demonstrated by a reduction in deuteration level over the epitope when in the presence of the antibody under binding conditions, relative to deuteration over the epitope in the absence of the antibody. Conversely, a region of suPAR that is not contacted by the antibody possesses the same or similar deuteration level when in the presence or absence of the antibody under binding conditions. Preferably, the deuteration assay is performed with a fragment of human uPAR containing, or consisting of, domains 2 and 3 (D2D3). In specific embodiments, binding of the antibody to an epitope of human suPAR is demonstrated by a reduction in deuteration level over the epitope of human suPAR, when in the presence of the antibody under binding conditions, of at least 10%, or at least 20%, or at least 30%, or at least 40%, or at least 50%, relative to deuteration level over the epitope in the absence of the antibody.

Preferably, the antibodies or fragments thereof of the invention are isolated or purified. In certain embodiments, the antibody, or antigen-binding fragment thereof, is a monoclonal antibody (preferably an IgG) or a scFv. In certain embodiments, the antibody of the invention can be a human antibody, humanized antibody or chimeric antibody. In certain embodiments, the antibody is a bi-specific antibody. In certain embodiments, the antibody is not ATN-658.

In a preferred embodiment, the antibodies modulate downstream signaling of the urokinase-type plasminogen activator receptor and can interfere with and inhibit uPAR signaling, including, but not limited to, (a) uPAR mediated assembly of fibronectin, (b) binding of fibronectin or a fragment thereof to integrin α5v1 and/or (c) the assembly of vitronectin components. The antibodies can also downregulate the number of uPAR molecules on the cell membrane.

In a preferred embodiment, the antibodies of the invention are conjugated to a detectable label or therapeutic agent. A detectable label includes, but is not limited to, a radionuclide, a PET-imageable agent, an MRI-imageable agent, a fluorescer, a fluorogen, a chromophore, a chromogen, a phosphorescer, a chemiluminescer or a bioluminescer. Representative radionuclides include, but are not limited to, $^{3}H$, $^{14}C$, $^{35}S$, $^{67}Ga$, $^{68}Ga$, $^{72}As$, $^{89}Zr$, $^{97}Ru$, $^{99}Tc$, $^{111}In$, $^{123}I$, $^{125}I$, $^{131}I$, $^{169}Yb$ and $^{201}Tl$. Representative fluorescers or fluorogens include, but are not limited to, fluorescein, rhodamine, dansyl, phycoerythrin, phycocyanin, allophycocyanin, o-phthaldehyde, fluorescamine, a fluorescein derivative, Oregon Green, Rhodamine Green, Rhodol Green and Texas Red. A therapeutic agent includes, but is not limited to, a chemotherapeutic drug, a toxin or a therapeutic radionuclide.

The present invention also provides a pharmaceutical composition comprising an antibody, or antigen-binding fragment thereof, of the invention; and a pharmaceutically acceptable carrier. The pharmaceutical compositions may be used in methods for inhibiting cell migration, cell invasion, cell proliferation or angiogenesis, or for inducing apoptosis, by contacting cells associated with undesired cell migration, invasion, proliferation or angiogenesis with an effective amount of a pharmaceutical composition of the invention. The pharmaceutical compositions may also be used in methods for treating a subject having a disease, disorder or condition characterized by undesired angiogenesis, tumor growth and/or tumor metastasis by administering to the subject a therapeutically effective amount of the pharmaceutical composition of the invention.

4. DESCRIPTION OF THE FIGURES

FIG. 1 provides the amino acid sequence of the unprocessed form of human uPAR (UniProtKB/Swiss-Prot Accession No. Q03405 (SEQ ID NO: 15). The processed (mature) form of human uPAR lacks the first 22 amino acids (indicated in bold).

FIG. 2 shows binding assay data of ATN-658 and ATN-617. HeLa cells were incubated with 5 nM $^{125}I$-scuPA (single chain uPA, see Holmes et al., *Biotechnology* 3:923-929 (1985)) in the presence or absence of either 300 nM unlabeled scuPA or 300 nM ATN-658. ATN-617, an anti-uPAR monoclonal antibody that blocks the binding of uPA to uPAR is shown to compete with scuPA binding as a control. The data show that the monoclonal antibody ATN-658 does not compete with binding of uPA to HeLa cells. Binding of ATN-658 to HeLa cells did not inhibit binding of $^{125}I$-scuPA.

Figure 3:
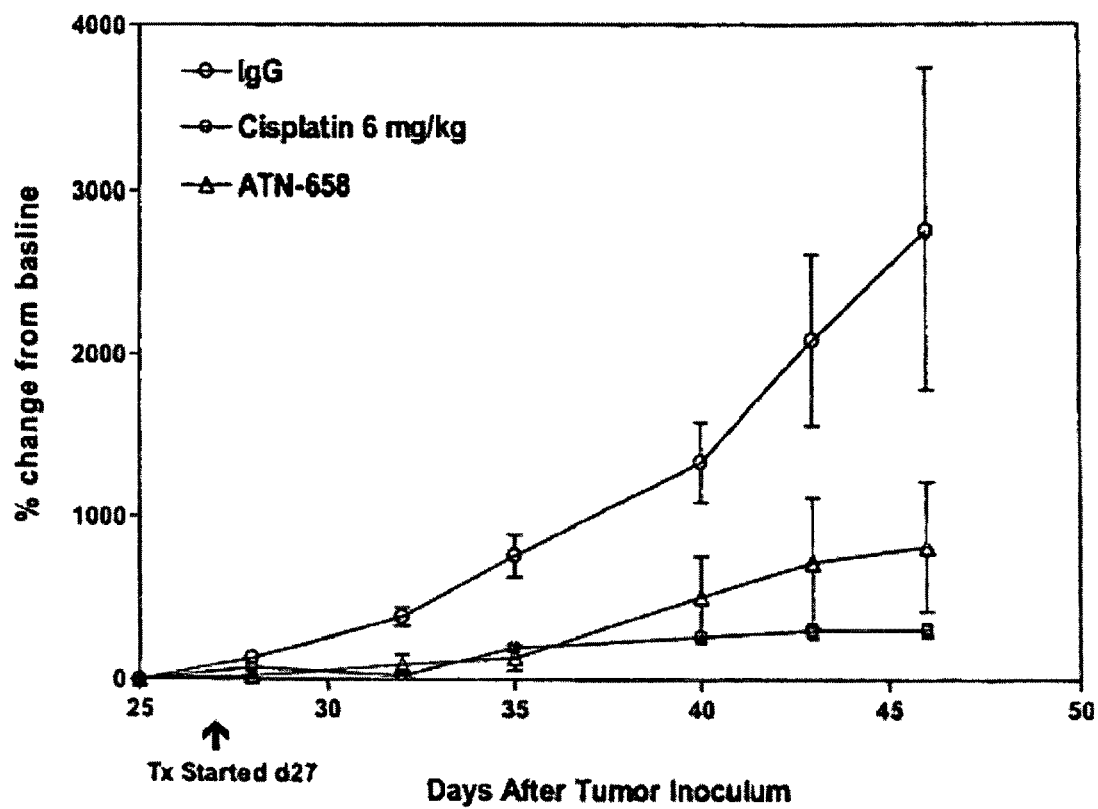

FIG. 3 shows the result of a tumor growth assay in a mouse model of ovarian cancer. The data show that ATN-658 inhibits tumor growth in the A2780 ovarian cancer model as effectively as cisplatin. A2780 cells express only uPAR and not uPA.

Figure 4:
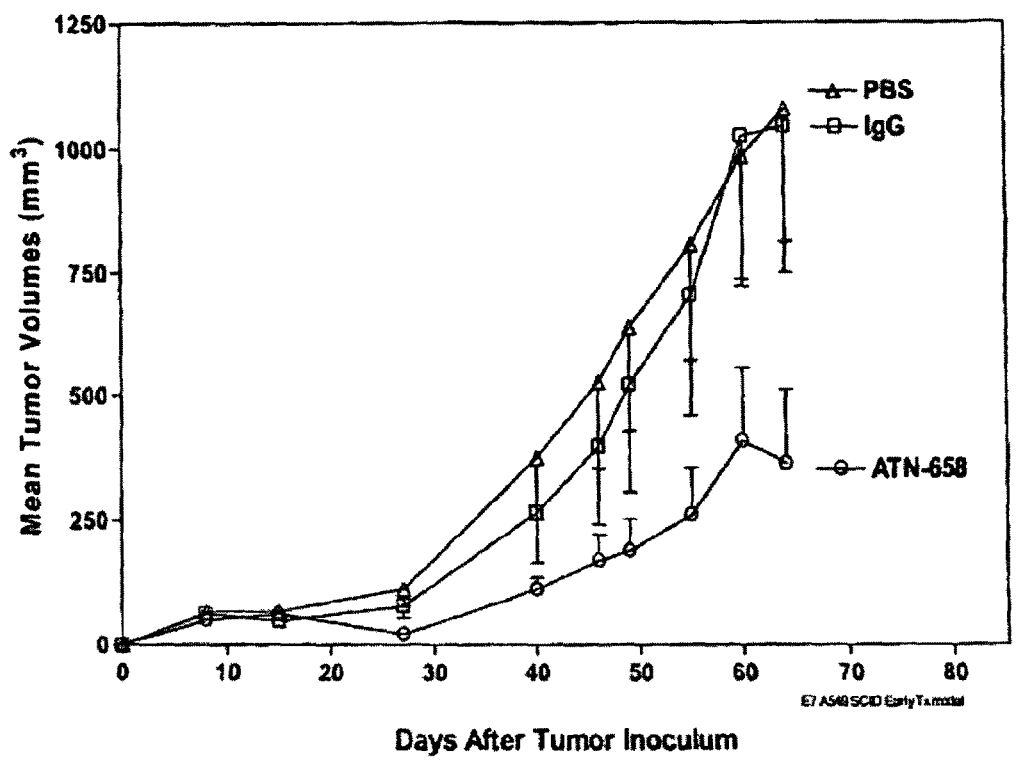

FIG. 4 shows the result of a tumor growth assay in a mouse model of lung cancer. The data show that ATN-658 inhibits tumor growth in an A549 lung cancer (non-small cell) model in which 106 tumor cells were inoculated. A549 cells express both uPA and uPAR.

Figures 5A, 5B:
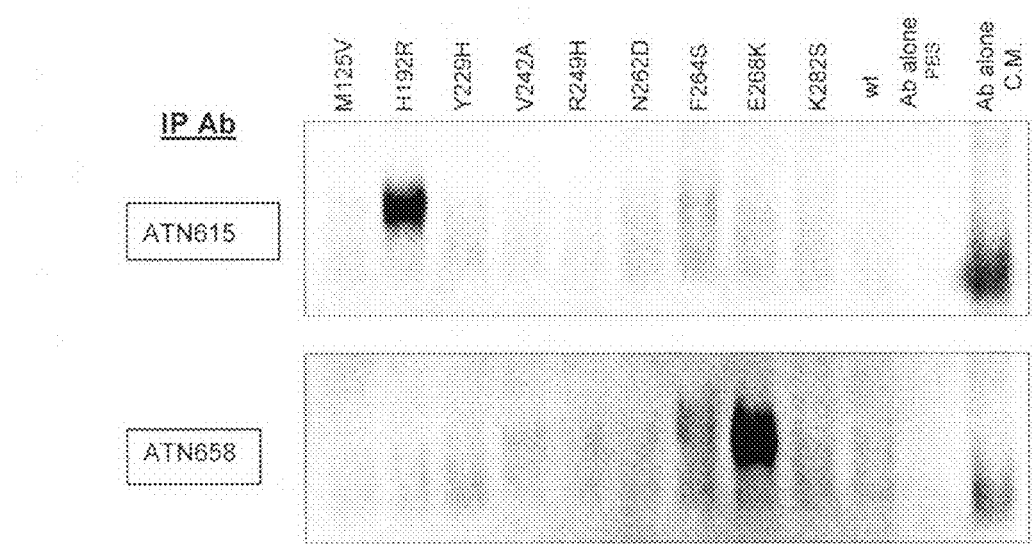

FIG. 5A is a table displaying the 9 amino acid residues of uPAR that differ between humans, African Green monkeys, and Crab eating or Long tailed macaques.

FIG. 5B shows the results of a co-immunoprecipitation assay carried out with ATN-658 (or ATN-615 as a control) and monkey uPAR, wild-type or with the indicated mutations. The immunoprecipitation data show that ATN-658 does not bind to monkey uPAR, but a mutation of monkey uPAR at position 268 from E (Glutamine) to K (Lysine), which corresponds to the amino acid at position 268 in human uPAR, confers binding of ATN-658. Mutating the other amino acid residues of monkey uPAR to the corresponding amino acid residues of human uPAR did not confer binding of ATN-658.

FIG. 6 is a table presenting the binding data from an alanine scanning mutagenesis analysis of human uPAR. The data from the table show that mutations of several amino acid residues, i.e., amino acid residues 268, 273, 275, and 277, of human uPAR reduce binding of ATN-658 to the uPAR epitope. The relative binding affinity of ATN-658 to the respective human uPAR (wild-type or mutated) is indicated, with high binding affinity designated as ++++ and lower affinities designated as +++, ++, and +.

Figure 7A:
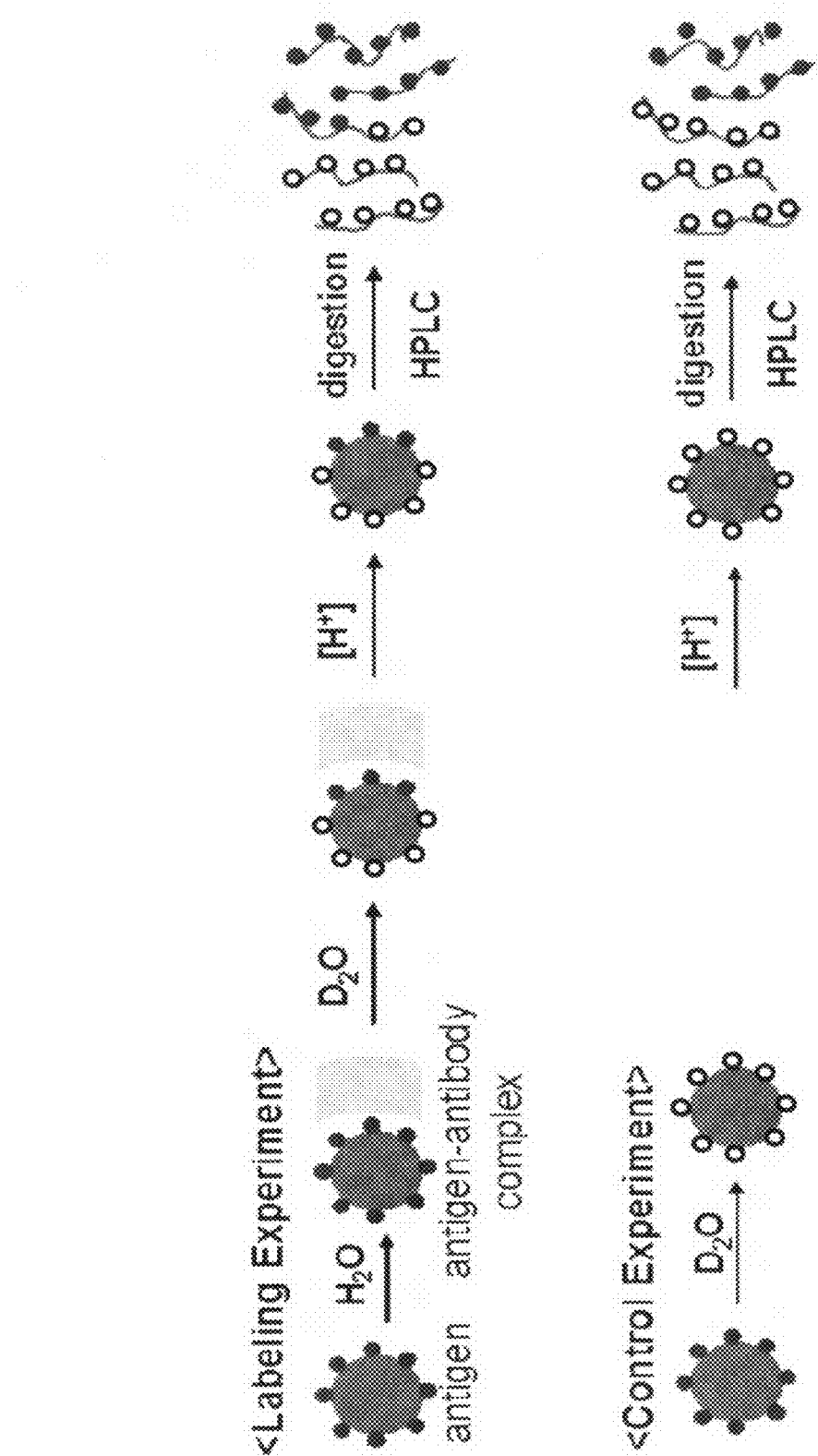
Figure 7B:
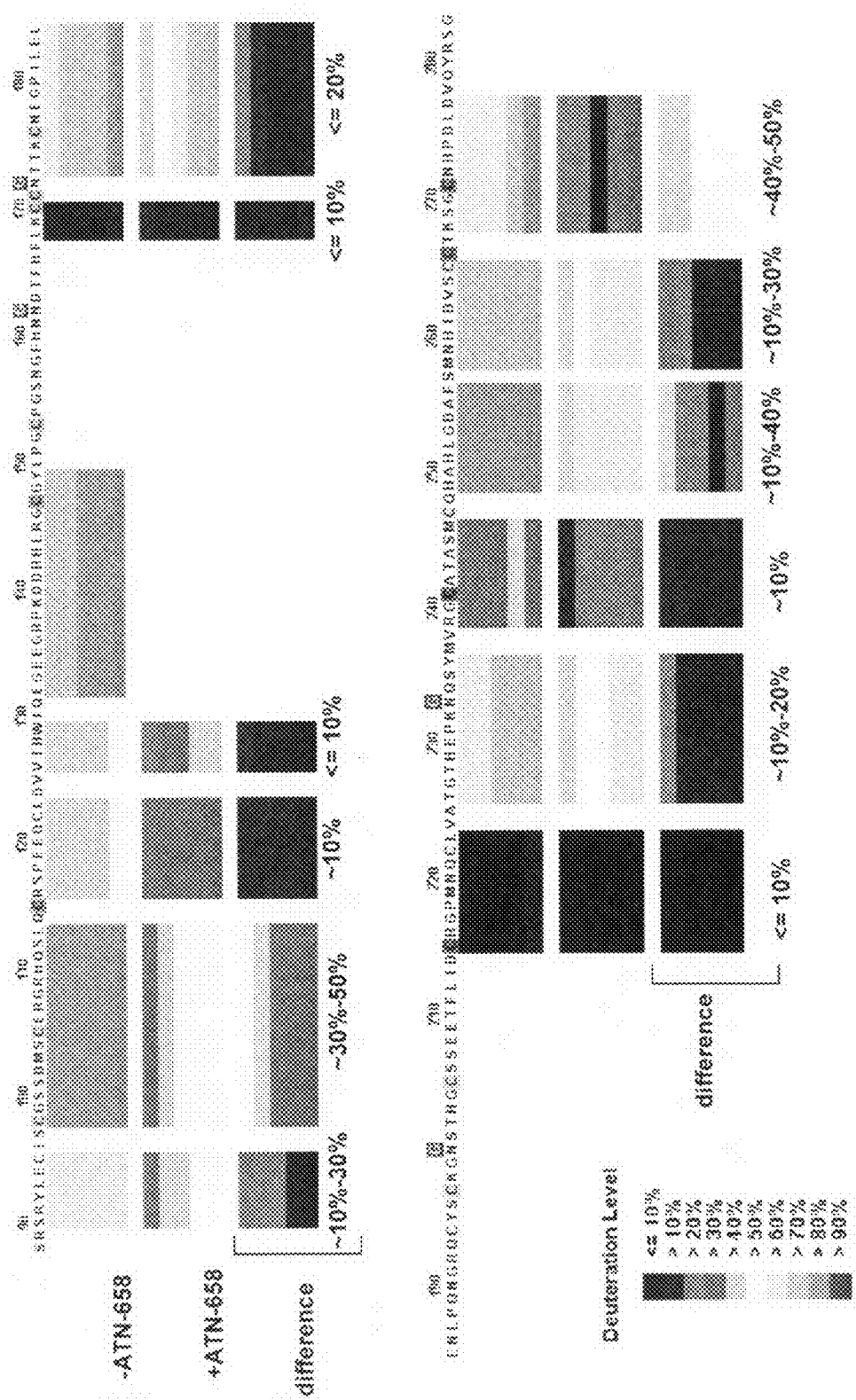
Figure 7C:
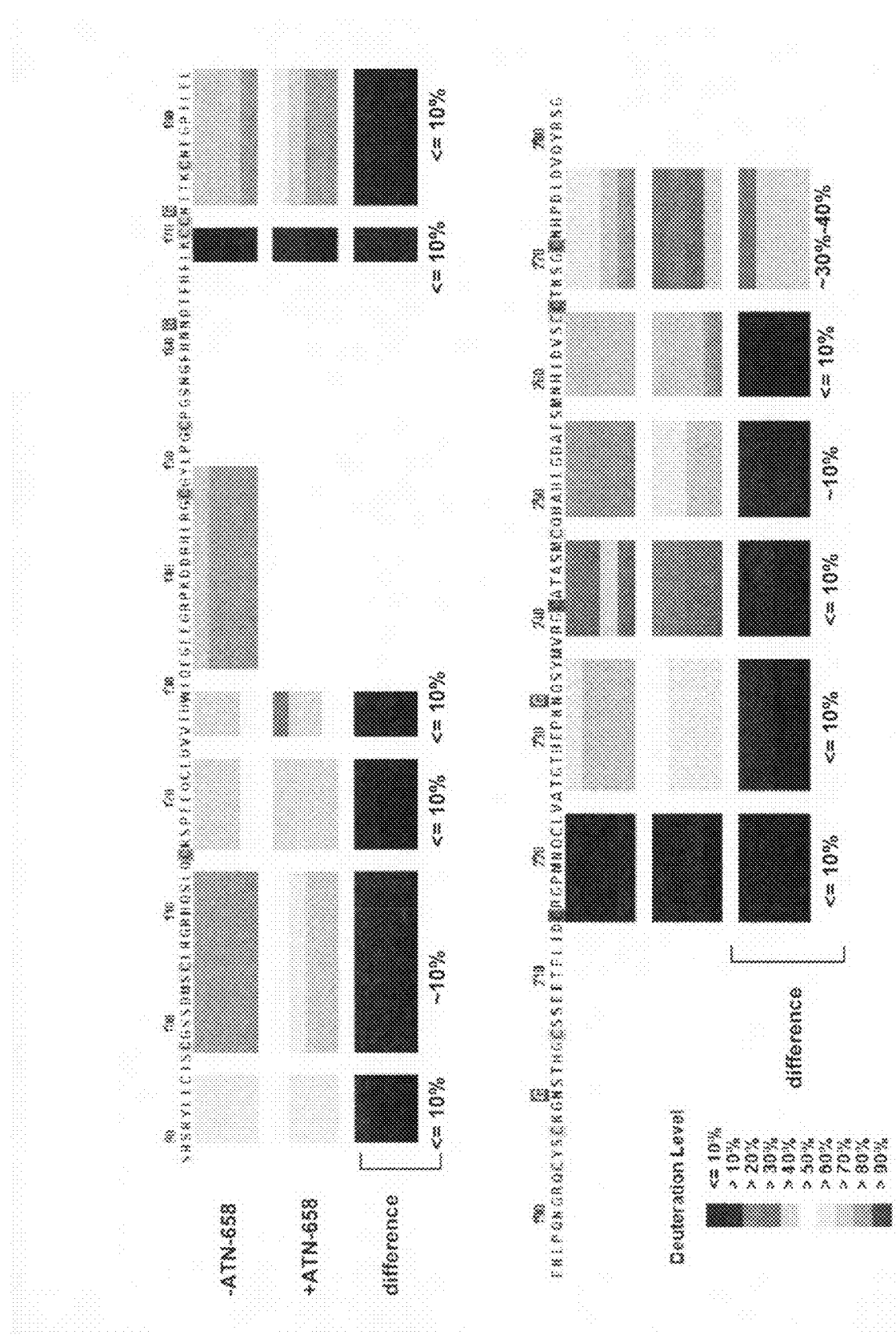

FIG. 7A shows a schematic diagram depicting the steps and principle behind the Deuterium Exchange assay used to map the epitope of human uPAR to which ATN-658 binds; and FIGS. 7B and 7C show the epitope mapping data from Deuterium Exchange assays with human uPAR D2D3 in the presence and absence of ATN-658. The approximate percentage of reduction (difference) in the deuteration level is indicated for the respective epitope region.

5. DETAILED DESCRIPTION OF THE INVENTION uPAR is an ideal target for antibodies because it is expressed on the cell surface. Expression of uPAR at the tumor-vasculature interface (on invasive tumor cells, angiogenic endothelial cells, or tumor-associated macrophages) suggests that antibodies targeting this protein would not suffer the same barriers to diffusion that have led to the failure of other monoclonal antibodies to enter tumors and serve as diagnostic agents or exert therapeutic effects. Importantly, uPAR is not normally expressed on quiescent tissues, which should minimize the potential for toxicity when employing a therapeutic antibody and minimize non-specific signals (or false positives) when employing a diagnostic antibody.

The present invention is based, in part, on the inventors' characterization of the epitope targeted by the uPAR-specific monoclonal antibody, ATN-658. The hybridoma secreting monoclonal antibody ATN-658 has been deposited under the provisions of the Budapest Treaty with the American Type Culture Collection (10801 University Blvd., Manassas, Va. 20110-2209) on Feb. 1, 2007, and assigned ATCC Accession No. PTA-8191. This antibody does not affect the binding of uPA to its receptor. Antibodies that bind to this epitope affect downstream signaling pathways, including such "downstream" ligands as integrins, low-density lipoprotein receptor-related protein (LRP) and other binding partners. These downstream interactions are believed to be important to the processes of cell migration, invasion and proliferation. It is thus desirable to target these processes therapeutically or detect the process or their interacting components diagnostically.

Accordingly, the present invention relates to methods and compositions that provide for the prevention and treatment of cancer. A particular aspect of the invention relates to methods and compositions containing compounds that inhibit cancer cell proliferation and invasion.

The invention further provides diagnostic methods using the uPAR antibodies of the invention. The diagnostic methods of the invention can also be used to prognose or predict cancer progression. In particular embodiments, the diagnostic methods of the invention provide methods of imaging and localizing metastases and methods of diagnosis and prognosis using tissues and fluids distal to the primary tumor site (as well as methods using tissues and fluids of the primary tumor). In other embodiments, the diagnostic methods of the invention provide methods of imaging and localizing metastases and methods of diagnosis and prognosis in vivo.

5.1. Epitope of the uPAR-Specific Monoclonal Antibody ATN-658

The present inventors have mapped an epitope on uPAR that is not involved in binding to uPA. This epitope has been mapped by its interaction with the uPAR monoclonal antibody ATN-658, described in WO 2005/116077, incorporated by reference in its entirety. The variable region sequences of ATN-658 are set forth below:

ATN-658: Variable Region Sequences

The consensus amino acid sequence (single-letter code) of the light chain variable region ($V_L$) and heavy chain variable region ($V_H$) polypeptides of monoclonal antibody ATN-658 are shown below. The complementarity-determining regions (CDRs) for each variable region are highlighted (italic, bold, underscored)

```
ATN-658 V_L Consensus Protein (SEQ ID NO: 1):
DVVMTQTPLT LSVTIGQPAS ISC KSSQSLL DSDGKTYL NW
LLQRPGQSPK RLIY LVSKLD SG VPDRFTGS GSGTDFTLKI
SRVEAEDLGV YYC WQGTHFP LT FGAGTKLE LKRADAAPTV
SIFPPSSEQL TSGGASVVCF L ATN-658 V_H Consensus Protein (SEQ ID NO: 2)
EVQLQQSGPE LVKTGASVKI SCKAS GYSFT SYYMH WVKQS
HGKSLEWIG E INPYNGGA SY NQKIKG RATF TVDTSSRTAY
MQFNSLTSED SAVYYCAR SI YGHSVLDY WG QGTSVSVSSA
KTTPPSVYPL APGSAAQTNS M
```

TABLE 1

Characteristics of CDRs of ATN-658 L and H Chains

| CDR* | No. of residues | Sequence[1] | SEQ ID NO: |
|---|---|---|---|
| CDR L1 | 16 | KSSQSLLDSDGKTYLN | 3 |
| CDR L2 | 7 | LVSKLDS | 4 |
| CDR L3 | 9 | WQGTHFPLT | 5 |
| CDR H1 | 10 | GYSFTSYYMH | 6 |
| CDR H2 | 17 | EINPYNGGASYNQKIKG | 7 |
| CDR H3 | 10 | SIYGHSVLDY | 8 |

*CDR-L1: first CDR of L chain; CDR-H2: 2nd CDR of H chain, etc.

This antibody recognizes the uPA-uPAR complex.

This antibody was generated against an epitope in the uPAR D2D3 fragment. An epitope in D2D3 has been demonstrated to be critical to the pro-migratory activity of uPA (Andolfo A et al. (2002) Thromb Haemost 88: 298-306). Thus, antibodies generated against the D2D3 fragment where this epitope is already exposed, are expected to have anti-migratory activity.

TABLE 2 uPAR epitope sequences

| Sequence | Amino acids of Human uPAR[1] | SEQ ID NO: |
|---|---|---|
| CCTKSGCNHPDLDVQYRSG | 265-283 | 9 |
| CCTKSGCNHPDLDVQYRS | 265-282 | 10 |
| CCTKSGCNHPDLDVQYR | 265-281 | 11 |
| CCTKSGCNHPDLDVQY | 265-280 | 12 |
| CCTKSGCNHPDLDVQ | 265-279 | 13 |
| CGSSDMSCERGRHQSL | 98-114 | 14 |
| KSGCNHPDLD | 268-277 | 16 |

[1]The amino acid numbering reflects the processed form of uPAR

In one embodiment, the antibody of the invention recognizes an epitope defined by the amino acid sequence of SEQ ID NO: 9, 10, 11, 12, 13, or 16.

In an alternative embodiment, the antibody of the invention recognizes a conformation-dependent epitope defined by (i) an amino acid sequence of SEQ ID NO: 9, 10, 11, 12, 13, or 16; and (ii) an amino acid sequence of SEQ ID NO: 14 within the context of human uPAR (SEQ ID NO: 15). In this case, full-length soluble uPAR (suPAR) (residues 1-283, domains 1, 2, and 3) can be used as an immunogen. However, one of skill in the art will recognize that shorter fragment of suPAR can be used as an immunogen as long as the proper conformation is maintained.

In some aspects, a conformation-dependent epitope comprises or consists of contiguous amino acid sequences of a fragment of human uPAR from position 98 to 277, 279, 280, 281, 282, or 283. In another aspect, a conformation-dependent epitope comprises or consists of an isolated fragment of human uPAR (SEQ ID NO: 15), in which the amino terminus of said fragment is at any one of amino acid numbers 93-98 and the carboxy terminus of said fragment is at any one of amino acids 277-283, or a derivative thereof containing only conservative substitutions relative to the sequence of said fragment. Fusion proteins comprising such a fragment and a sequence of a different protein are also provided. In a preferred aspect, the conformation-dependent epitope retains its native conformation, as shown, e.g., by molecular modeling. In other aspects, the conformation-dependent epitope is defined by (i) an amino acid sequence of SEQ ID NO: 9, 10, 11, 12, 13, or 16; and (ii) an amino acid sequence of SEQ ID NO: 14, wherein a linker peptide sequence is placed in between the amino acid sequences of (i) and (ii), such that the native conformation is maintained. In a specific embodiment, the linker peptide sequence mimics the native conformation of uPAR. In one embodiment, the linker peptide sequence is heterologous to human uPAR. In another embodiment, the linker peptide sequence is the intervening sequence of human uPAR in which conservative amino acid substitutions have been made. For example, one or more amino acid residues within the sequence can be substituted by another amino acid of a similar polarity which acts as a functional equivalent, resulting in a silent alteration. Substitutions for an amino acid within the sequence may be selected from other members of the class to which the amino acid belongs. For example, the nonpolar (hydrophobic) amino acids include alanine, leucine, isoleucine, valine, proline, phenylalanine, tryptophan and methionine. The polar neutral amino acids include glycine, serine, threonine, cysteine, tyrosine, asparagine, and glutamine. The positively charged (basic) amino acids include arginine, lysine and histidine. The negatively charged (acidic) amino acids include aspartic acid and glutamic acid. Such substitutions are generally understood to be conservative substitutions. Conservative substitutions of one or more amino acid residues are preferably introduced into the peptide sequence at sites that will not disturb the native conformation or activity.

Longer peptides comprising these uPAR epitopes are also contemplated by the present invention. For example, the uPAR peptides may comprise up to 20, 30, 40, 50, 60, 70, 80, 90, 100, 125, 200 amino acids. In one embodiment, the peptides comprise contiguous amino acid residues of uPAR. These longer peptides generally will consist of a fragment of human uPAR and comprise the epitope sequence of uPAR. In another embodiment, the uPAR is human uPAR.

The amino acid sequence of the unprocessed form of human uPAR UniProtKB/Swiss-Prot Accession No. Q03405 (SEQ ID NO: 15) is provided in FIG. 1.

The processed (mature) form of human uPAR removes the first 22 amino acids. C-terminal residues 284-313 (numbered from the amino terminus of the mature protein) are also removed by post-translational processing when uPAR is anchored to the plasma membrane by a GPI tail (see Moller et al., *Eur. J. Biochem.* 208:493-500 (1992); Low, M. G., *FASEB J.* 3:1600-1608 (1989)). Reference to uPAR (including suPAR) in this application is reference to processed (mature) uPAR (containing amino acids 1-283) unless explicitly indicated otherwise.

In some embodiments, mutating one or more amino acid residues of the epitope sequences in Table 2 reduces or abolishes the immunospecific binding affinity of the antibody, e.g., ATN-658, to the epitope, e.g., as contained in human uPAR, which can be membrane-associated or suPAR. In a particular embodiment, a mutation at amino acid residue 268 of human uPAR or the epitopes in Table 2 reduces or abolishes the immunospecific binding affinity of the antibody or antigen-binding fragments thereof to the epitope. In a specific embodiment, binding of an antibody to the epitope is demonstrated by reduction in said binding by said antibody when the K (Lys) residue at position 268 in human uPAR is mutated to a E (Glu) residue (uPAR K268E) or an A (Ala) residue (uPAR K268A). In another embodiment, a mutation at amino acid residue 273 of human uPAR or the epitopes in Table 2 reduces or abolishes the immunospecific binding affinity of the antibody or antigen-binding fragments thereof to the epitope. In a specific embodiment, binding of an antibody to the epitope is demonstrated by reduction in said binding by said antibody when the H (His) residue at position 273 in human uPAR is mutated to an A (Ala) residue (uPAR H273A). In a certain embodiment, a mutation at amino acid residue 275 of human uPAR or the epitopes in Table 2 reduces or abolishes the immunospecific binding affinity of the antibody or antigen-binding fragments thereof to the epitope. In a specific embodiment, binding of an antibody to the epitope is demonstrated by reduction in said binding by said antibody when the D (Asp) residue at position 275 in human uPAR is mutated to an A (Ala) residue (uPAR D275A). In one embodiment, a mutation at amino acid residue 277 of human uPAR or the epitopes in Table 2 reduces or abolishes the immunospecific binding affinity of the antibody or antigen-binding fragments thereof to the epitope. In a specific embodiment, binding of an antibody to the epitope is demonstrated by reduction in said binding by said antibody when the D (Asp) residue at position 277 in human uPAR is mutated to an A (Ala) residue (uPAR D277A). In specific embodiments, a mutation of one or more residues of human uPAR, e.g., 268, 273, 275, and/or 277, e.g., as described herein, or a mutation in any of the epitopes in Table 2 reduces the immunospecific binding affinity of the antibody or an antigen-binding fragment thereof by at least 5%, at least 10%, at least 20%, at least 30%, at least 40% or at least 50% relative to the affinity of the antibody to a wild-type human uPAR (e.g., membrane-bound uPAR, suPAR) or to a fragment of suPAR (e.g., D2D3 suPAR).

The binding affinity of the antibody or antigen-binding fragment thereof to human uPAR or to a fragment (e.g., D2D3 suPAR) containing an epitope thereof can be determined by methods well known in the art, e.g., but not limited to co-immunoprecipitation assays, BIAcore assay, deuterium exchange assay, and ELISA. In a particular embodiment, binding of an antibody to the epitope is demonstrated by a reduction of at least 10%, 20%, 30%, 40%, 50%, 60%, or 70% in said binding by said antibody when the K (Lys) residue at position 268 in human uPAR is mutated to a E (Glu) residue (uPAR K268E) or an A (Ala) residue (uPAR K268A). Preferably, the amount of binding is demonstrated by co-immunoprecipitation of the antibody and uPAR K268E or uPAR K268A, respectively. In certain embodiments, binding of an antibody to the epitope is demonstrated by a reduction of at least 10%, 20%, 30%, 40%, 50%, 60%, 70%, 80% or 90% in said binding by said antibody when the H (His) residue at position 273 in human uPAR is mutated to an A (Ala) residue (uPAR H273A). Preferably, the amount of binding is demonstrated by co-immunoprecipitation of the antibody and uPAR H273A. In other embodiments, binding of an antibody to the epitope is demonstrated by a reduction of at least 10%, 20%, 30%, 40%, 50%, 60%, 70%, 80% or 90% in said binding by said antibody when the D (Asp) residue at position 275 or 277 in human uPAR is mutated to an A (Ala) residue (uPAR D275A or uPAR D277A, respectively). Preferably, the amount of binding is as demonstrated by co-immunoprecipitation of the antibody and uPAR D275A or uPAR D277A, respectively. For example, a reduction in binding by the antibody is demonstrated by a decreased amount of mutated uPAR (e.g., uPAR K268E, uPAR K268A, uPAR H273A, uPAR D275A, or uPAR D277A) that co-immunoprecipitates with the antibody relative to the amount of wild-type uPAR (e.g., membrane-bound uPAR, suPAR) or a fragment of suPAR (e.g., D2D3 suPAR) that co-immunoprecipitates with the antibody.

In other aspects of the invention, the binding of the antibody to an epitope of the invention is demonstrated by a deuterium exchange assay, wherein the binding of an antibody (e.g., ATN-658) to an epitope of a protein (e.g., human suPAR) decreases the ability of that epitope to exchange deuterium. In particular embodiments, human suPAR is contacted with an antibody, and binding of the antibody to an epitope of human uPAR is demonstrated by a reduction in deuteration level over the epitope when in the presence of the antibody, under binding conditions, relative to deuteration over the epitope in the absence of the antibody. Conversely, a region of suPAR that is not contacted by the antibody possesses the same or similar deuteration level when in the presence or absence of the antibody under binding conditions. Preferably, the deuteration assay is performed with a fragment of human uPAR containing, or consisting of, domains 2 and 3 (D2D3) (amino acids 88-283). In specific embodiments, binding of the antibody to an epitope of human suPAR is demonstrated by reduction in deuteration level over the epitope of human suPAR, when in the presence of the antibody under binding conditions, of at least 10%, or at least 20%, or at least 30%, or at least 40%, or at least 50%, relative to deuteration level over the epitope in the absence of the antibody. In particular embodiments, reduction in deuteration level of at least 10%, at least 20%, at least 30%, at least 40%, at least 50%, at least 55%, at least 60%, at least 65%, at least 70%, or at least 75% over the epitope of suPAR is demonstrated when in the presence of the antibody under binding conditions, relative to deuteration level over the epitope of suPAR in the absence of the antibody. In a particular embodiment, the antibody is immobilized.

The uPAR epitope and peptides comprising these sequences may have utility in the diagnostic and therapeutic methods described herein.

5.2. uPAR Antibodies

This invention provides an isolated antibody, or antigen-binding fragment thereof, that immunospecifically binds to an epitope of uPAR defined by the amino acid sequence of SEQ ID NO: 9, 10, 11, 12 or 13. The invention also provides an isolated antibody, or antigen-binding fragment thereof, that immunospecifically binds to a conformation-dependent epitope defined by (i) CCTKSGCNHPDLDVQYRSG (SEQ ID NO: 9), CCTKSGCNHPDLDVQYRS (SEQ ID NO: 10), CCTKSGCNHPDLDVQYR (SEQ ID NO: 11), CCTKSGCNHPDLDVQY (SEQ ID NO: 12) or CCTKSGCNHPDLDVQ (SEQ ID NO: 13); and (ii) CGSSDMSCERGRHQSL (SEQ ID NO: 14) within the context of a human uPAR (SEQ ID NO: 15). This invention provides an isolated antibody, or antigen-binding fragment thereof, that immunospecifically binds to an epitope of uPAR defined by the amino acid sequence of SEQ ID NO: 16. The invention also provides an isolated antibody, or antigen-binding fragment thereof, that immunospecifically binds to a conformation-dependent epitope defined by (i) KSGCNHPDLD (SEQ ID NO: 16); and (ii) CGSSDMSCERGRHQSL (SEQ ID NO: 14) within the context of a human uPAR (SEQ ID NO: 15).

It is believed that these antibodies bind to a binary uPA-uPAR complex, but not substantially to (a) free uPA or (b) the region of uPAR that recognizes and binds to uPA, so that the mAb does not inhibit uPA-uPAR binding. As used herein, "immunospecifically binds" means that the antibody, or an antigen-binding fragment thereof, binds to the antigen via its antigen-recognition region of its variable domain.

5.2.1. Production of Monoclonal Antibodies Using Epitopes

Methods for producing and screening for specific antibodies using hybridoma technology are routine and well known in the art, for example, in Harlow et al., *Antibodies: A Laboratory Manual*, (Cold Spring Harbor Laboratory Press, 2nd ed. 1988); Hammerling, et al., in: *Monoclonal Antibodies and T-Cell Hybridomas* 563-681 (Elsevier, N.Y., 1981), Kohler and Milstein, Nature 256: 495-497 (1975); U.S. Pat. No. 4,376,110; Monoclonal Antibodies and Hybridomas: A New Dimension in Biological Analyses, Plenum Press, New York, N.Y. (1980); H. Zola et al., in Monoclonal Hybridoma Antibodies: Techniques and Applications, CRC Press, 1982) (said references incorporated by reference in their entireties). An animal, preferably a mouse is primed by immunization with an immunogen as above to elicit the desired antibody response in the primed animal. In other embodiments, a non-human mammal is primed by immunization with an immunogen as described above to elicit the desired antibody response in the primed non-human mammal.

Briefly, mice can be immunized with a uPAR epitope and once an immune response is detected, e.g., antibodies specific for uPAR are detected in the mouse serum, the mouse spleen is harvested and splenocytes isolated. The splenocytes are then fused by well known techniques to any suitable myeloma cells, for example cells from cell line SP20 available from the ATCC. Hybridomas are selected and cloned by limited dilution. Hybridoma clones are then assayed by methods known in the art for cells that secrete antibodies capable of binding uPAR. Ascites fluid, which generally contains high levels of antibodies, can be generated by immunizing mice with positive hybridoma clones.

The epitope sequences in Table 2 are used as an immunogen for the generation of the antibodies of the invention. In one embodiment, a peptide consisting of the amino acid sequence CCTKSGCNHPDLDVQYRSG (SEQ ID NO: 9), CCTKSGCNHPDLDVQYRS (SEQ ID NO: 10), CCTKSGCNHPDLDVQYR (SEQ ID NO: 11), CCTKSGCNHPDLDVQY (SEQ ID NO: 12), CCTKSGCNHPDLDVQ (SEQ ID NO: 13), KSGCNHPDLD (SEQ ID NO: 16) or CGSSDMSCERGRHQSL (SEQ ID NO: 14) is used. In another embodiment, a fragment of human uPAR, of up to 20, 30, 40, 50, 60 or 100 amino acids, comprising the amino acid sequence CCTKSGCNHPDLDVQYRSG (SEQ ID NO: 9), CCTKSGCNHPDLDVQYRS (SEQ ID NO: 10), CCTKSGCNHPDLDVQYR (SEQ ID NO: 11), CCTKSGCNHPDLDVQY (SEQ ID NO: 12), CCTKSGCNHPDLDVQ (SEQ ID NO: 13) or CGSSDMSCERGRHQSL (SEQ ID NO: 14), is used. In one embodiment, a fragment of human uPAR, of up to 20, 30, 40, 50, 60 or 100 amino acids, comprising the amino acid sequence KSGCNHPDLD (SEQ ID NO: 16), is used. In yet another embodiment, a peptide comprising a conformation-dependent epitope defined by (i) CCTKSGCNHPDLDVQYRSG (SEQ ID NO: 9), CCTKSGCNHPDLDVQYRS (SEQ ID NO: 10), CCTKSGCNHPDLDVQYP (SEQ ID NO: 11), CCTKSGCNHPDLDVQY (SEQ ID NO: 12) or CCTKSGCNHPDLDVQ (SEQ ID NO: 13); and (ii) CGSSDMSCERGRHQSL (SEQ ID NO: 14) within the context of a human uPAR (SEQ ID NO: 15) is used. In a particular embodiment, a peptide comprising or alternatively, consisting of, a conformation-dependent epitope defined by (i)

KSGCNHPDLD (SEQ ID NO: 16); and (ii) CGSSDMSCER-GRHQSL (SEQ ID NO: 14) of a human uPAR (SEQ ID NO: 15) is used.

In some aspects, such a conformation-dependent epitope comprises or consists of contiguous amino acid sequences of a fragment of human uPAR from position 98 to 277, 279, 280, 281, 282, or 283. In a preferred aspect, the conformation-dependent epitope retains its native conformation, as shown, e.g., by molecular modeling. In other aspects, the conformation-dependent epitope is defined by (i) an amino acid sequence of SEQ ID NO: 9, 10, 11, 12, 13, or 16; and (ii) an amino acid sequence of SEQ ID NO: 14, wherein a linker peptide sequence is placed in between the amino acid sequences of (i) and (ii), such that the native conformation is maintained. In a specific embodiment, the linker peptide sequence mimics the native conformation of uPAR. In one embodiment, the linker peptide sequence is heterologous to human uPAR. In another embodiment, the linker peptide sequence is the intervening sequence of human uPAR in which conservative amino acid substitutions have been made. Conservative substitutions of one or more amino acid residues are preferably introduced into the peptide sequence at sites that will not disturb the native conformation or activity. For example, one or more amino acid residues within the sequence can be substituted by another amino acid of a similar polarity which acts as a functional equivalent, resulting in a silent alteration. Substitutions for an amino acid within the sequence may be selected from other members of the class to which the amino acid belongs. For example, the nonpolar (hydrophobic) amino acids include alanine, leucine, isoleucine, valine, proline, phenylalanine, tryptophan and methionine. The polar neutral amino acids include glycine, serine, threonine, cysteine, tyrosine, asparagine, and glutamine. The positively charged (basic) amino acids include arginine, lysine and histidine. The negatively charged (acidic) amino acids include aspartic acid and glutamic acid. Such substitutions are generally understood to be conservative substitutions.

In other embodiments, a peptide or fragment of human uPAR comprising or consisting of domains 2 and 3 (D2D3) corresponding to residues 88-283 of soluble uPAR (suPAR) is used as the immunogen. Peptides comprising these sequences can be produced in a variety of ways known in the art, e.g., expression of cloned genes using conventional recombinant methods, isolation from cells of origin, cell populations expressing high levels of e.g., uPA or uPAR, etc. In the case of shorter fragments, they may be chemically synthesized.

B lymphocytes from the lymph nodes, spleens or peripheral blood of a primed, animal are fused with myeloma cells, generally in the presence of a fusion promoting agent such as polyethylene glycol (PEG). Any of a number of murine myeloma cell lines are available for such use: the P3-NS1/1-Ag4-1, P3-x63-k0Ag8.653, Sp2/0-Ag14, or HL1-653 myeloma lines (available from the ATCC, Rockville, Md.). Subsequent steps include growth in selective medium so that unfused parental myeloma cells and donor lymphocyte cells eventually die while only the hybridoma cells survive. These are cloned and grown and their supernatants screened for the presence of Ab of the desired specificity, e.g., by immunoassay techniques. Positive clones are subcloned, e.g., by limiting dilution, and the monoclonal antibodies are isolated.

Hybridomas produced according to these methods can be propagated in vitro or in vivo (in ascites fluid) using techniques known in the art (see generally Fink et al., Prog. Clin. Pathol. 9:121-33 (1984)). Generally, the individual cell line is propagated in culture and the culture medium containing high concentrations of a single monoclonal antibody can be harvested by decantation, filtration, or centrifugation.

A preferred approach for producing a mAb according to the present invention is as follows.

An epitope in table 2 is preferably conjugated to a carrier protein, e.g., KLH, is and injected into BALB/c mice intraperitoneally (i.p.) in complete Freund's adjuvant (e.g., 50 µg conjugate), followed by two additional injections of the same dose in incomplete Freund's adjuvant at two week intervals. After one month, a final injection is given i.p (e.g., 50 µg in 0.5 ml PBS) and preferably also intravenously (i.v.) (e.g., 50 µg in 0.2 ml) without adjuvant.

Spleen cells are harvested three days after the final injection and fused with P3X63AF8/653 or other myeloma cells using standard techniques.

Following immunization using standard protocols, conventional techniques are employed to generate hybridoma cell lines from the immunized animals and to generate monoclonal antibodies having the desired properties.

5.3. Screening and Characterization of uPAR Antibodies

Pure suPAR immobilized onto plastic is preferred for the primary screening. Many tumor cell lines overexpressing uPAR are well-known and publicly available; these may be used for screening. For example, cells such as the HeLa line that overexpress uPAR may also be used to demonstrate cell binding of an anti-uPAR mAb. Cells are generally plated in 96-well microplates. The cells may be fixed, e.g., with methanol/acetone (50/50), and the binding detected by immunofluorescence staining. Alternatively, the mAbs may be labeled, using radioactive isotopes or other tracers such as biotin, and binding detected by measurement of radioactivity or biotin.

In one embodiment, a hybridoma supernatant (e.g., 50 µl) is added to wells containing fixed 293 cells for about 1.5 h at 37° C. Plates are washed twice in washing buffer (such as PBS/0.05% Tween-20), and Rhodamine Red-conjugated goat anti-mouse IgG is added (e.g., 30 µl/well) at an appropriate dilution, such as 1:100, for 1.5 h at 37° C. After washing in a washing buffer, cells are examined for the presence of immunofluorescence; in the embodiment described here, fluorescence microscopy is used.

In this embodiment, immunofluorescence is the basis for determining whether a hybridoma supernatant contains an antibody specific for the uPA/uPAR complex (although immunohistochemical staining may also be used). If supernatants show positively staining the hybridoma clones are selected, expanded and the supernatants tested for reactivity to the complex by ELISA.

In a preferred ELISA, the peptide is coupled to ovalbumin (OVA) as a carrier protein and the peptide/OVA conjugate coated onto wells of 96 well EIA plate which receives, for example, 2 µg/ml of conjugate in 50 µl coating buffer (0.2 M $Na_2CO_3$/$NaHCO_3$, pH 9.6). Plates are incubated overnight at 4° C., blocked with an appropriate blocking buffer, e.g., PBS containing 1% BSA (200 µl/well) overnight at 4° C. Hybridoma supernatants (e.g., 50 µl) are added to wells for 1.5 hours at room temperature.

Plates are washed twice in washing buffer (e.g., PBS/0.05% Tween-20), and enzyme-coupled secondary Ab, such as alkaline phosphatase-coupled goat-anti-mouse IgG is added (50 µl/well) at an appropriate dilution, e.g., 1:2000. Plates are incubated for 1.5 hours at RT. After washing 4× in washing buffer, an appropriate chromogenic substrate for the enzyme, e.g., CP-nitrophenylphosphate in this embodiment (available from Kirkegaard and Perry Co., Gaithersburg, Md.), is added for about 30 min and absorbance measured at wavelength appropriate for the colored product (here 405 nm). Hybridoma supernatants that react strong with the epitope-bearing peptide (e.g., $A_{405}>1.0$ when negative controls are <0.02) are re-cloned (preferably twice), and the mAb reactivity again confirmed by ELISA as above.

The anti-uPAR antibodies of the invention are preferably tested in xenogeneic tumor models, two preferred examples of which are the A2780 and A549 models (described in more detail below).

The antibodies are evaluated for direct anti-angiogenic activity in an in vivo Matrigel plug model. Radioiodinated antibodies are used to test antibody internalization using MDA MB 231 cells which express both receptor and ligand. Antibody internalization is also measured in the presence of PAI-1: uPA complexes.

5.4. Antibody Forms

Antibodies used in the methods of the invention include, but are not limited to, monoclonal antibodies, synthetic antibodies, multispecific antibodies (including bi-specific antibodies), human antibodies, humanized antibodies, chimeric antibodies, single-chain Fvs (scFv) (including bi-specific scFvs), single chain antibodies, Fab fragments, F(ab') fragments, disulfide-linked Fvs (sdFv), and epitope-binding fragments of any of the above. In particular, antibodies used in the methods of the present invention include immunoglobulin molecules and immunologically active portions of immunoglobulin molecules, i.e., molecules that contain an antigen binding site that immunospecifically binds to uPAR. The immunoglobulin molecules of the invention can be of any type (e.g., IgG, IgE, IgM, IgD, IgA and IgY), class (e.g., $IgG_1$, $IgG_2$, $IgG_3$, $IgG_4$, IgA, and $IgA_2$) or subclass of immunoglobulin molecule. Anti-idiotypic antibodies specific for the idiotype of, for example, an anti-uPA/uPAR antibody are also included.

Antibody derivatives are also encompassed by the invention. The term "derivative" as used herein refers to a polypeptide that comprises an amino acid sequence of an antibody that immunospecifically binds to an uPAR polypeptide, or an antibody fragment that immunospecifically binds to an uPAR polypeptide, which has been altered by the introduction of amino acid residue substitutions, deletions or additions (i.e., mutations). In some embodiments, an antibody derivative or fragment thereof comprises amino acid residue substitutions, deletions or additions in one or more CDRs. The antibody derivative may have substantially the same binding, better binding, or worse binding when compared to a non-derivative antibody. In specific embodiments, one, two, three, four, or five amino acid residues of the CDR have been substituted, deleted or added (i.e., mutated). The term "derivative" as used herein also refers to an antibody that immunospecifically binds to uPAR, or an antibody fragment that immunospecifically binds to an uPAR, which has been modified, i.e, by the covalent attachment of any type of molecule to the polypeptide. For example, but not by way of limitation, an uPAR antibody, or antibody fragment may be modified, e.g., by glycosylation, acetylation, pegylation, phosphorylation, amidation, derivatization by known protecting/blocking groups, proteolytic cleavage, linkage to a cellular ligand or other protein, etc. A derivative of an uPAR antibody, or antibody fragment, may be modified by chemical modifications using techniques known to those of skill in the art, including, but not limited to specific chemical cleavage, acetylation, formylation, metabolic synthesis of tunicamycin, etc. Further, a derivative of an uPAR antibody, or antibody fragment, may contain one or more non-classical amino acids.

The antibodies used in the methods of the invention may be from any animal origin including birds and mammals (e.g., human, murine, donkey, sheep, rabbit, goat, guinea pig, camel, horse, or chicken). In a specific embodiment, the methods of the invention may be from a non-human mammal. Preferably, the antibodies are human or humanized monoclonal antibodies. As used herein, "human" antibodies include antibodies having the amino acid sequence of a human immunoglobulin and include antibodies isolated from human immunoglobulin libraries or from mice or other animal that express antibodies from human genes.

The antibodies used in the methods of the present invention may be monospecific, bispecific, tri specific or of greater multispecificity. Multi specific antibodies may immunospecifically bind to different epitopes of uPAR or may immunospecifically bind to both uPAR as well a heterologous epitope, such as a heterologous polypeptide or solid support material. See, e.g., International Publication Nos. WO 93/17715, WO 92/08802, WO 91/00360, and WO 92/05793; Tutt, et al., 1991, *J. Immunol.* 147:60-69; U.S. Pat. Nos. 4,474,893, 4,714,681, 4,925,648, 5,573,920, and 5,601,819; and Kostelny et al., 1992, *J. Immunol.* 148:1547-1553. In certain embodiments of the invention, a bispecific antibody which binds to the epitope of ATN-658 and another uPAR epitope. See Gardsvoll et al., 2006, *J. Biol. Chem.* 281(28):19260-72; Gardsvoll et al., 1999, *J. Biol. Chem.* 274(53):37995-8003.

Antibodies of the present invention can also be generated using various phage display methods known in the art. In phage display methods, functional antibody domains are displayed on the surface of phage particles which carry the polynucleotide sequences encoding them. In particular, DNA sequences encoding $V_H$ and $V_L$ domains are amplified from animal cDNA libraries (e.g., human or murine cDNA libraries of lymphoid tissues). The DNA encoding the $V_H$ and $V_L$ domains are recombined together with an scFv linker by PCR and cloned into a phagemid vector (e.g., p CANTAB 6 or pComb 3 HSS). The vector is electroporated in *E. coli* and the *E. coli* is infected with helper phage. Phage used in these methods are typically filamentous phage including fd and M13 and the $V_H$ and $V_L$ domains are usually recombinantly fused to either the phage gene III or gene VIII. Phage expressing an antigen binding domain that binds to the uPAR epitope of interest can be selected or identified with antigen, e.g., using labeled antigen or antigen bound or captured to a solid surface or bead. Examples of phage display methods that can be used to make the antibodies of the present invention include those disclosed in Brinkman et al., 1995, *J. Immunol. Methods* 182:41-50; Ames et al., 1995, *J. Immunol. Methods* 184:177; Kettleborough et al., 1994, *Eur. J. Immunol.* 24:952-958; Persic et al., 1997, *Gene* 187:9; Burton et al., 1994, *Advances in Immunology* 57:191-280; International Application No. PCT/GB91/01134; International Publication Nos. WO 90/02809, WO 91/10737, WO 92/01047, WO 92/18619, WO 93/11236, WO 95/15982, WO 95/20401, and WO97/13844; and U.S. Pat. Nos. 5,698,426, 5,223,409, 5,403,484, 5,580,717, 5,427,908, 5,750,753, 5,821,047, 5,571,698, 5,427,908, 5,516,637, 5,780,225, 5,658,727, 5,733,743 and 5,969,108; each of which is incorporated herein by reference in its entirety.

As described in the above references, after phage selection, the antibody coding regions from the phage can be isolated and used to generate whole antibodies, including human antibodies, or any other desired antigen binding fragment, and expressed in any desired host, including mammalian cells, insect cells, plant cells, yeast, and bacteria, e.g., as described below. Techniques to recombinantly produce Fab, Fab' and F(ab')2 fragments can also be employed using methods known in the art such as those disclosed in International Publication No. WO 92/22324; Mullinax et al., 1992, *BioTechniques* 12:864; Sawai et al., 1995, *AJRI* 34:26; and Better et al., 1988, Science 240:1041 (said references incorporated by reference in their entireties).

To generate whole antibodies, PCR primers including $V_H$ or $V_L$ nucleotide sequences, a restriction site, and a flanking sequence to protect the restriction site can be used to amplify the $V_H$ or $V_L$ sequences in scFv clones. Utilizing cloning techniques known to those of skill in the art, the PCR amplified $V_H$ domains can be cloned into vectors expressing a $V_H$ constant region, e.g., the human gamma 4 constant region, and the PCR amplified $V_L$ domains can be cloned into vectors expressing a $V_L$ constant region, e.g., human kappa or lambda constant regions. The $V_H$ and $V_L$ domains may also be cloned into one vector expressing the necessary constant regions. The heavy chain conversion vectors and light chain conversion vectors are then co-transfected into cell lines to generate stable or transient cell lines that express full-length antibodies, e.g., IgG, using techniques known to those of skill in the art.

5.4.1. Antibody Fragments

The term "antibody" is meant to include both intact immunoglobulin (Ig) molecules as well as fragments and derivative thereof, that may be produced by proteolytic cleavage of Ig molecules or engineered genetically or chemically. Fragments include, for example, Fab, Fab', F(ab')2 and Fv, each of which is capable of binding antigen. The "fragments" described herein include a peptide or polypeptide comprising an amino acid sequence of at least 5 contiguous amino acid residues, at least 10 contiguous amino acid residues, at least 15 contiguous amino acid residues, at least 20 contiguous amino acid residues, at least 25 contiguous amino acid residues, at least 40 contiguous amino acid residues, at least 50 contiguous amino acid residues, at least 60 contiguous amino acid residues, at least 70 contiguous amino acid residues, at least contiguous 80 amino acid residues, at least contiguous 90 amino acid residues, at least contiguous 100 amino acid residues, at least contiguous 125 amino acid residues, at least 150 contiguous amino acid residues, at least contiguous 175 amino acid residues, at least contiguous 200 amino acid residues, or at least contiguous 250 amino acid residues of the amino acid sequence of an antibody that immunospecifically binds to uPAR polypeptide. Preferably, antibody fragments are epitope-binding fragments.

A Fab fragment is a multimeric protein consisting of the portion of an Ig molecule containing the immunologically active portions of an Ig heavy (H) chain and an Ig light (L) chain covalently coupled together and capable of specifically combining with antigen. A (Fab') 2 fragment is a tetramer that includes a fragment of two H and two L chains. The Fv fragment is a multimeric protein consisting of the immunologically active portions of an Ig H chain variable (V) region (VH) and an Ig L chain V region (VL) covalently coupled together and capable of specifically combining with antigen. These fragments lack the Fc fragment of intact Ab and have an additional advantage, if used therapeutically, of clearing more rapidly from the circulation and undergoing less non-specific tissue binding than intact antibodies. These various fragments are produced using conventional techniques such as protease cleavage or chemical cleavage (see, e.g., Rousseaux et al., *Meth. Enzymol.*, 121:663-69 (1986)). For example, papain treatment of Ig's produces Fab fragments; pepsin treatment produces F(ab')2 fragments. These fragments may also produced by genetic or protein engineering using methods well known in the art. For example, a Fab fragment may also be prepared by expressing in a suitable host cell the desired portions of Ig H chain and L chain using methods well known in the art. Fv fragments are typically prepared by expressing in suitable host cell the desired portions of Ig VH region and VL region using methods well known in the art.

5.4.2. Single Chain Antibodies

The antibodies of the present invention may be produced as a single chain antibody or scFv instead of the normal multimeric structure. Single-chain antigen-binding protein or single chain Ab, also referred to as "scFv," is a polypeptide composed of an Ig VL amino acid sequence tethered to an Ig $V_H$ amino acid sequence by a peptide that links the C-terminus of the $V_L$ sequence to the N-terminus of the $V_H$ sequence. (Skerra, A. et al. (1988) Science, 240: 1038-1041; Pluckthun, A. et al. (1989) Methods Enzymol. 178: 497-515; Winter, G. et al. (1991) Nature, 349: 293-299); Bird et al., (1988) Science 242: 423; Huston et al. (1988) Proc. Natl. Acad. Sci. USA 85: 5879; Jost C R et al., J Biol Chem. 1994 269:26267-26273; U.S. Pat. Nos. 4,704,692; 4,853,871; 4,94,6778; 5,260,203; 5,455,030). DNA sequences encoding the V regions of the H chain and the L chain are ligated to a linker encoding at least about 4 amino acids (typically small neutral amino acids). The protein encoded by this fusion allows assembly of a functional variable region that retains the specificity and affinity of the original antibody. In specific embodiments, scFvs include bispecific scFvs and humanized scFvs.

One method of producing the single chain antibodies is to link two or more peptides or polypeptides together by protein chemistry techniques. For example, peptides or polypeptides can be chemically synthesized using currently available laboratory equipment using either Fmoc (9-fluorenylmethyloxycarbonyl) or tBoc (tert-butyloxycarbonyl) chemistry. (Applied Biosystems, Inc., Foster City, Calif.). One skilled in the art can readily appreciate that a peptide or polypeptide corresponding to an antibody chain or antigen-binding fragment thereof can be synthesized by standard chemical reactions. For example, a peptide or polypeptide can be synthesized but not cleaved from its synthesis resin whereas the other fragment of an Ab can be synthesized and subsequently cleaved from the resin, thereby exposing a terminal group which is functionally blocked on the other fragment. By peptide condensation reactions, these two fragments can be covalently joined via a peptide bond at their C- and N-termini, respectively, to form an Ab, or a fragment thereof. (Grunt, G A, Synthetic Peptides: A User Guide, W. H. Freeman and Co., N.Y. (1992); Bodansky, M et al., eds, Principles of Peptide Synthesis, Springer-Verlag Inc., N.Y. (1993))

Antibodies can be selected for particular desired properties. In the case of an antibody to be used in vivo, Ab screening procedures can include any of the in vitro or in vivo bioassays that measure binding to e.g., uPA/uPAR or uPAR-integrin complex, to cells expressing the relevant polypeptide or peptide epitope.

5.4.3. Chimeric, Humanized and Human Antibodies

For some uses, including in vivo use of antibodies in humans and in vitro detection assays, it may be preferable to use human or chimeric antibodies. Completely human antibodies are particularly desirable for therapeutic treatment of human subjects.

A chimeric antibody is a molecule in which different portions of the antibody are derived from different immunoglobulin molecules. Methods for producing chimeric antibodies are known in the art. See, e.g., Morrison, 1985, *Science* 229: 1202; Oi et al., 1986, *BioTechniques* 4:214; Gillies et al., 1989, *J. Immunol. Methods* 125:191-202; and U.S. Pat. Nos. 6,311,415, 5,807,715, 4,816,567, and 4,816,397, which are incorporated herein by reference in their entirety. Chimeric antibodies comprising one or more CDRs from one species and framework regions from a different species can be produced using a variety of techniques known in the art including, for example, CDR-grafting (EP 239,400; International Publication No. WO 91/09967; and U.S. Pat. Nos. 5,225,539, 5,530,101, and 5,585,089), veneering or resurfacing (EP 592, 106; EP 519,596; Padlan, 1991, *Molecular Immunology* 28(4/5):489-498; Studnicka et al., 1994, *Protein Engineering* 7:805; and Roguska et al., 1994, *PNAS* 91:969), and chain shuffling (U.S. Pat. No. 5,565,332).

Antibodies, fragments or derivatives having chimeric H chains and L chains of the same or different V region binding specificity, can be prepared by appropriate association of the individual polypeptide chains, as taught, for example by Sears et al., Proc. Natl. Acad. Sci. USA 72: 353-357 (1975).

With this approach, hosts expressing chimeric H chains (or their derivatives) are separately cultured from hosts expressing chimeric L chains (or their derivatives), and the Ig chains are separately recovered and then associated. Alternatively, the hosts can be co-cultured and the chains allowed to associate spontaneously in the culture medium, followed by recovery of the assembled Ig, fragment or derivative.

As used herein, the term "chimeric antibody" includes monovalent, divalent or polyvalent Igs. A monovalent chimeric Ab is an HL dimer formed by a chimeric H chain associated through disulfide bridges with a chimeric L chain. A divalent chimeric Ab is tetramer H2L2 formed by two HL dimers associated through at least one disulfide bridge. A polyvalent chimeric Ab can also be produced, for example, by employing a CH region that aggregates (e.g., from an IgM H chain, termed the p chain).

The invention also provides for "derivatives" of the chimeric antibodies, which term includes those proteins encoded by truncated or modified genes to yield molecular species functionally resembling the Ig fragments. The modifications include, but are not limited to, addition of genetic sequences coding for cytotoxic proteins such as plant and bacterial toxins. The fragments and derivatives can be produced from any of the hosts of this invention.

A humanized antibody refers to a non-human (e.g., murine) antibody that is a chimeric antibody which contain minimal sequence derived from non-human immunoglobulin. For the most part, humanized antibodies are human immunoglobulins (recipient antibody) in which hypervariable region residues of the recipient are replaced by hypervariable region residues from a non-human species (donor antibody) such as mouse, rat, rabbit or non-human primate having the desired specificity, affinity, and capacity. A humanized antibody comprises substantially all of at least one, and typically two, variable domains in which all or substantially all of the CDR regions correspond to those of a non-human immunoglobulin (i.e., donor antibody) and all or substantially all of the framework regions are those of a human immunoglobulin consensus sequence. Preferably, a humanized antibody also comprises at least a portion of an immunoglobulin constant region (Fc), typically that of a human immunoglobulin. Ordinarily, the antibody will contain both the light chain as well as at least the variable domain of a heavy chain. The antibody also may include the CH1, hinge, CH2, CH3, and CH4 regions of the heavy chain. The humanized antibody can be selected from any class of immunoglobulins, including IgM, IgG, IgD, IgA and IgE, and any isotype, including $IgG_1$, $IgG_2$, $IgG_3$ and $IgG_4$. Usually the constant domain is a complement fixing constant domain where it is desired that the humanized antibody exhibit cytotoxic activity, and the class is typically $IgG_1$. Where such cytotoxic activity is not desirable, the constant domain may be of the $IgG_2$ class. The humanized antibody may comprise sequences from more than one class or isotype, and selecting particular constant domains to optimize desired effector functions is within the ordinary skill in the art. The framework and CDR regions of a humanized antibody need not correspond precisely to the parental sequences, e.g., the donor CDR or the consensus framework may be mutagenized by substitution, insertion or deletion of at least one residue so that the CDR or framework residue at that site does not correspond to either the consensus or the import antibody. Such mutations, however, will not be extensive. Usually, at least 75% of the humanized antibody residues will correspond to those of the parental framework region (FR) and CDR sequences, more often 90%, and most preferably greater than 95%. Humanized antibodies can be produced using variety of techniques known in the art, including but not limited to, CDR-grafting (European Patent No. EP 239,400; International Publication No. WO 91/09967; and U.S. Pat. Nos. 5,225,539, 5,530,101, and 5,585,089), veneering or resurfacing (European Patent Nos. EP 592,106 and EP 519,596; Padlan, 1991, *Molecular Immunology* 28(4/5):489-498; Studnicka et al., 1994, *Protein Engineering* 7(6):805-814; and Roguska et al., 1994, *PNAS* 91:969-973), chain shuffling (U.S. Pat. No. 5,565,332), and techniques disclosed in, e.g., U.S. Pat. Nos. 6,407,213, 5,766, 886, 5,585,089, International Publication No. WO 9317105, Tan et al., 2002, *J. Immunol.* 169:1119-25, Caldas et al., 2000, *Protein Eng.* 13:353-60, Morea et al., 2000, *Methods* 20:267-79, Baca et al., 1997, *J. Biol. Chem.* 272:10678-84, Roguska et al., 1996, *Protein Eng.* 9:895-904, Couto et al., 1995, *Cancer Res.* 55 (23 Supp):5973s-5977s, Couto et al., 1995, *Cancer Res.* 55:1717-22, Sandhu, 1994, *Gene* 150:409-10, Pedersen et al., 1994, *J. Mol. Biol.* 235:959-73, Jones et al., 1986, *Nature* 321:522-525, Riechmann et al., 1988, *Nature* 332:323, and Presta, 1992, *Curr. Op. Struct. Biol.* 2:593-596. Human antibodies can be made by a variety of methods known in the art including phage display methods described above using antibody libraries derived from human immunoglobulin sequences. See also U.S. Pat. Nos. 4,444,887 and 4,716,111; and International Publication Nos. WO 98/46645, WO 98/50433, WO 98/24893, WO 98/16654, WO 96/34096, WO 96/33735, and WO 91/10741; each of which is incorporated herein by reference in its entirety. Often, framework residues in the framework regions will be substituted with the corresponding residue from the CDR donor antibody to alter, preferably improve, antigen binding. These framework substitutions are identified by methods well known in the art, e.g., by modeling of the interactions of the CDR and framework residues to identify framework residues important for antigen binding and sequence comparison to identify unusual framework residues at particular positions. (See, e.g., Queen et al., U.S. Pat. No. 5,585,089; and Riechmann et al., 1988, *Nature* 332:323, which are incorporated herein by reference in their entireties.)

In one embodiment, a humanized antibody of the invention immunospecifically binds uPAR and comprises one, two, or three $V_L$ CDRs of a uPAR antibody within human framework regions. In another embodiment, a humanized antibody of the invention immunospecifically binds uPAR and comprises one, two, or three $V_H$ CDRs within human framework regions. In a preferred embodiment, a humanized antibody of the invention immunospecifically binds uPAR and comprises one, two, or three $V_L$ CDRs and further comprises one, two, or three $V_H$ CDRs within human framework regions. In a more preferred embodiment, a humanized antibody of the invention immunospecifically binds uPAR and comprises three $V_L$ CDRs and three $V_H$ CDRs having within human framework regions. Often, framework residues in the framework regions will be substituted with the corresponding residue from the CDR donor antibody to alter, preferably improve, antigen binding. These framework substitutions are identified by methods well known in the art, e.g., by modeling of the interactions of the CDR and framework residues to identify framework residues important for antigen binding and sequence comparison to identify unusual framework residues at particular positions. (See, e.g., U.S. Pat. No. 5,585,089; and Riechmann et al., 1988, Nature 332:323, which are incorporated herein by reference in their entireties.)

Thus, in one embodiment of the invention, the chimeric antibodies of the invention comprise individual chimeric H and L Ig chains. The chimeric H chain comprises an antigen binding region derived from the H chain of a non-human Ab specific for e.g., uPA/uPAR or uPAR-integrin complex which is linked to at least a portion of a human $C_H$ region. A chimeric L chain comprises an antigen binding region derived from the L chain of a non-human antibody specific for the target antigen linked to at least a portion of a human $C_L$ region. As used herein, the term "antigen binding region" refers to that portion of an antibody molecule which contains the amino acid residues that interact with an antigen and confer on the antibody its specificity and affinity for the antigen. The antibody region includes the "framework" amino acid residues necessary to maintain the proper conformation of the antigen-binding (or "contact") residues.

Human antibodies are antibodies that are produced using transgenic mice which are incapable of expressing functional endogenous immunoglobulins, but which can express human immunoglobulin genes. For example, the human heavy and light chain immunoglobulin gene complexes may be introduced randomly or by homologous recombination into mouse embryonic stem cells. Alternatively, the human variable region, constant region, and diversity region may be introduced into mouse embryonic stem cells in addition to the human heavy and light chain genes. The mouse heavy and light chain immunoglobulin genes may be rendered non-functional separately or simultaneously with the introduction of human immunoglobulin loci by homologous recombination. In particular, homozygous deletion of the $J_H$ region prevents endogenous antibody production. The modified embryonic stem cells are expanded and microinjected into blastocysts to produce chimeric mice. The chimeric mice are then be bred to produce homozygous offspring which express human antibodies. The transgenic mice are immunized in the normal fashion with a selected antigen, e.g., all or a portion of a polypeptide of the invention. Monoclonal antibodies directed against the antigen can be obtained from the immunized, transgenic mice using conventional hybridoma technology. The human immunoglobulin transgenes harbored by the transgenic mice rearrange during B cell differentiation, and subsequently undergo class switching and somatic mutation. Thus, using such a technique, it is possible to produce therapeutically useful IgG, IgA, IgM and IgE antibodies. For an overview of this technology for producing human antibodies, see Lonberg and Huszar (1995, Int. Rev. Immunol. 13:65-93). For a detailed discussion of this technology for producing human antibodies and human monoclonal antibodies and protocols for producing such antibodies, see, e.g., International Publication Nos. WO 98/24893, WO 96/34096, and WO 96/33735; and U.S. Pat. Nos. 5,413,923, 5,625,126, 5,633,425, 5,569,825, 5,661,016, 5,545,806, 5,814,318, and 5,939,598, which are incorporated by reference herein in their entirety. In addition, companies such as Abgenix, Inc. (Fremont, Calif.) and Medarex (Princeton, N.J.) can be engaged to provide human antibodies directed against a selected antigen using technology similar to that described above.

The antigen binding region of the chimeric antibody (or a human monoclonal antibody) of the present invention is derived preferably from a non-human antibody specific for e.g., uPA/uPAR or uPAR-integrin complex. Preferred sources for the DNA encoding such a non-human antibody include cell lines which produce antibody, preferably hybridomas, e.g., the ATN-658 hybridoma.

Alternatively, the non-human antibody producing cell from which the V region of the Ab of the invention is derived may be a B lymphocyte obtained from the blood, spleen, lymph nodes or other tissue of an animal immunized with D2D3 of suPAR. The Ab-producing cell contributing the nucleotide sequences encoding the antigen-binding region of the chimeric antibody of the present invention may also be produced by transformation of a non-human, such as a primate, or a human cell. For example, a B lymphocyte which produces an antibody specific, e.g., uPA/uPAR or uPAR-integrin complex may be infected and transformed with a virus such as Epstein-Barr virus to yield an immortal Ab producing cell (Kozbor et al. Immunol. Today 4:72-79 (1983)). Alternatively, the B lymphocyte may be transformed by providing a transforming gene or transforming gene product, as is well-known in the art. Preferably, the antigen binding region will be of murine origin. In other embodiments, the antigen binding region may be derived from other animal species, in particular rodents such as rat or hamster.

The chimeric monoclonal antibody of the present invention may be produced in large quantities by injecting hybridoma or transfectoma cells secreting the antibody into the peritoneal cavity of mice and, after appropriate time, harvesting the ascites fluid which contains a high titer of the monoclonal antibody, and isolating the monoclonal antibody therefrom. For such in vivo production of the mAb with a non-murine hybridoma (e.g., rat or human), hybridoma cells are preferably grown in irradiated or athymic nude mice.

Alternatively, the antibodies may be produced by culturing hybridoma (or transfectoma) cells in vitro and isolating secreted mAb from the cell culture medium.

Human genes which encode the constant C regions of the chimeric antibodies of the present invention may be derived from a human fetal liver library or from any human cell including those which express and produce human Igs. The human CH region can be derived from any of the known classes or isotypes of human H chains, including γ, μ, α, δ or ε, and subtypes thereof, such as G1, G2, G3 and G4.

Since the H chain isotype is responsible for the various effector functions of an Ab, the choice of CH region will be guided by the desired effector functions, such as complement fixation, or activity in Ab-dependent cellular cytotoxicity (ADCC). Preferably, the CH region is derived from γ1 (IgG1), γ3 (IgG3), γ4 (IgG4), or μ (IgM).

The human CL region can be derived from either human L chain isotype, κ or λ.

Genes encoding human Ig C regions are obtained from human cells by standard cloning techniques (Sambrook, J. et al., Molecular Cloning: A Laboratory Manual, 2nd Edition, Cold Spring Harbor Press, Cold Spring Harbor, N.Y. (1989)). Human C region genes are readily available from known clones containing genes representing the two classes of L chains, the five classes of H chains and subclasses thereof. Chimeric Ab fragments, such as F(ab')2 and Fab, can be prepared by designing a chimeric H chain gene which is appropriately truncated. For example, a chimeric gene encoding an H chain portion of an F(ab')2 fragment would include DNA sequences encoding the CH, domain and hinge region of the H chain, followed by a translational stop codon to yield the truncated molecule.

Generally, the chimeric antibodies of the present invention are produced by cloning DNA segments encoding the H and L chain antigen-binding regions of a specific antibody of the invention, preferably non-human, and joining these DNA segments to DNA segments encoding human CH and CL regions, respectively, to produce chimeric Ig-encoding genes.

Thus, in a preferred embodiment, a fused gene is created which comprises a first DNA segment that encodes at least the antigen-binding region of non-human origin, such as a functionally rearranged V region with joining (J) segment, linked to a second DNA segment encoding at least a part of a human C region.

The DNA encoding the Ab-binding region may be genomic DNA or cDNA. A convenient alternative to the use of chromosomal gene fragments as the source of DNA encoding the murine V region antigen-binding segment is the use of cDNA for the construction of chimeric Ig genes, as reported by Liu et al. (*Proc. Natl. Acad. Sci. USA* 84: 3439 (1987); *J. Immuno.* 139:3521 (1987), which references are hereby incorporated by reference. The use of cDNA requires that gene expression elements appropriate for the host cell be combined with the gene in order to achieve synthesis of the desired protein. The use of cDNA sequences is advantageous over genomic sequences (which contain introns), in that cDNA sequences can be expressed in bacteria or other hosts which lack appropriate RNA splicing systems.

Therefore, in an embodiment utilizing cDNA encoding the Ab V region, the method of producing the chimeric Ab involves several steps, outlined below:

1. Isolation of messenger RNA (mRNA) from the cell line producing the mAb, cloning and cDNA production therefrom;
2. Preparation of a full length cDNA library from purified mRNA from which the appropriate V region gene segments of the L and H chain genes can be: (i) identified with appropriate probes, (ii) sequenced, and (iii) made compatible with a C gene segment;
3. Preparation of C region gene segments by cDNA preparation and cloning;
4. Construction of complete H or L chain coding sequences by linkage of the cloned specific V region gene segments to cloned human C region gene, as described above;
5. Expression and production of chimeric L and H chains in selected hosts, including prokaryotic and eukaryotic cells.

One common feature of all Ig H and L chain genes and their encoded mRNAs is the J region. H and L chain J regions have different sequences, but a high degree of sequence homology exists (greater than 80%) among each group, especially near the C region. This homology is exploited in this method and consensus sequences of H and L chain J regions may be used to design oligonucleotides for use as primers for introducing useful restriction sites into the J region for subsequent linkage of V region segments to human C region segments.

C region cDNA vectors prepared from human cells can be modified by site-directed mutagenesis to place a restriction site at the analogous position in the human sequence. For example, one can clone the complete human κ chain C ($C_\kappa$) region and the complete human γ-1 C region ($C_{\gamma-1}$). In this case, the alternative method based upon genomic C region clones as the source for C region vectors would not allow these genes to be expressed in bacterial systems where enzymes needed to remove intervening sequences are absent. Cloned V region segments are excised and ligated to L or H chain C region vectors.

Alternatively, the human $C_{\gamma-1}$ region can be modified by introducing a termination codon thereby generating a gene sequence which encodes the H chain portion of a Fab molecule. The coding sequences with linked V and C regions are then transferred into appropriate expression vehicles for expression in appropriate hosts, prokaryotic or eukaryotic.

Two coding DNA sequences are said to be "operably linked" if the linkage results in a continuously translatable sequence without alteration or interruption of the triplet reading frame. A DNA coding sequence is operably linked to a gene expression element if the linkage results in the proper function of that gene expression element to result in expression of the coding sequence.

Expression vehicles include plasmids or other vectors. Preferred among these are vehicles carrying a functionally complete human CH or CL chain sequence having appropriate restriction sites engineered so that any VH or VL chain sequence with appropriate cohesive ends can be easily inserted therein. Human CH or CL chain sequence-containing vehicles thus serve as intermediates for the expression of any desired complete H or L chain in any appropriate host.

A chimeric mouse-human antibody will typically be synthesized from genes driven by the chromosomal gene promoters native to the mouse H and L chain V regions used in the constructs. Splicing usually occurs between the splice donor site in the mouse J region and the splice acceptor site preceding the human C region and also at the splice regions that occur within the human CH region; polyadenylation and transcription termination occur at native chromosomal sites downstream of the human coding regions.

Gene expression elements useful for the expression of cDNA genes include: (a) viral transcription promoters and their enhancer elements, such as the SV40 early promoter (Okayama, H. et al., *Mol. Cell. Biol.* 3:280 (1983)), Rous sarcoma virus LTR (Gorman, C. et al., *Proc. Natl. Acad. Sci., USA* 79:6777 (1982)), and Moloney murine leukemia virus LTR (Grosschedl, R et al., *Cell* 41:885 (1985)); (b) splice regions and polyadenylation sites such as those derived from the SV40 late region (Okayama et al., supra); and (c) polyadenylation sites such as in SV40 (Okayama et al., supra).

Ig cDNA genes may be expressed as described by Liu et al., supra, and Weidle, U H et al., *Gene* 51:21-29 (1987), using as expression elements the SV40 early promoter and its enhancer, the mouse Ig H chain promoter enhancers, SV40 late region mRNA splicing, rabbit B-globin intervening sequence, Ig and rabbit (3-globin polyadenylation sites, and SV40 polyadenylation elements. For Ig genes comprised of part cDNA, part genomic DNA (Whittle, N et al., *Protein Eng.* 1:499-505 (1987)), the transcriptional promoter is human cytomegalovirus, the promoter enhancers are cytomegalovirus and mouse/human Ig, and mRNA splicing and polyadenylation regions are from the native chromosomal Ig sequences. In one embodiment, for expression of cDNA genes in rodent cells, the transcriptional promoter is a viral LTR sequence, the transcriptional promoter enhancers are either or both the mouse Ig H chain enhancer and the viral LTR enhancer, the splice region contains an intron of greater than 31 bp, and the polyadenylation and transcription termination regions are derived from the native chromosomal sequence corresponding to the Ig chain being synthesized. In other embodiments, cDNA sequences encoding other proteins are combined with the above-recited expression elements to achieve expression of the proteins in mammalian cells.

Each fused gene is assembled in, or inserted into, an expression vector. Recipient cells capable of expressing the chimeric Ig chain gene product are then transfected singly with a chimeric H or chimeric L chain-encoding gene, or are co-transfected with a chimeric H and a chimeric L chain gene. The transfected recipient cells are cultured under conditions that permit expression of the incorporated genes and the expressed Ig chains or intact antibodies or fragments are recovered from the culture. In one embodiment, the fused genes encoding the chimeric H and L chains, or portions thereof, are assembled in separate expression vectors that are then used to co-transfect a recipient cell.

Each vector may contain two selectable genes, a first selectable gene designed for selection in a bacterial system and a second selectable gene designed for selection in a eukaryotic system, wherein each vector has a different pair of genes. This strategy results in vectors which first direct the production, and permit amplification, of the fused genes in a bacterial system. The genes so produced and amplified in a bacterial host are subsequently used to co-transfect a eukaryotic cell, and allow selection of a co-transfected cell carrying the desired transfected genes. Examples of selectable genes for use in a bacterial system are the gene that confers resistance to ampicillin and the gene that confers resistance to chloramphenicol. Preferred selectable genes for use in eukaryotic transfectants include the xanthine guanine phosphoribosyl transferase gene (designated gpt) and the phosphotransferase gene from Tn5 (designated neo).

Selection of cells expressing gpt is based on the fact that the enzyme encoded by this gene utilizes xanthine as a substrate for purine nucleotide synthesis, whereas the analogous endogenous enzyme cannot.

In a medium containing (1) mycophenolic acid, which blocks the conversion of inosine monophosphate to xanthine monophosphate (XMP), and (2) xanthine, only cells expressing the gpt gene can survive. The product of the neo gene blocks the inhibition of protein synthesis by the antibiotic G418 and other antibiotics of the neomycin class.

The two selection procedures can be used simultaneously or sequentially to select for the expression of Ig chain genes introduced on two different DNA vectors into a eukaryotic cell. It is not necessary to include different selectable markers for eukaryotic cells; an H and an L chain vector, each containing the same selectable marker can be co-transfected. After selection of the appropriately resistant cells, the majority of the clones will contain integrated copies of both H and L chain vectors.

Alternatively, the fused genes encoding the chimeric H and L chains can be assembled on the same expression vector.

For transfection of the expression vectors and production of the chimeric antibody, the preferred recipient cell line is a myeloma cell. Myeloma cells can synthesize, assemble and secrete Igs encoded by transfected Ig genes and possess the mechanism for glycosylation of the Ig. A particularly preferred recipient cell is the Ig-non-producing myeloma cell SP2/0 (ATCC No. CRL 8287). SP2/0 cells produce only Ig encoded by the transfected genes. Myeloma cells can be grown in culture or in the peritoneal cavity of a mouse, where secreted Ig can be obtained from ascites fluid. Other suitable recipient cells include lymphoid cells such as B lymphocytes of human or non-human origin, hybridoma cells of human or non-human origin, or interspecies heterohybridoma cells.

The expression vector carrying a chimeric antibody construct of the present invention may be introduced into an appropriate host cell by any of a variety of suitable means, including such biochemical means as transformation, transfection, conjugation, protoplast fusion, calcium phosphate-precipitation, and application with polycations such as diethylaminoethyl (DEAE) dextran, and such mechanical means as electroporation, direct microinjection, and microprojectile bombardment.

The chimeric Ig coding sequences or genes of the present invention can also be expressed in nonlymphoid mammalian cells or in other eukaryotic cells, such as yeast, or in prokaryotic cells, in particular bacteria. Yeast provides substantial advantages over bacteria for the production of Ig H and L chains. Yeasts carry out post-translational peptide modifications including glycosylation. A number of recombinant DNA strategies now exist which utilize strong promoter sequences and high copy number plasmids which can be used for production of the desired proteins in yeast. Yeast recognizes leader sequences of cloned mammalian gene products and secretes peptides bearing leader sequences (i.e., pre-peptides). Yeast gene expression systems can be routinely evaluated for the levels of production, secretion and the stability of chimeric H and L chain proteins and assembled chimeric antibodies. Any of a series of yeast gene expression systems incorporating promoter and termination elements from the actively expressed genes coding for glycolytic enzymes produced in large quantities when yeasts are grown in media rich in glucose can be utilized. Known glycolytic genes can also provide very efficient transcription control signals. For example, the promoter and terminator signals of the phosphoglycerate kinase (PGK) gene can be utilized. A number of approaches may be taken for evaluating optimal expression plasmids for the expression of cloned Ig cDNAs in yeast (see Glover, D. M., ed., DNA Cloning, IRL Press, 1985).

Bacterial strains may also be utilized as hosts for the production of Ab molecules or Ab fragments described by this invention, E. coli K12 strains such as E. coli W3110 (ATCC No. 27325), and other enterobacteria such as Salmonella typhimurium or Serratia marcescens, and various Pseudomonas species may be used.

Plasmid vectors containing replicon and control sequences which are derived from species compatible with a host cell are used in connection with these bacterial hosts. The vector carries a replication site, as well as specific genes which are capable of providing phenotypic selection in transformed cells. A number of approaches may be taken for evaluating the expression plasmids for the production of chimeric antibodies or antibody chains encoded by the cloned Ig cDNAs in bacteria (see Glover, supra).

Preferred hosts are mammalian cells, grown in vitro or in vivo. Mammalian cells provide post-translational modifications to Ig protein molecules including leader peptide removal, folding and assembly of H and L chains, glycosylation of the Ab molecules, and secretion of functional Ab protein.

Mammalian cells which may be useful as hosts for the production of Ab proteins, in addition to the cells of lymphoid origin described above, include cells of fibroblast origin, such as Vero (ATCC CRL 81) or CHO-K (ATCC CRL 61). Many vector systems are available for the expression of cloned H and L chain genes in mammalian cells (see Glover, supra). Different approaches can be followed to obtain complete H2L2 Abs.

For in vivo use, particularly for injection into humans, it is desirable to decrease the immunogenicity of the monoclonal antibodies by making mouse-human (or rodent-human) chimeric antibodies as above, or by humanizing the antibodies using methods known in the art. The humanized antibody may be the product of an animal having transgenic human Ig Constant region genes (see for example WO90/10077 and WO90/04036). Alternatively, the antibody of interest may be genetically engineered to substitute the CHI, CH2, CH3, hinge domains, and/or the framework domain with the corresponding human sequence (see WO 92/02190).

5.5. Antibody Conjugates

The present invention encompasses the use of antibodies or fragments thereof recombinantly fused or chemically conjugated (including both covalent and non-covalent conjugations) to a heterologous polypeptide (or portion thereof, preferably to a polypeptide of at least 10, at least 20, at least 30, at least 40, at least 50, at least 60, at least 70, at least 80, at least 90 or at least 100 amino acids) to generate fusion proteins. The fusion does not necessarily need to be direct, but may occur through linker sequences. For example, antibodies may be used to target heterologous polypeptides to particular cell types, either in vitro or in vivo, by fusing or conjugating the antibodies to antibodies specific for particular cell surface receptors. Antibodies fused or conjugated to heterologous polypeptides may also be used in in vitro immunoassays and purification methods using methods known in the art. See e.g., International Publication WO 93/21232; EP 439,095; Naramura et al., 1994, *Immunol. Lett.* 39:91-99; U.S. Pat. No. 5,474,981; Gillies et al., 1992, *PNAS* 89:1428-1432; and Fell et al., 1991, *J. Immunol.* 146:2446-2452, which are incorporated by reference in their entireties.

The present invention further includes compositions comprising heterologous polypeptides fused or conjugated to antibody fragments. For example, the heterologous polypeptides may be fused or conjugated to a Fab fragment, Fd fragment, Fv fragment, F(ab)$_2$ fragment, or portion thereof. Methods for fusing or conjugating polypeptides to antibody portions are known in the art. See, e.g., U.S. Pat. Nos. 5,336,603, 5,622,929, 5,359,046, 5,349,053, 5,447,851, and 5,112,946; EP 307,434; EP 367,166; International Publication Nos. WO 96/04388 and WO 91/06570; Ashkenazi et al., 1991, *PNAS* 88: 10535-10539; Zheng et al., 1995, *J. Immunol.* 154:5590-5600; and Vil et al., 1992, *PNAS* 89:11337-11341 (said references incorporated by reference in their entireties).

Additional fusion proteins may be generated through the techniques of gene-shuffling, motif-shuffling, exon-shuffling, and/or codon-shuffling (collectively referred to as "DNA shuffling"). DNA shuffling may be employed to alter the activities of antibodies of the invention or fragments thereof (e.g., antibodies or fragments thereof with higher affinities and lower dissociation rates). See, generally, U.S. Pat. Nos. 5,605,793; 5,811,238; 5,830,721; 5,834,252; and 5,837,458, and Patten et al., 1997, *Curr. Opinion Biotechnol.* 8:724-33; Harayama, 1998, *Trends Biotechnol.* 16:76; Hansson, et al., 1999, *J. Mol. Biol.* 287:265; and Lorenzo and Blasco, 1998, *BioTechniques* 24:308 (each of these patents and publications are hereby incorporated by reference in its entirety). Antibodies or fragments thereof, or the encoded antibodies or fragments thereof, may be altered by being subjected to random mutagenesis by error-prone PCR, random nucleotide insertion or other methods prior to recombination. One or more portions of a polynucleotide encoding an antibody or antibody fragment, which portions immunospecifically bind to uPAR may be recombined with one or more components, motifs, sections, parts, domains, fragments, etc. of one or more heterologous molecules.

Moreover, the antibodies or fragments thereof can be fused to marker sequences, such as a peptide to facilitate purification. In preferred embodiments, the marker amino acid sequence is a hexa-histidine peptide, such as the tag provided in a pQE vector (QIAGEN, Inc., 9259 Eton Avenue, Chatsworth, Calif., 91311), among others, many of which are commercially available. As described in Gentz et al., 1989, *PNAS* 86:821, for instance, hexa-histidine provides for convenient purification of the fusion protein. Other peptide tags useful for purification include, but are not limited to, the hemagglutinin "HA" tag, which corresponds to an epitope derived from the influenza hemagglutinin protein (Wilson et al., 1984, *Cell* 37:767) and the "flag" tag.

5.5.1. Diagnostically Labeled Antibodies

In other embodiments, antibodies of the present invention or fragments or variants thereof are conjugated to a diagnostic or detectable agent. Such antibodies can be useful for monitoring or prognosing the development or progression of a cancer as part of a clinical testing procedure, such as determining the efficacy of a particular therapy.

The term "diagnostically labeled" means that the present antibody has attached to it a diagnostically detectable label. There are many different labels and methods of labeling known to those of ordinary skill in the art, described below. General classes of labels which can be used in the present invention include radioactive isotopes, paramagnetic isotopes, and compounds which can be imaged by positron emission tomography (PET), fluorescent or colored compounds, etc. Suitable detectable labels include radioactive, fluorescent, fluorogenic, chromogenic, or other chemical labels. Useful radiolabels (radionuclides), which are detected simply by gamma counter, scintillation counter or autoradiography include $^3$H, $^{125}$I, $^{131}$I, $^{135}$S and $^{14}$C. $^{131}$I is also a useful therapeutic isotope (see below).

A number of U.S. patents, incorporated by reference herein, disclose methods and compositions for complexing metals to larger molecules, including description of useful chelating agents. The metals are preferably detectable metal atoms, including radionuclides, and are complexed to proteins and other molecules. These documents include: U.S. Pat. Nos. 5,627,286; 5,618,513; 5,567,408; 5,443,816; and 5,561,220.

Common fluorescent labels include fluorescein, rhodamine, dansyl, phycoerythrin, phycocyanin, allophycocyanin, o-phthaldehyde and fluorescamine. The fluorophore, such as the dansyl group, must be excited by light of a particular wavelength to fluoresce. See, for example, Haugland, Handbook of Fluorescent Probes and Research Chemicals, Sixth Ed., Molecular Probes, Eugene, Oreg., 1996). Fluorescein, fluorescein derivatives and fluorescein-like molecules such as Oregon Green™ and its derivatives, Rhodamine Green™ and Rhodol Green™, are coupled to amine groups using the isothiocyanate, succinimidyl ester or dichlorotriazinyl-reactive groups. Similarly, fluorophores may also be coupled to thiols using maleimide, iodoacetamide, and aziridine-reactive groups. The long wavelength rhodamines, which are basically Rhodamine Green™ derivatives with substituents on the nitrogens, are among the most photostable fluorescent labeling reagents known. Their spectra are not affected by changes in pH between 4 and 10, an important advantage over the fluoresceins for many biological applications. This group includes the tetramethylrhodamines, X-rhodamines and Texas Red™ derivatives. Other preferred fluorophores for derivatizing the peptide according to this invention are those which are excited by ultraviolet light. Examples include cascade blue, coumarin derivatives, naphthalenes (of which dansyl chloride is a member), pyrenes and pyridyloxazole derivatives. Also included as labels are two related inorganic materials that have recently been described: semiconductor nanocrystals, comprising, for example, cadmium sulfate (Bruchez, M et al., Science 281:2013-2016 (1998), and quantum dots, e.g., zinc-sulfide-capped Cd selenide (Chan, W C et al., Science 281:2016-2018 (1998)).

In yet another approach, the amino group of the antibody is allowed to react with reagents that yield fluorescent products, for example, fluorescamine, dialdehydes such as o-phthaldialdehyde, naphthalene-2,3-dicarboxylate and anthracene-2,3-dicarboxylate. 7-nitrobenz-2-oxa-1,3-diazole (NBD) derivatives, both chloride and fluoride, are useful to modify amines to yield fluorescent products.

The antibody of the invention can also be labeled for detection using fluorescence-emitting metals such as $^{152}$Eu, or others of the lanthanide series. These metals can be attached to the peptide using such metal chelating groups as diethylenetriaminepentaacetic acid (DTPA) or ethylene-diaminetetraacetic acid (EDTA). DTPA, for example, is available as the anhydride, which can readily modify the NH$_2$-containing peptides of this invention.

For in vivo diagnosis or therapy, radionuclides may be bound to the antibody either directly or indirectly using a chelating agent such as DTPA and DOTA. Examples of such radionuclides are $^{99}$Tc, $^{123}$I, $^{125}$I, $^{131}$I, $^{111}$In, $^{97}$Ru, $^{67}$Cu, $^{67}$Ga, $^{68}$Ga, $^{72}$As, $^{89}$Zr, $^{90}$Y and $^{201}$Ti. Generally, the amount of labeled antibody needed for detectability in diagnostic use will vary depending on considerations such as age, condition, sex, and extent of disease in the patient, contraindications, if any, and other variables, and is to be adjusted by the individual physician or diagnostician. Dosage can vary from 0.001 mg/kg to 100 mg/kg.

The antibody can also be made detectable by coupling to a phosphorescent or a chemiluminescent compound. The presence of the chemiluminescent-tagged peptide is then determined by detecting the presence of luminescence that arises during the course of a chemical reaction. Examples of particularly useful chemiluminescers are luminol, isoluminol, theromatic acridinium ester, imidazole, acridinium salt and oxalate ester. Likewise, a bioluminescent compound may be used to label the peptides. Bioluminescence is a type of chemiluminescence found in biological systems in which a catalytic protein increases the efficiency of the chemiluminescent reaction. The presence of a bioluminescent protein is determined by detecting the presence of luminescence. Important bioluminescent compounds for purposes of labeling are luciferin, luciferase and aequorin.

In yet another embodiment, colorimetric detection is used, based on chromogenic compounds which have, or result in, chromophores with high extinction coefficients.

In situ detection of the labeled peptide may be accomplished by removing a histological specimen from a subject and examining it by microscopy under appropriate conditions to detect the label. Those of ordinary skill will readily perceive that any of a wide variety of histological methods (such as staining procedures) can be modified in order to achieve such in situ detection.

For diagnostic in vivo radioimaging, the type of detection instrument available is a major factor in selecting a radionuclide. The radionuclide chosen must have a type of decay which is detectable by a particular instrument. In general, any conventional method for visualizing diagnostic imaging can be utilized in accordance with this invention. Another factor in selecting a radionuclide for in vivo diagnosis is that its half-life be long enough so that the label is still detectable at the time of maximum uptake by the target tissue, but short enough so that deleterious irradiation of the host is minimized. In one preferred embodiment, a radionuclide used for in vivo imaging does not emit particles, but produces a large number of photons in a 140-200 keV range, which may be readily detected by conventional gamma cameras.

In vivo imaging may be used to detect occult metastases which are not observable by other methods. Imaging could be used, for example, to stage tumors non-invasively.

5.5.2. Therapeutically Labeled Antibodies

The present invention further encompasses uses of antibodies or fragments thereof conjugated to a therapeutic agent. In one embodiment, the monoclonal antibodies describe herein are "therapeutically conjugated" or "therapeutically labeled" (terms which are intended to be interchangeable) and used to deliver a therapeutic agent to the site to which the compounds home and bind, such as sites of tumor metastasis or foci of infection/inflammation, restenosis or fibrosis. The term "therapeutically conjugated" means that the modified monoclonal antibody is conjugated to another therapeutic agent that is directed either to the underlying cause or to a "component" of tumor invasion, angiogenesis, inflammation or other pathology. A therapeutically labeled polypeptide carries a suitable therapeutic "label" also referred to herein as a "therapeutic moiety." A therapeutic moiety is an atom, a molecule, a compound or any chemical component added to the peptide that renders it active in treating a target disease or condition, primarily one a associated with undesired angiogenesis. The therapeutic moiety may be bound directly or indirectly to the monoclonal antibody. The therapeutically labeled monoclonal antibody is administered as pharmaceutical composition which comprises a pharmaceutically acceptable carrier or excipient, and is preferably in a form suitable for injection.

Examples of useful therapeutic radioisotopes (ordered by atomic number) include $^{47}$Sc, $^{67}$Cu, $^{90}$Y, $^{109}$Pd, $^{125}$I, $^{131}$I, $^{186}$Re, $^{188}$Re, $^{199}$Au, $^{211}$At, $^{212}$Pb and $^{217}$Bi. These atoms can be conjugated to the peptide directly, indirectly as part of a chelate, or, in the case of iodine, indirectly as part of an iodinated Bolton-Hunter group. The radioiodine can be introduced either before or after this group is coupled to the peptide compound.

Preferred doses of the radionuclide conjugates are a function of the specific radioactivity to be delivered to the target site which varies with tumor type, tumor location and vascularization, kinetics and biodistribution of the peptide carrier, energy of radioactive emission by the nuclide, etc. Those skilled in the art of radiotherapy can readily adjust the dose of the peptide in conjunction with the dose of the particular nuclide to effect the desired therapeutic benefit without undue experimentation.

Another therapeutic approach included here is the use of boron neutron capture therapy, where a boronated peptide is delivered to a desired target site, such as a tumor, most preferably an intracranial tumor (Barth, R F, Cancer Invest. 14: 534-550 (1996); Mishima, Y (ed.), Cancer Neutron Capture Therapy, New York: Plenum Publishing Corp., 1996; Soloway, A H et al., (eds), J. Neuro-Oncol. 33: 1-188 (1997). The stable isotope $^{10}$B is irradiated with low energy (<0.025 eV) thermal neutrons, and the resulting nuclear capture yields a-particles and 7Li nuclei which have high linear energy transfer and respective path lengths of about 9 and 5 m. This method is predicated on $^{10}$B accumulation in the tumor with lower levels in blood, endothelial cells and normal tissue (e.g., brain). Such delivery has been accomplished using epidermal growth factor (Yang. W et al., Cancer Res 57:4333-4339 (1997).

Other therapeutic agents which can be coupled to the monoclonal antibodies according to the method of the invention are drugs, prodrugs, enzymes for activating pro-drugs, photosensitizing agents, nucleic acid therapeutics, antisense vectors, viral vectors, lectins and other toxins.

Lectins are proteins, commonly derived from plants, that bind to carbohydrates. Among other activities, some lectins are toxic. Some of the most cytotoxic substances known are protein toxins of bacterial and plant origin (Frankel, A E et al., Ann. Rev. Med. 37:125-142 (1986)). These molecules binding the cell surface and inhibit cellular protein synthesis. The most commonly used plant toxins are ricin and abrin; the most commonly used bacterial toxins are diphtheria toxin and *Pseudomonas* exotoxin A. In ricin and abrin, the binding and toxic functions are contained in two separate protein subunits, the A and B chains. The ricin B chain binds to the cell surface carbohydrates and promotes the uptake of the A chain into the cell. Once inside the cell, the ricin A chain inhibits protein synthesis by inactivating the 60S subunit of the eukaryotic ribosome Endo, Y. et al., J. Biol. Chem. 262: 5908-5912 (1987)). Other plant derived toxins, which are single chain ribosomal inhibitory proteins, include pokeweed antiviral protein, wheat germ protein, gelonin, dianthins, momorcharins, trichosanthin, and many others (Strip, F. et al., FEBS Lett. 195:1-8 (1986)). Diphtheria toxin and *Pseudomonas* exotoxin A are also single chain proteins, and their binding and toxicity functions reside in separate domains of the same protein *Pseudomonas* exotoxin A has the same catalytic activity as diphtheria toxin. Ricin has been used therapeutically by binding its toxic a-chain, to targeting molecules such as Abs to enable site-specific delivery of the toxic effect. Bacterial toxins have also been used as anti-tumor conjugates. As intended herein, a toxic peptide chain or domain is conjugated to a compound of this invention and delivered in a site-specific manner to a target site where the toxic activity is desired, such as a metastatic focus.

Conjugation of toxins to protein such as Abs or other ligands are known in the art (Olsnes, S. et al., *Immunol. Today* 10:291-295 (1989); Vitetta, E S et al., *Ann. Rev. Immunol.* 3: 197-212 (1985)).

An antibody or fragment thereof may be conjugated to a therapeutic moiety such as a cytotoxin, e.g., a cytostatic or cytocidal agent, a therapeutic agent or a radioactive metal ion, e.g., alpha-emitters. A cytotoxin or cytotoxic agent includes any agent that is detrimental to cells. Examples include paclitaxel, cytochalasin B, gramicidin D, ethidium bromide, emetine, methotrexate, mitomycin, etoposide, tenoposide, vincristine, vinblastine, colchicin, doxorubicin, daunorubicin, dihydroxy anthracin dione, Mitomycin C, mitoxantrone, mithramycin, actinomycin D, 1-dehydrotestosterone, glucocorticoids, procaine, tetracaine, lidocaine, propranolol, puromycin, epirubicin, and cyclophosphamide and analogs or homologs thereof. Therapeutic agents include, but are not limited to, antimetabolites (e.g., methotrexate, 6-mercaptopurine, 6-thioguanine, cytarabine, 5-fluorouracil decarbazine), alkylating agents (e.g., mechlorethamine, thioepa chlorambucil, melphalan, carmustine (BCNU) and lomustine (CCNU), cyclothosphamide, busulfan, dibromomannitol, streptozotocin, mitomycin C, and cisdichlorodiamine platinum (II) (DDP) cisplatin), anthracyclines (e.g., daunorubicin (formerly daunomycin) and doxorubicin), antibiotics (e.g., dactinomycin (formerly actinomycin), bleomycin, mithramycin, and anthramycin (AMC)), and anti-mitotic agents (e.g., vincristine and vinblastine).

Further, an antibody or fragment thereof may be conjugated to a therapeutic agent or drug moiety that modifies a given biological response. Therapeutic agents or drug moieties are not to be construed as limited to classical chemical therapeutic agents. For example, the drug moiety may be a protein or polypeptide possessing a desired biological activity. Such proteins may include, for example, a toxin such as abrin, ricin A, pseudomonas exotoxin, cholera toxin, or diphtheria toxin; a protein such as tumor necrosis factor, α-interferon, β-interferon, nerve growth factor, platelet derived growth factor, tissue plasminogen activator, an apoptotic agent, e.g., TNF-α, TNF-β, AIM I (see, International Publication No. WO 97/33899), AIM II (see, International Publication No. WO 97/34911), Fas Ligand (Takahashi et al., 1994, *J. Immunol.*, 6:1567), and VEGI (see, International Publication No. WO 99/23105), a thrombotic agent or an anti-angiogenic agent, e.g., angiostatin or endostatin; or, a biological response modifier such as, for example, a lymphokine (e.g., interleukin-1 ("IL-1"), interleukin-2 ("IL-2"), interleukin-6 ("IL-6"), granulocyte macrophage colony stimulating factor ("GM-CSF"), and granulocyte colony stimulating factor ("G-CSF")), or a growth factor (e.g., growth hormone ("GH")).

Moreover, an antibody can be conjugated to therapeutic moieties such as a macrocyclic chelators useful for conjugating radiometal ions (see above for examples of radioactive materials). In certain embodiments, the macrocyclic chelator is 1,4,7,10-tetraazacyclododecane-N,N',N'',N'''-tetraacetic acid (DOTA) which can be attached to the antibody via a linker molecule. Such linker molecules are commonly known in the art and described in Denardo et al., 1998, *Clin Cancer Res.* 4:2483-90; Peterson et al., 1999, *Bioconjug. Chem.* 10:553; and Zimmerman et al., 1999, *Nucl. Med. Biol.* 26:943-50 each incorporated by reference in their entireties.

Techniques for conjugating therapeutic moieties to antibodies are well known. Moieties can be conjugated to antibodies by any method known in the art, including, but not limited to aldehyde/Schiff linkage, sulphydryl linkage, acid-labile linkage, cis-aconityl linkage, hydrazone linkage, enzymatically degradable linkage (see generally Garnett, 2002, *Adv. Drug Deliv. Rev.* 53:171-216). Additional techniques for conjugating therapeutic moieties to antibodies are well known, see, e.g., Arnon et al., "Monoclonal Antibodies For Immunotargeting Of Drugs In Cancer Therapy," in Monoclonal Antibodies And Cancer Therapy, Reisfeld et al. (eds.), pp. 243-56 (Alan R. Liss, Inc. 1985); Hellstrom et al., "Antibodies For Drug Delivery," in Controlled Drug Delivery (2nd Ed.), Robinson et al. (eds.), pp. 623-53 (Marcel Dekker, Inc. 1987); Thorpe, "Antibody Carriers Of Cytotoxic Agents In Cancer Therapy: A Review," in Monoclonal Antibodies '84: Biological And Clinical Applications, Pinchera et al. (eds.), pp. 475-506 (1985); "Analysis, Results, And Future Prospective Of The Therapeutic Use Of Radiolabeled Antibody In Cancer Therapy," in Monoclonal Antibodies For Cancer Detection And Therapy, Baldwin et al. (eds.), pp. 303-16 (Academic Press 1985), and Thorpe et al., 1982, *Immunol. Rev.* 62:119-58. Methods for fusing or conjugating antibodies to polypeptide moieties are known in the art. See, e.g., U.S. Pat. Nos. 5,336,603, 5,622,929, 5,359,046, 5,349,053, 5,447, 851, and 5,112,946; EP 307,434; EP 367,166; International Publication Nos. WO 96/04388 and WO 91/06570; Ashkenazi et al., 1991, *PNAS* 88: 10535-10539; Zheng et al., 1995, *J. Immunol.* 154:5590-5600; and Vil et al., 1992, PNAS 89:11337-11341. The fusion of an antibody to a moiety does not necessarily need to be direct, but may occur through linker sequences. Such linker molecules are commonly known in the art and described in Denardo et al., 1998, *Clin Cancer Res.* 4:2483-90; Peterson et al., 1999, *Bioconjug. Chem.* 10:553; Zimmerman et al., 1999, *Nucl. Med. Biol.* 26:943-50; Garnett, 2002, *Adv. Drug Deliv. Rev.* 53:171-216, each of which is incorporated herein by reference in its entirety.

Alternatively, an antibody can be conjugated to a second antibody to form an antibody heteroconjugate as described by Segal in U.S. Pat. No. 4,676,980, which is incorporated herein by reference in its entirety.

Antibodies may also be attached to solid supports, which are particularly useful for immunoassays or purification of the target antigen. Such solid supports include, but are not limited to, glass, cellulose, polyacrylamide, nylon, polystyrene, polyvinyl chloride or polypropylene.

5.6. Pharmaceutical and Therapeutic Compositions and their Administration

The compounds that may be employed in the pharmaceutical compositions of the invention include all of the polypeptide molecules, preferably monoclonal antibodies, described above, as well as the pharmaceutically acceptable salts of these compounds. In a specific embodiment, the term "pharmaceutically acceptable" means approved by a regulatory agency of the Federal or a state government or listed in the U.S. Pharmacopeia or other generally recognized pharmacopeia for use in animals, and more particularly in humans. The term "carrier" refers to a diluent, adjuvant (e.g., Freund's adjuvant (complete and incomplete) or, more preferably, MF59C.1 adjuvant available from Chiron, Emeryville, Calif.), excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Water is a preferred carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The composition, if desired, can also contain minor amounts of wetting or emulsifying agents, or pH buffering agents. These compositions can take the form of solutions, suspensions, emulsion, tablets, pills, capsules, powders, sustained-release formulations and the like.

The compositions of the invention can be formulated as neutral or salt forms.

Pharmaceutically acceptable acid addition salts of the compounds of the invention containing a basic group are formed where appropriate with strong or moderately strong, non-toxic, organic or inorganic acids by methods known to the art. Exemplary of the acid addition salts that are included in this invention are maleate, fumarate, lactate, oxalate, methanesulfonate, ethanesulfonate, benzenesulfonate, tartrate, citrate, hydrochloride, hydrobromide, sulfate, phosphate and nitrate salts.

Pharmaceutically acceptable base addition salts of compounds of the invention containing an acidic group are prepared by known methods from organic and inorganic bases and include, for example, nontoxic alkali metal and alkaline earth bases, such as calcium, sodium, potassium and ammonium hydroxide; and nontoxic organic bases such as triethylamine, butylamine, piperazine, and tri(hydroxymethyl)methylamine.

Generally, the ingredients of compositions of the invention are supplied either separately or mixed together in unit dosage form, for example, as a dry lyophilized powder or water free concentrate in a hermetically sealed container such as an ampoule or sachette indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

The compounds of the invention, as well as the pharmaceutically acceptable salts thereof, may be incorporated into convenient dosage forms, such as capsules, impregnated wafers, tablets or injectable preparations. Solid or liquid pharmaceutically acceptable carriers may be employed.

Solid carriers include starch, lactose, calcium sulfate dihydrate, terra alba, sucrose, talc, gelatin, agar, pectin, acacia, magnesium stearate and stearic acid. Liquid carriers include syrup, peanut oil, olive oil, saline, water, dextrose, glycerol and the like. Similarly, the carrier or diluent may include any prolonged release material, such as glyceryl monostearate or glyceryl distearate, alone or with a wax.

When a liquid carrier is used, the preparation may be in the form of a syrup, elixir, emulsion, soft gelatin capsule, sterile injectable liquid (e.g., a solution), such as an ampoule, or an aqueous or nonaqueous liquid suspension. A summary of such pharmaceutical compositions may be found, for example, in Remington's Pharmaceutical Sciences, Mack Publishing Company, Easton Pa. (Gennaro 18th ed. 1990).

The pharmaceutical preparations are made following conventional techniques of pharmaceutical chemistry involving such steps as mixing, granulating and compressing, when necessary for tablet forms, or mixing, filling and dissolving the ingredients, as appropriate, to give the desired products for oral, parenteral, topical, transdermal, intravaginal, intrapenile, intranasal, intrabronchial, intracranial, intraocular, intraaural and rectal administration. The pharmaceutical compositions may also contain minor amounts of nontoxic auxiliary substances such as wetting or emulsifying agents, pH buffering agents and so forth.

The present invention may be used in the diagnosis or treatment of any of a number of animal genera and species, and are equally applicable in the practice of human or veterinary medicine. Thus, the pharmaceutical compositions can be used to treat domestic and commercial animals, including birds and more preferably mammals, as well as humans.

The term "systemic administration" refers to administration of a composition or agent such as the polypeptide, described herein, in a manner that results in the introduction of the composition into the subject's circulatory system or otherwise permits its spread throughout the body, such as intravenous (i.v.) injection or infusion. "Regional" administration refers to administration into a specific, and somewhat more limited, anatomical space, such as intraperitoneal, intrathecal, subdural, or to a specific organ. Examples include intravaginal, intrapenile, intranasal, intrabronchial (or lung instillation), intracranial, intra-aural or intraocular. The term "local administration" refers to administration of a composition or drug into a limited, or circumscribed, anatomic space, such as intratumoral injection into a tumor mass, subcutaneous (s.c.) injections, intramuscular (i.m.) injections. One of skill in the art would understand that local administration or regional administration often also result in entry of a composition into the circulatory system, i.e., so that s.c. or i.m. are also routes for systemic administration. Injectables or infusible preparations can be prepared in conventional forms, either as solutions or suspensions, solid forms suitable for solution or suspension in liquid prior to injection or infusion, or as emulsions. Though the preferred routes of administration are systemic, such as i.v., the pharmaceutical composition may be administered topically or transdermally, e.g., as an ointment, cream or gel; orally; rectally; e.g., as a suppository.

For topical application, the compound may be incorporated into topically applied vehicles such as a salve or ointment. The carrier for the active ingredient may be either in sprayable or nonsprayable form. Non-sprayable forms can be semi-solid or solid forms comprising a carrier indigenous to topical application and having a dynamic viscosity preferably greater than that of water. Suitable formulations include, but are not limited to, solution, suspensions, emulsions, creams, ointments, powders, liniments, salves, and the like. If desired, these may be sterilized or mixed with auxiliary agents, e.g., preservatives, stabilizers, wetting agents, buffers, or salts for influencing osmotic pressure and the like.

Preferred vehicles for non-sprayable topical preparations include ointment bases, e.g., polyethylene glycol-1000

(PEG-1000); conventional creams such as HEB cream; gels; as well as petroleum jelly and the like.

Also suitable for topic application as well as for lung instillation are sprayable aerosol preparations wherein the compound, preferably in combination with a solid or liquid inert carrier material, is packaged in a squeeze bottle or in admixture with a pressurized volatile, normally gaseous propellant.

The aerosol preparations can contain solvents, buffers, surfactants, perfumes, and/or antioxidants in addition to the compounds of the invention.

For the preferred topical applications, especially for humans, it is preferred to administer an effective amount of the compound to an affected area, e.g., skin surface, mucous membrane, eyes, etc.

This amount will generally range from about 0.001 mg to about 1 g per application, depending upon the area to be treated, the severity of the symptoms, and the nature of the topical vehicle employed.

Other pharmaceutically acceptable carriers for polypeptide compositions of the present invention are liposomes, pharmaceutical compositions in which the active protein is contained either dispersed or variously present in corpuscles consisting of aqueous concentric layers adherent to lipidic layers. The active polypeptide is preferably present in the aqueous layer and in the lipidic layer, inside or outside, or, in any event, in the non-homogeneous system generally known as a liposomic suspension.

The hydrophobic layer, or lipidic layer, generally, but not exclusively, comprises phospholipids such as lecithin and sphingomyelin, steroids such as cholesterol, more or less ionic surface active substances such as dicetylphosphate, stearylamine or phosphatidic acid, and/or other materials of a hydrophobic nature. Those skilled in the art will appreciate other suitable embodiments of the present liposomal formulations.

Therapeutic compositions for treating tumors and cancer may comprise, in addition to the peptide, one or more additional anti-tumor agents, such as mitotic inhibitors, e.g., vinblastine; alkylating agents, e.g., cyclophosphamide; folate inhibitors, e.g., methotrexate, piritrexim or trimetrexate; antimetabolites, e.g., 5-fluorouracil and cytosine arabinoside; intercalating antibiotics, e.g., adriamycin and bleomycin; enzymes or enzyme inhibitors, e.g., asparaginase, topoisomerase inhibitors such as etoposide; or biological response modifiers, e.g., interferons or interleukins. In fact, pharmaceutical compositions comprising any known cancer therapeutic in combination with the peptides disclosed herein are within the scope of this invention. The pharmaceutical composition may also comprise one or more other medicaments to treat additional symptoms for which the target patients are at risk, for example, anti-infectives including antibacterial, anti-fungal, anti-parasitic, anti-viral, and anti-coccidial agents.

The therapeutic dosage administered is an amount which is therapeutically effective, as is known to or readily ascertainable by those skilled in the art. The dose is also dependent upon the age, health, and weight of the recipient, kind of concurrent treatment (s), any, the frequency of treatment, and the nature of the effect desired, such as, for example, antiinflammatory effects or anti-bacterial effect.

Various delivery systems are known and can be used to administer a monoclonal antibody of the invention or the combination of a monoclonal antibody of the invention and a prophylactic agent or therapeutic agent useful for preventing or treating cancer, e.g., encapsulation in liposomes, microparticles, microcapsules, recombinant cells capable of expressing the antibody or antibody fragment, receptor-mediated endocytosis (see, e.g., Wu and Wu, 1987, *J. Biol. Chem.* 262:4429-4432), construction of a nucleic acid as part of a retroviral or other vector, etc. Methods of administering a prophylactic or therapeutic agent of the invention include, but are not limited to, parenteral administration (e.g., intradermal, intramuscular, intraperitoneal, intravenous and subcutaneous), epidural, and mucosal (e.g., intranasal, inhaled, and oral routes). In a specific embodiment, prophylactic or therapeutic agents of the invention are administered intramuscularly, intravenously, or subcutaneously. The prophylactic or therapeutic agents may be administered by any convenient route, for example by infusion or bolus injection, by absorption through epithelial or mucocutaneous linings (e.g., oral mucosa, rectal and intestinal mucosa, etc.) and may be administered together with other biologically active agents. Administration can be systemic or local.

In a specific embodiment, it may be desirable to administer the prophylactic or therapeutic agents of the invention locally to the area in need of treatment; this may be achieved by, for example, and not by way of limitation, local infusion, by injection, or by means of an implant, said implant being of a porous, non-porous, or gelatinous material, including membranes, such as sialastic membranes, or fibers.

In yet another embodiment, the prophylactic or therapeutic agent can be delivered in a controlled release or sustained release system. In one embodiment, a pump may be used to achieve controlled or sustained release (see Langer, supra; Sefton, 1987, *CRC Crit. Ref. Biomed. Eng.* 14:20; Buchwald et al., 1980, *Surgery* 88:507; Saudek et al., 1989, *N. Engl. J. Med.* 321:574). In another embodiment, polymeric materials can be used to achieve controlled or sustained release of the antibodies of the invention or fragments thereof (see e.g., Medical Applications of Controlled Release, Langer and Wise (eds.), CRC Pres., Boca Raton, Fla. (1974); Controlled Drug Bioavailability, Drug Product Design and Performance, Smolen and Ball (eds.), Wiley, New York (1984); Ranger and Peppas, 1983, *J. Macromol. Sci. Rev. Macromol. Chem.* 23:61; see also Levy et al., 1985, *Science* 228:190; During et al., 1989, *Ann. Neurol.* 25:351; Howard et al., 1989, *J. Neurosurg.* 7 1:105); U.S. Pat. Nos. 5,679,377; 5,916,597; 5,912, 015; 5,989,463; 5,128,326; International Publication Nos. WO 99/15154 and WO 99/20253. Examples of polymers used in sustained release formulations include, but are not limited to, poly(2-hydroxy ethyl methacrylate), poly(methyl methacrylate), poly(acrylic acid), poly(ethylene-co-vinyl acetate), poly(methacrylic acid), polyglycolides (PLG), polyanhydrides, poly(N-vinyl pyrrolidone), poly(vinyl alcohol), polyacrylamide, poly(ethylene glycol), polylactides (PLA), poly(lactide-co-glycolides) (PLGA), and polyorthoesters. In a preferred embodiment, the polymer used in a sustained release formulation is inert, free of leachable impurities, stable on storage, sterile, and biodegradable. In yet another embodiment, a controlled or sustained release system can be placed in proximity of the prophylactic or therapeutic target, thus requiring only a fraction of the systemic dose (see, e.g., Goodson, in Medical Applications of Controlled Release, supra, vol. 2, pp. 115-138 (1984)).

Controlled release systems are discussed in the review by Langer (1990, Science 249:1527-1533). Any technique known to one of skill in the art can be used to produce sustained release formulations comprising one or more therapeutic agents of the invention. See, e.g., U.S. Pat. No. 4,526, 938; International Publication Nos. WO 91/05548 and WO 96/20698; Ning et al., 1996, *Radiotherapy & Oncology* 39:179-189; Song et al., 1995, *PDA Journal of Pharmaceutical Science & Technology* 50:372-397; Cleek et al., 1997, *Pro. Int'l. Symp. Control. Rel. Bioact. Mater.* 24:853-854; and Lam et al., 1997, *Proc. Int'l. Symp. Control Rel. Bioact. Mater.* 24:759-760, each of which is incorporated herein by reference in its entirety.

5.7. Therapeutic Methods

The methods of this invention may be used to inhibit tumor growth and invasion in a subject or to suppress angiogenesis induced by tumors by inhibiting endothelial cell growth and migration. By inhibiting the growth or invasion of a tumor or angiogenesis, the methods result in inhibition of tumor metastasis. A vertebrate subject, preferably a mammal, such as a non-primate (e.g., cows, pigs, horses, cats, dogs, rats etc.) and a primate (e.g., monkey and human), more preferably a human, is administered an amount of the compound effective to inhibit tumor growth, invasion or angiogenesis. The compound or pharmaceutically acceptable salt thereof is preferably administered in the form of a pharmaceutical composition as described above.

The amount of the composition of the invention which will be effective in the prevention or treatment of cancer can be determined by standard research techniques. Effective doses may be extrapolated from dose-response curves derived from in vitro or animal model test systems. For example, the dosage of the composition which will be effective in the prevention or treatment of cancer can be determined by administering the composition to an animal model such as, e.g., the animal models disclosed herein or known to those skilled in the art. In addition, in vitro assays may optionally be employed to help identify optimal dosage ranges.

Doses of the proteins (including antibodies), peptides, peptide multimers, etc., preferably include pharmaceutical dosage units comprising an effective amount of the peptide. Dosage unit form refers to physically discrete units suited as unitary dosages for a mammalian subject; each unit contains a predetermined quantity of active material calculated to produce the desired therapeutic effect, in association with the required pharmaceutical carrier. The specification for the dosage unit forms of the invention are dictated by and directly dependent on (a) the unique characteristics of the active material and the particular therapeutic effect to be achieved, and (b) the limitations inherent in the art of compounding such an active compound for the treatment of, and sensitivity of, individual subjects.

By an effective amount is meant an amount sufficient to achieve a steady state concentration in vivo which results in a measurable reduction in any relevant parameter of disease and may include growth of primary or metastatic tumor, any accepted index of inflammatory reactivity, or a measurable prolongation of disease-free interval or of survival. For example, a reduction in tumor growth in 20% of patients is considered efficacious (Frei III, E., The Cancer Journal 3:127-136 (1997)). However, an effect of this magnitude is not considered to be a minimal requirement for the dose to be effective in accordance with this invention.

In one embodiment, an effective dose is preferably 10-fold and more preferably 100-fold higher than the 50% effective dose ($ED_{50}$) of the compound in an in vivo assay as described herein.

Selection of the preferred effective dose can be determined (e.g., via clinical trials) by a skilled artisan based upon the consideration of several factors which will be known to one of ordinary skill in the art. Such factors include the precise peptide or derivative selected, the disease or condition, the route of administration, the health and weight of the recipient, the existence of other concurrent treatment, if any, the frequency of treatment, the nature of the effect desired, for example, inhibition of tumor metastasis, and the judgment of the skilled practitioner.

A preferred dose for treating a subject, preferably mammalian, more preferably human, with a tumor is an amount of up to about 100 milligrams of active polypeptide-based compound per kilogram of body weight. A typical single dosage of the peptide or peptidomimetic is between about 1 ng and about 100 mg/kg body weight. For antibodies, the dosage administered to a patient is typically 0.1 mg/kg to 100 mg/kg of the patient's body weight. Preferably, the dosage administered to a patient is between 0.1 mg/kg and 20 mg/kg of the patient's body weight, more preferably 1 mg/kg to 10 mg/kg of the patient's body weight. For topical administration, dosages in the range of about 0.01-20% concentration (by weight) of the compound, preferably 1-5%, are suggested. A total daily dosage in the range of about 0.1 milligrams to about 7 grams is preferred for intravenous administration. The foregoing ranges are, however, suggestive, as the number of variables in an individual treatment regime is large, and considerable excursions from these preferred values are expected. Generally, human and humanized antibodies have a longer half-life within the human body than antibodies from other species due to the immune response to the foreign polypeptides. Thus, lower dosages of human antibodies and less frequent administration is often possible.

An effective amount or dose of the peptide for inhibiting endothelial cell proliferation or migration in vitro is in the range of about 1 picogram to about 5 nanograms per cell. Effective doses and optimal dose ranges may be determined in vitro using the methods described herein.

The compounds of the invention may be characterized as producing an inhibitory effect on tumor cell or endothelial cell proliferation, migration, invasion, or on angiogenesis, on tumor metastasis or on inflammatory reactions. The compounds are especially useful in producing an anti-tumor effect in a mammalian host, preferably human, harboring a tumor wherein angiogenesis inhibition results in reduction in size or growth rate of the tumor or destruction of the tumor. Preferably, the subject is a human.

A longer example of a disease or condition against which the above method is effective include primary growth of a solid tumor, leukemia or lymphoma; tumor invasion, metastasis or growth of tumor metastases; benign hyperplasia; atherosclerosis; myocardial angiogenesis; post-balloon angioplasty vascular restenosis; neointima formation following vascular trauma; vascular graft restenosis; coronary collateral formation; deep venous thrombosis; ischemic limb angiogenesis; telangiectasia; pyogenic granuloma; corneal disease; rubeosis; neovascular glaucoma; diabetic and other retinopathy; retrolental fibroplasia; diabetic neovascularization; macular degeneration; endometriosis; arthritis; fibrosis associated with a chronic inflammatory condition, traumatic spinal cord injury including ischemia, scarring or fibrosis; lung fibrosis, chemotherapy-induced fibrosis; wound healing with scarring and fibrosis; peptic ulcers; a bone fracture; keloids; or a disorder of vasculogenesis, hematopoiesis, ovulation, menstruation, pregnancy or placentation associated with pathogenic cell invasion or with angiogenesis.

A preferred disease or condition to be treated by the above method is tumor growth, invasion or metastasis. This includes brain tumors. Examples of such brain tumors are astrocytoma, anaplastic astrocytoma, glioblastoma, glioblastoma multiformae, pilocytic astrocytoma, pleiomorphic xanthoastrocytoma, subependymal giant cell astrocytoma, fibrillary astrocytoma, gemistocytic astrocytoma, protoplasmic astrocytoma, oligodendroglioma, anaplastic oligodendroglioma, ependymoma, anaplastic ependymoma, myxopapillary ependymoma, subependymoma, mixed oligoastrocytoma and malignant oligoastrocytoma.

The method is also used to treat a uterine disease such as endometriosis and pathogenic ocular neovascularization such as that associated with, or a cause of, proliferative diabetic retinopathy, neovascular age-related macular degeneration, retinopathy of prematurity, sickle cell retinopathy or retinal vein occlusion.

Angiogenesis inhibitors may play a role in preventing inflammatory angiogenesis and gliosis following traumatic spinal cord injury, thereby promoting the reestablishment of neuronal connectivity (Wamil, A W et al., *Proc. Nat'l. Acad. Sci. USA* 95:13188-13193 (1998)). Therefore, the compositions of the present invention are administered as soon as possible after traumatic spinal cord injury and for several days up to about two weeks thereafter to inhibit the angiogenesis and gliosis that would sterically prevent reestablishment of neuronal connectivity. The treatment reduces the area of damage at the site of spinal cord injury and facilitates regeneration of neuronal function and thereby prevents paralysis. The compounds of the invention are expected also to protect axons from Wallerian degeneration, reverse aminobutyrate-mediated depolarization (occurring in traumatized neurons), and improve recovery of neuronal conductivity of isolated central nervous system cells and tissue in culture.

For other cancer therapeutic agents administered to a patient, the typical doses of various cancer therapeutics are known in the art. Given the invention, certain preferred embodiments will encompass the administration of lower dosages in combination treatment regimens than dosages recommended for the administration of single agents.

The invention provides for any method of administrating lower doses of known prophylactic or therapeutic agents than previously thought to be effective for the prevention or treatment of cancer. Preferably, lower doses of known anti-cancer therapies are administered in combination with lower doses of monoclonal antibodies of the invention.

As used herein, the term "in combination" refers to the use of more than one prophylactic and/or therapeutic agents. The use of the term "in combination" does not restrict the order in which prophylactic and/or therapeutic agents are administered to a subject with a hyperproliferative cell disorder, especially cancer. A first prophylactic or therapeutic agent can be administered prior to (e.g., 1 minute, 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks before), concomitantly with, or subsequent to (e.g., 1 minute, 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks after) the administration of a second prophylactic or therapeutic agent to a subject which had, has, or is susceptible to a hyperproliferative cell disorder, especially cancer. The prophylactic or therapeutic agents are administered to a subject in a sequence and within a time interval such that the agent of the invention can act together with the other agent to provide an increased benefit than if they were administered otherwise. Any additional prophylactic or therapeutic agent can be administered in any order with the other additional prophylactic or therapeutic agents.

5.8. Assays 5.8.1. Use of Antibodies to Detect uPA- or uPAR-Complexes by Immunoassay Antibodies of this invention are useful in immunoassays to detect molecules containing these epitopes in tissue sample or a body fluid, such as serum or plasma. Such antibodies would detect the antigen or an epitope-bearing fragment thereof. Thus, if proteolysis in the tumor milieu results in release of the fragments or in tissue.

Any conventional immunoassay known in the art may be employed for this purpose, though Enzyme Immunoassays such as ELISA are preferred. Immunoassay methods are also described in references cited above.

Competitive immunoassays are typically used to detect molecules in a test sample that are ligands for the complex that may mimic the monoclonal antibodies in their binding specificity, affinity, capacity, etc. In one embodiment a competitive binding assay, the amount of antibody bound to the complex is measured (directly or indirectly using a labeled anti-Ig). Competition (i.e., less binding of antibody to complex) in the presence of the test sample is evidence that one or more components of the sample bind to the complex. It is expected that most compounds being tested will bind with moderate affinities (approximately 1-10 µM)

In another embodiment, a solid support, e.g., a microplate, is coated with the mAb of interest. The test sample is added and incubated, e.g., for about 30 minutes to allow binding of relevant molecules to the antibody. The plates are washed and the complex, in detectably labeled form (e.g., biotinylated), is added as the competitive ligand, and allowed to compete with the test sample for binding to the antibody. A "positive" result for the test sample will be expressed as less binding of labeled complex bound to the solid phase. This approach, in which the complex solution and sample solution are not added simultaneously, avoids the confounding effects of test sample binding directly to the complex, because any test sample present must first be captured by the immobilized mAb. Preferably, to assure that binding is specific, a series of dilutions are run to obtain a dilution curve. This will show if, for example, there is 50% less binding/signal ratio with half the sample. In the absence of such dilution effects, it may be concluded that multiple binding entities are entering into the assay. Results are more rigorous if molecules binding at the mAb binding site have similar affinities.

5.8.1.1. Immunohistochemical Assays

One preferred assay for detecting the antigens in a tissue is by immunohistochemistry, using any conventional assay methods, with which the art is replete. A preferred assay is the one described in the Examples below. For a description of such methods, see, for example, Dabbs, D J, Diagnostic Immunohistochemistry, Churchill Livingstone, 2001, which is incorporated by reference in its entirety.

5.8.1.2. Non-Histological Immunoassays

Preferred immunoassays are enzyme immunoassays (EIA's) such as ELISA, which employ antigens or Abs immobilized to solid supports. For the present compositions and methods, the solid support is preferably any one of polystyrene, polypropylene, polyethylene, dextran, nylon, polyacrylamide, polyvinylidene difluoride, natural cellulose, modified cellulose, nitrocellulose, agarose and magnetic beads. In a preferred embodiment, the surface of polystyrene or other plastic multiwell plates serves as the solid support. In another embodiment, a solid support to which the Ab or antigen is affixed to the bottom or placed loosely in the wells of multiwell plates. Multiwell plates in which the bottoms of the wells comprise nitrocellulose or a similar membrane material and through which liquid can be moved under pressure or vacuum may also be used.

Typical, and preferred, immunoassays include "forward" assays in which the Ab immobilized to a solid support is first contacted with the sample being tested to bind or "extract" the antigen from the sample by formation of a binary immobilized Ab-antigen complex. After suitable incubation, the solid support is washed to remove the residue of the fluid sample including unbound antigen, if any, and then contacted with the solution containing an unknown quantity of labeled antibody (which functions as a "reporter molecule"). After a second incubation, that permits the labeled antibody to complex with the immobilized antigen through the unlabeled Ab, the solid support is washed a second time to remove the unreacted labeled Ab and the immobilized label is measured. This type of forward sandwich assay may be a simple "yes/no" assay to determine whether antigen is present or may be made quantitative by comparing the amount of immobilized labeled antibody with the amount immobilized when a standard sample containing a known quantity of antigen is used.

So called "simultaneous" and "reverse" sandwich assays may also be used. A simultaneous assay involves a single incubation step as the immobilized antibody and labeled antibody are added simultaneously to the sample. After appropriate incubation, the solid support is washed to remove residue of the sample and uncomplexed labeled antibody. The presence or amount of labeled antibody associated with the solid support is then determined as in the above conventional "forward" sandwich assay.

In a "reverse" assay, a solution of labeled antibody is added to the sample after a suitable incubation period followed by addition of immobilized unlabeled antibody. After a second incubation, the solid phase material is washed in conventional fashion to free it of the residue of the sample and unreacted labeled antibody. The determination of immobilized antibody associated with the solid support is then determined as in the "simultaneous" and "forward" assays.

5.8.2. Assay for Antibody Binding to uPAR on Whole Cells

The uPAR-targeting Ab and/or conjugate thereof is readily tested for binding to uPAR, preferably by measuring inhibition of the binding of $[^{125}I]$DFP-uPA to uPAR in a competitive ligand-binding assay or by directly labeling the Ab with $[^{125}I]$. The assay may employ whole cells that express uPAR, for example cells lines such as A2780 or HeLa. A preferred assay is conducted as follows. Cells (about $5\times10^4$/well) are plated in medium (e.g., MEM with Earle's salts/10% FBS+ antibiotics) in 24-well plates, then incubated in a humid 5% $CO_2$ atmosphere until the cells reach 70% confluence. Catalytically inactivated high molecular weight uPA (DFP-uPA) is radioiodinated using Iodo-Gen® (Pierce) to a specific activity of about 250,000 cpm/µg. The cell-containing plates are then chilled on ice and the cells are washed twice (5 minutes each) with cold PBS/0.05% Tween-80. Test Abs and/or conjugates thereof are serially diluted in cold PBS/0.1% BSA/0.01% Tween-80 and added to each well to a final volume of 0.3 mL 10 minutes prior to the addition of the $[^{125}I]$DFP-uPA. Each well then receives 9500 cpm of $[^{125}I]$ DFP-uPA at a final concentration of 0.2 nM). The plates are then incubated at 4° C. for 2 hrs, after which time the cells are washed 3× (5 minutes each) with cold PBS/0.05% Tween-80. NaOH (1N) is added to each well in 0.5 mL to lyse the cells, and the plate is incubated for 5 minutes at room temperature or until all the cells in each well are lysed as determined by microscopic examination. The contents of each well are then aspirated and the total counts in each well determined using a gamma counter. Each compound is tested in triplicate and the results are expressed as a percentage of the total radioactivity measured in wells containing $[^{125}I]$DFP-uPA alone, which is taken to represent maximum (100%) binding.

The inhibition of binding of $[^{125}I]$DFP-uPA to uPAR is usually dose-related, such that the concentration of the test compound necessary to produce a 50% inhibition of binding (the $IC_{50}$ value), which is expected to fall in the linear part of the curve, is easily determined. In general, Abs and/or conjugates thereof have $IC_{50}$ values of less than about $10^{-5}$ M. Preferably, Abs and/or conjugates thereof have $IC_{50}$ values of less than about $10^{-6}$ M, more preferably, less than about $10^{-7}$M.

5.8.3. Assays of Biological Activity of Anti-uPAR Antibodies or Other Ligands

Those of skill in the art will appreciate that the in vitro and in vivo assays useful for measuring the activity of the Abs or other uPAR-binding ligands of the invention or of conjugates thereof, as described herein, are intended to be illustrative and neither comprehensive nor limiting.

5.8.3.1. Assay for EC Migration

For EC migration studies, transwells are coated with type I collagen (50 µg/mL) by adding 200 µL of the collagen solution per transwell, then incubating overnight at 37° C. The transwells are assembled in a 24-well plate and a chemoattractant (e.g., FGF-2) is added to the bottom chamber in a total volume of 0.8 mL media. ECs, such as human umbilical vein endothelial cells (HUVEC), which have been detached from monolayer culture using trypsin, are diluted to a final concentration of about $10^6$ cells/mL with serum-free media and 0.2 mL of this cell suspension is added to the upper chamber of each transwell. Inhibitors to be tested may be added to both the upper and lower chambers and the migration is allowed to proceed for 5 hrs in a humidified atmosphere at 37° C. The transwells are removed from the plate stained using Dif-fQuik®. Cells which did not migrate are removed from the upper chamber by scraping with a cotton swab and the membranes are detached, mounted on slides, and counted under a high-power field (400×) to determine the number of cells migrated.

5.8.3.2. Biological Assay of Anti-Invasive Activity

The ability of cells such as ECs or tumor cells (e.g., PC-3 human prostatic carcinoma cells) to invade through a reconstituted basement membrane (Matrigel®) in an assay known as a Matrigel® invasion assay system is well known (Kleinman et al., *Biochemistry* 1986, 25: 312-318; Parish et al., 1992, *Int. J. Cancer* 52:378-383). Matrigel® is a reconstituted basement membrane containing type IV collagen, laminin, heparan sulfate proteoglycans such as perlecan (which bind to and localize bFGF), vitronectin as well as transforming growth factor-β (TGFβ), urokinase-type plasminogen activator (uPA), tissue plasminogen activator (tPA) and the serpin known as plasminogen activator inhibitor type 1 (PAI-1) (Chambers et al., *Canc. Res.* 1995, 55:1578-1585). It is accepted in the art that results obtained in this type of assay for Abs and/or conjugates thereof or other ligands which target extracellular receptors or enzymes are predictive of the efficacy of these Abs and/or conjugates thereof in vivo (Rabbani et al., *Int. J. Cancer* 1995, 63: 840-845).

Such assays employ transwell tissue culture inserts. Invasive cells are defined as cells which traverse through the Matrigel® and upper aspect of a polycarbonate membrane and adhere to the bottom of the membrane. Transwells (e.g., from Costar) containing polycarbonate membranes (8.0 µm pore size) are coated with Matrigel® (e.g., from Collaborative Research), which has been diluted in sterile PBS to a final concentration of about 75 µg/mL (e.g., 60 µL of diluted Matrigel® per insert), and placed in the wells of a 24-well plate. The membranes are dried overnight in a biological safety cabinet, then rehydrated by adding 100 µL of medium, e.g., DMEM, supplemented with antibiotics for 1 hour on a shaker table. The DMEM is removed from each insert by aspiration and 0.8 mL of complete DMEM (+/10% FBS and antibiotics) is added to each well of the 24-well plate such that it surrounds the outside of the transwell ("lower chamber"). Fresh DMEM with antibiotics (100 µL), human Glu-plasminogen (5 µg/mL), and any inhibitors to be tested are added to the top, inside of the transwell ("upper chamber"). The cells which are to be tested are trypsinized and resuspended in DMEM+ antibiotics and added to the top chamber of the transwell at a final concentration of about $8 \times 10^5$ cells/mL. The final volume of the upper chamber is adjusted to 200 µL. The assembled plate is then incubated in a humid 5% $CO_2$ atmosphere for about 72 hours. After incubation, the cells are fixed and stained using DiffQuik® (Giemsa stain) and the upper chamber is then scraped using a cotton swab to remove the Matrigel® and any cells which did not invade through the membrane. The membranes are detached from the transwell using an X-Acto® blade, mounted on slides using Permount® and coverslips, then counted under a microscope using high power (e.g., 400x). A mean number of invading cells from 5-10 counted fields is calculated and plotted as a function of inhibitor concentration.

5.8.3.3. Tube-Formation Assays of Anti-Angiogenic Activity

ECs, for example, human umbilical vein endothelial cells (HUVEC) or human microvascular endothelial cells (HMVEC) which can be prepared or obtained commercially, are mixed at a concentration of $2 \times 10^5$ cells/mL with fibrinogen (5 mg/mL in phosphate buffered saline (PBS) in a 1:1 (v/v) ratio. Thrombin is added (5 units/mL final concentration) and the mixture is immediately transferred to a 24-well plate (0.5 mL per well). The fibrin gel is allowed to form and then VEGF and bFGF are added to the wells (each at 5 ng/mL final concentration) along with the test compound. The cells are incubated at 37° C. in 5% $CO_2$ for 4 days at which time the cells in each well are counted and classified as either rounded, elongated with no branches, elongated with one branch, or elongated with 2 or more branches. Results are expressed as the average of 5 different wells for each concentration of compound. Typically, in the presence of angiogenic inhibitors, cells remain either rounded or form undifferentiated tubes (e.g. 0 or 1 branch). This assay is recognized in the art to be predictive of angiogenic (or anti-angiogenic) efficacy in vivo (Min et al., *Cancer Res.* 1996, 56: 2428-2433).

In an alternate assay, EC tube formation is observed when ECs are cultured on Matrigel® (Schnaper H W et al., *J. Cell. Physiol.* 1995, 165:107-118). $10^4$ EC/well are transferred onto Matrigel®-coated 24-well plates, and tube formation is quantitated after 48 hrs. Inhibitors are tested by adding them either at the time of adding the ECs or at various time points thereafter. Tube formation can also be stimulated by adding (a) an angiogenic growth factor such as bFGF or VEGF, (b) a differentiation stimulating agent (e.g., PMA) or (c) a combination of these.

While not wishing to be bound by theory, this assay models angiogenesis by presenting to the ECs a particular type of basement membrane, namely the layer of matrix which migrating and differentiating ECs would be expected to encounter first. In addition to bound growth factors, the matrix components found in Matrigel® (and in basement membranes in situ), or proteolytic products thereof, may also be stimulatory for EC tube formation which makes this model complementary to the fibrin gel angiogenesis model previously described (Blood, C H et al., *Biochim. Biophys. Acta* 1990, 1032:89-118; Odedra, R et al., *Pharmac. Ther.* 1991, 49:111-124).

5.8.3.4. Assays for Inhibition of Cell Proliferation

The ability of the Abs and/or conjugates of this invention to inhibit the proliferation of ECs may be determined in a 96-well format. Type I collagen (gelatin) is used to coat the wells of the plate (0.1-1 mg/mL in PBS, 0.1 mL per well for 30 minutes at room temperature). After washing the plate (3x using PBS), $3-6 \times 10^3$ cells are plated per well and allowed to attach for 4 hrs (37° C./5% $CO_2$) in Endothelial Growth Medium (EGM; Clonetics) or M199 medium supplemented with 0.1-2% FBS. The medium and any unattached cells are removed at the end of 4 hrs and fresh medium supplemented with bFGF (1-10 ng/mL) or VEGF (1-10 ng/mL) is added to each well. Antibodies and/or conjugates to be tested are added last, and the plate is allowed to incubate (37° C./5% $CO_2$) for 24-48 hrs. The chromogenic compound MTS (Promega) is added to each well and allowed to incubate from 1-4 hrs. The color developing in each well is directly proportional to the cell number, thereby serving as a surrogate for counting cells. Absorbance read at 490 nm is used to determine the differences in cell numbers, i.e., proliferation, between control wells and those containing test Abs and/or conjugates.

A similar assay employing cultured adherent tumor cells may also be used. However, collagen may be omitted in this format. Tumor cells (e.g., $3-10 \times 10^3$/well) are plated and allowed to adhere overnight. Serum-free medium is then added, and the cells forced to synchronize for 24 hrs. Medium+10% FBS is then added to each well to stimulate proliferation. Antibodies and/or conjugates to be tested are included in some of the wells. After 24 hrs, MTS is added to the plate and the assay developed and read as above.

5.8.3.5. Assays of Cytotoxicity

The anti-proliferative and cytotoxic effects of Abs and/or conjugates thereof may be determined for various cell types including tumor cells, ECs, fibroblasts and macrophages. This is especially useful when testing a Ab which has been conjugated to a therapeutic moiety such as a radiotherapeutic or a toxin. For example, a conjugate of one of the Abs of the invention with Bolton-Hunter reagent which has been iodinated with $^{131}I$ would be expected to inhibit the proliferation of cells expressing uPAR (most likely by inducing apoptosis). Anti-proliferative effects would be expected against tumor cells and stimulated endothelial cells but, under some circumstances not quiescent endothelial cells or normal human dermal fibroblasts. Any anti-proliferative or cytotoxic effects observed in the normal cells may represent non-specific toxicity of the conjugate.

A typical assay would involve plating cells at a density of 5-10,000 cells per well in a 96-well plate. The compound to be tested is added at a concentration 10x the $IC_{50}$ measured in a binding assay (this will vary depending on the conjugate) and allowed to incubate with the cells for 30 minutes. The cells are washed 3x with media, then fresh media containing [$^3$H]thymidine (1 µCi/mL) is added to the cells and they are allowed to incubate at 37° C. in 5% $CO_2$ for 24 and 48 hours. Cells are lysed at the various time points using 1 M NaOH and counts per well determined using a β-counter. Proliferation may be measured non-radioactively using MTS reagent or CyQuant® to measure total cell number. For cytotoxicity assays (measuring cell lysis), a Promega 96-well cytotoxicity kit is used. If there is evidence of anti-proliferative activity, induction of apoptosis may be measured using TumorTACS (Genzyme).

5.8.3.6. Assay of Caspase-3 Activity

The ability of the Abs and/or conjugates to promote apoptosis of EC's may be determined by measuring activation of caspase-3. Type I collagen (gelatin) is used to coat a P100 plate and $5 \times 10^5$ ECs are seeded in EGM+10% FBS. After 24 hours (at 37° C./5% $CO_2$) the medium is replaced by EGM+2% FBS, 10 ng/ml bFGF and the desired test compound. The cells are harvested after 6 hrs, cell lysates prepared in 1% Triton X-100 detergent, and the lysates assayed using the EnzChek® Caspase-3 Assay Kit #1 (Molecular Probes) according to the manufacturer's instructions.

5.8.3.7. Xenograft Models of Subcutaneous Tumor Growth

Human Ovarian Carcinoma

A2780 human ovarian cancer line was established from tumor tissue from an untreated patient. The A2780 cells are maintained as a monolayer in RPMI 1640 medium supplemented with 2 mM glutamine, 0.01 mg/mL bovine insulin, and 10% FBS. (Hamilton, T C et al., *Sem. Oncol.* 1984; 11:285-293; Behrens, B C et al., *Cancer Res.* 1987; 47:414-418). Two million A2780 are inoculated in the right flank of nude Balb/c female mice. The A2780 tumor is staged to 50 to 200 $mm^3$ range before treatment is. The IgG control Ab as well as the anti-D2D3 uPAR mAbs are administered by the intraperitoneal route at 10 mg/kg twice weekly on Monday and Friday. The cisplatin treatment group was staged to 1000 $mm^3$; animals received 6 mg/kg once a week. Tumor volumes were measured twice a week. At the time of sacrifice, plasma is obtained and the tumor excised from each animal. Half of the tumor is snap frozen for biochemical assessment and the rest is placed in Zinc fixative for histological assessment.

Human Lung Carcinoma

A549, human lung carcinoma (ATCC Catalog No. CCL-185) cell line, was established through explant culture of lung carcinomatous tissue from a 58-year-old Caucasian male (Giard, D J et al., *J. Natl. Cancer Inst.* 51:1417-23 (1973)). A549 cells are maintained in Ham's F12K medium supplemented with 2 mM L-glutamine, 0.15% $NaHCO_3$, and 10% FBS.

About $10^6$ A549 carcinoma cells are inoculated in the right flank of C.B-17/Sys (scid/scid) Severe Combined Immunodeficient (SCID) female mice. Treatment is preferably initiated the day after tumor inoculation. The IgG control Ab (and the PBS control) as well as the anti-D2D3 uPAR mAb ATN-658 are administered intraperitoneally 10 mg/kg twice weekly on Monday and Friday. Initially tumor volumes are measured once a week. When the volume in any treatment group exceeds 300 $mm^3$, measurements are obtained twice a week.

At the time of sacrifice, plasma is obtained and the tumor excised from each animal. Half of the tumor is snap frozen for biochemical assessment and the rest is placed in Zinc fixative for histological assessment.

5.8.3.8. Xenograft Model of Metastasis

The Abs and/or conjugates are tested for inhibition of late metastasis using an experimental metastasis model such as that of Crowley et al., *Proc. Natl. Acad. Sci. USA* 1993, 90 5021-5025). Late metastasis involves the steps wherein tumor cells attach and extravasate, invade locally, seed, proliferate and induce angiogenesis. Human prostatic carcinoma cells (PC-3) transfected with a reporter gene, preferably the green fluorescent protein (GFP) gene, but as an alternative with a gene encoding the enzymes chloramphenicol acetyl-transferase (CAT), luciferase or LacZ, are inoculated into nude mice. This approach permits utilization of either of these markers (fluorescence detection of GFP or histochemical colorimetric detection of the various enzymes) to follow the fate of these cells. Cells are injected, preferably iv, and metastases identified after about 14 days, particularly in the lungs but also in regional lymph nodes, femurs and brain. This mimics the organ tropism of naturally occurring metastases in human prostate cancer. For example, GFP-expressing PC-3 cells ($10^6$ cells per mouse) are injected iv into the tail veins of nude (nu/nu) mice. Animals are treated with a test composition at 100 μg/animal/day given q.d. IP. Single metastatic cells and foci are visualized and quantitated by fluorescence microscopy or light microscopic histochemistry or by grinding the tissue and quantitative calorimetric assay of the detectable label.

5.9. Kits

The invention provides a pharmaceutical pack or kit comprising one or more containers filled with a uPAR antibody of the invention. Additionally, one or more other prophylactic or therapeutic agents useful for the treatment of a cancer can also be included in the pharmaceutical pack or kit. The invention also provides a pharmaceutical pack or kit comprising one or more containers filled with one or more of the ingredients of the pharmaceutical compositions of the invention. Optionally associated with such container(s) can be a notice in the form prescribed by a governmental agency regulating the manufacture, use or sale of pharmaceuticals or biological products, which notice reflects approval by the agency of manufacture, use or sale for human administration.

The present invention provides kits that can be used in the above methods. In one embodiment, a kit comprises one or more uPAR antibodies of the invention. In another embodiment, a kit further comprises one or more other prophylactic or therapeutic agents useful for the treatment of cancer, in one or more containers. In certain embodiments, the other prophylactic or therapeutic agent is a chemotherapeutic. In other embodiments, the prophylactic or therapeutic agent is a biological or hormonal therapeutic.

5.10. General Methods

General methods of molecular biology have been amply described in the art (Sambrook, et al., Molecular Cloning: A Laboratory Manual, 2nd (or later) Edition, Cold Spring Harbor Press, Cold Spring Harbor, N.Y., 1989; Ausubel, F et al., Current Protocols in Molecular Biology, Vol. 2, Wiley-Interscience, New York, (current edition); Kriegler, Gene Transfer and Expression: A Laboratory Manual (1990); Glover, D M, ed., DNA Cloning: A Practical Approach, vol. I & II, IRL Press, 1985; Alberts, B. et al., Molecular Biology of the Cell, 4th (or later) Ed., Garland Publishing, Inc., New York, N.Y. (2002); Watson, J D et al., Recombinant DNA, 2nd Ed. (or later) Ed., WH Freeman & Co.; 2nd edition (1993); and Old, R W et al., Principles of Gene Manipulation: An Introduction to Genetic Engineering, 5th (or later) ed., Univ. of Calif. Press, Berkeley (1994).

In the description, reference is made to various methodologies known to those of skill in the art of immunology, cell biology, and molecular biology. Publications and other materials setting forth such known methodologies to which reference is made are incorporated herein by reference in their entireties as though set forth in full. Standard reference works setting forth the general principles of immunology include Abbas, A K et al., Cellular and Molecular Immunology (Fourth Ed.), W. B. Saunders Co., Philadelphia, 2000; Janeway, C A et al., Immunobiology. The Immune System in Health and Disease, 4th ed., Garland Publishing Co., New York, 1999; Roitt, I et al., Immunology, (current ed.) C. V. Mosby Co., St. Louis, Mo. (1999); Klein, J, Immunology, Blackwell Scientific Publications, Inc., Cambridge, Mass., (1990).

Unless otherwise indicated, a particular nucleic acid sequence is intended to encompasses conservative substitution variants thereof (e.g., degenerate codon substitutions) and a complementary sequence. The term "nucleic acid" is synonymous with "polynucleotide" and is intended to include a gene, a cDNA molecule, an mRNA molecule, as well as a fragment of any of these such as an oligonucleotide, and further, equivalents thereof (explained more fully below). Sizes of nucleic acids are stated either as kilobases (kb) or base pairs (bp). These are estimates derived from agarose or polyacrylamide gel electrophoresis (PAGE), from nucleic acid sequences which are determined by the user or published. Protein size is stated as molecular mass in kilodaltons (kDa) or as length (number of amino acid residues). Protein size is estimated from PAGE, from sequencing, from presumptive amino acid sequences based on the coding nucleic acid sequence or from published amino acid sequences.

Specifically, DNA molecules encoding the amino acid sequence corresponding to the polypeptides of the present invention, or active variants thereof, can be synthesized by the polymerase chain reaction (PCR) (see, for example, U.S. Pat. No. 4,683,202) using primers derived the sequence of the protein disclosed herein. These cDNA sequences can then be assembled into a eukaryotic or prokaryotic expression vector and the resulting vector can be used to direct the synthesis of the fusion polypeptide or its fragment or derivative by appropriate host cells, for example COS or CHO cells.

The nucleic acid sequences of this invention can be DNA or RNA.

Prokaryotic or eukaryotic host cells transformed or transfected to express the present polypeptides are within the scope of the invention. For example, the polypeptide may be expressed in bacterial cells such as *E. coli*, insect cells (baculovirus), yeast, or mammalian cells such as Chinese hamster ovary cells (CHO) or human cells (which are preferred for human therapeutic use of the transfected cells). Other suitable host are known to those skilled in the art. Expression in eukaryotic cells leads to partial or complete glycosylation and/or formation of relevant inter- or intra-chain disulfide bonds of the recombinant polypeptide. Examples of vectors for expression in yeast *S. cerevisiae* include pYepSec (Baldari et al., 1987, *EMBO J.* 6: 229-234), pMFa (Kurjan et al. 1982 *Cell* 30: 933-943), pJRY88 (Schultz et al., 1987, *Gene* 54: 113-123), and pYES2 (Invitrogen Corporation, San Diego, Calif.). Baculovirus vectors available for expression of proteins in cultured insect cells (SF 9 cells) include the pAc series (Smith et al., 1983, *Mol. Cell Biol.* 3:2156-2165) and the pVL series (Lucklow et al., (1989) *Virology* 170:31-39). Generally, COS cells (Gluzman 1981 *Cell* 23:175-182) are used in conjunction with such vectors as pCDM 8 (Aruffo et al., supra, for transient amplification/expression in mammalian cells, while CHO (dhfr-negative CHO) cells are used with vectors such as pMT2PC (Kaufman et al., 1987, *EMBO J.* 6: 187-195) for stable amplification/expression in mammalian cells. The NSO myeloma cell line (a glutamine synthetase expression system.) is available from Celltech Ltd.

Construction of suitable vectors containing the desired coding and control sequences employs standard ligation and restriction techniques which are well understood in the art. Isolated plasmids, DNA sequences, or synthesized oligonucleotides are cleaved, tailored, and re-ligated in the form desired. The DNA sequences which form the vectors are available from a number of sources.

Backbone vectors and control systems are generally found on available "host" vectors which are used for the bulk of the sequences in construction. For the pertinent coding sequence, initial construction may be, and usually is, a matter of retrieving the appropriate sequences from cDNA or genomic DNA libraries. However, once the sequence is disclosed it is possible to synthesize the entire gene sequence in vitro starting from the individual nucleotide derivatives. The entire gene sequence for genes of length in the range of 500-1000 bp may be prepared by synthesizing individual overlapping complementary oligonucleotides and filling in single stranded non-overlapping portions using DNA polymerase in the presence of the deoxyribonucleotide triphosphates. This approach has been used successfully in the construction of several genes of known sequence. See, for example, Edge, *Nature* 1981, 292: 756; Nambair et al., *Science* 1984, 223:1299; and Jay, *J. Biol. Chem.* 1984, 259:6311. Synthetic oligonucleotides are prepared by methods described in references cited above or by Beaucage et al., *Tetrahedron Lett.* 1981, 22:1859; and Matteucci et al., *J. Am. Chem. Soc.* 1981, 103:3185.

The components of the desired vectors can be excised and ligated using standard restriction and ligation procedures. Site-specific DNA cleavage is performed by treating with the suitable restriction enzyme (or enzymes) under conditions which are generally understood in the art, and the particulars of which are specified by the manufacturer of these commercially available restriction enzymes. See, e.g., New England Biolabs, Product Catalog. If desired, size separation of the cleaved fragments may be performed by standard polyacrylamide gel or agarose gel electrophoresis techniques (e.g., Meth. Enzymol. (1980) 65:499-560).

Any of a number of methods are used to introduce mutations into the coding sequence to generate variants if these are to be produced recombinantly. These mutations include simple deletions or insertions, systematic deletions, insertions or substitutions of clusters of bases or substitutions of single bases. Modification of the DNA sequence by site-directed mutagenesis is a well-known technique for which protocols and reagents are commercially available (Zoller et al., Nucleic Acids Res. 1982, 10:6487-6500; Adelman et al., DNA 1983, 2:183-193)). The isolated DNA is analyzed by restriction and/or sequenced by the dideoxy nucleotide method (Sanger, *Proc. Natl. Acad. Sci. USA* 1977, 74:5463; Messing, et al., *Nucleic Acids Res.* 1981, 9:3091 or Maxam et al., *Meth. Enzymol.*, supra).

Vector DNA can be introduced into mammalian cells via conventional techniques such as calcium phosphate or calcium chloride co-precipitation, DEAE-dextran-mediated transfection, lipofection, or electroporation. Suitable methods for transforming host cells can be found in Sambrook et al. supra and other standard texts. In fusion expression vectors, a proteolytic cleavage site is introduced at the junction of the reporter group and the target protein to enable separation of the target protein from the reporter group subsequent to purification of the fusion protein. Proteolytic enzymes for such cleavage and their recognition sequences include Factor Xa, thrombin and enterokinase.

Having now generally described the invention, the same will be more readily understood through reference to the following examples which are provided by way of illustration, and are not intended to be limiting of the present invention, unless specified.

6. EXAMPLES

6.1. Materials and Methods

6.1.1. Cell Lines Expressing Proteins

The *Drosophila* expression system (DES™; Invitrogen, Inc.) utilizes the Schneider 2 (S2) cell line, derived from *Drosophila melanogaster*, and plasmid vectors for the expression of heterologous proteins. The plasmid vectors for expression in S2 cells are very versatile, allowing inducible expression of a protein driven by the metallothionein (MT) promoter. The same plasmid also allows the protein to be secreted from the cell into the surrounding media, greatly simplifying protein purification. Multiple copies of the vector can be stably inserted into the genomic DNA of S2 cells, increasing levels of protein expression. Proteins expressed in S2 cells are minimally glycosylated, which is important for the generation of Abs directed against the protein component of uPAR. Typical yields of protein following purification are 25-50 mg/L with a purity of approximately 95 percent. Cell lines expressing the following proteins have been generated: suPAR, D1, D2D3, scuPA, ATF1-143, ATF1-135, Kringle47-143, and Kringle47-135. In addition, clones have been generated for suPAR in which the N-linked glycosylation sites have been abolished.

6.1.2. Reagents $^{125}$I was purchased as Na$^{125}$I (480-630 MBq [13-17 mCi] per μg iodine) from the Amersham Corp.

6.1.3. Tumor Cell Lines

The following cell and tumor lines were used: A549, HeLa, and A2780. The A2780 human ovarian cancer line was established from tumor tissue from an untreated patient. A2780 cells are maintained as a monolayer in RPMI 1640 medium supplemented with 2 mM glutamine, 0.01 mg/mL bovine insulin, and 10% FBS (supra). A549, human lung carcinoma, ATCC Catalog No. CCL-185, described above, are maintained in Ham's F12K medium supplemented with 2 mM L-glutamine, 0.15% NaHCO$_3$, and 10% FBS.

A2780 cells (2×10$^6$) were inoculated in the right flank of nude Balb/c female mice. The tumor was staged to 50 to 200 mm$^3$ range before treatment was initiated. The IgG control antibody as well as the anti-D2D3 uPAR mAbs were administered intraperitoneally at 10 mg/kg twice weekly on Monday and Friday. The cisplatin treatment group was staged to 1000 mm$^3$; animals received 6 mg/kg once a week. Tumor volumes were measured twice a week.

A549 carcinoma cells (10$^6$) were inoculated in the right flank of C.B-17/Sys (scid/scid) female mice (scid: Severe Combined Immunodeficient). Treatment was started the day after tumor inoculation. The IgG control Ab (and the PBS control) as well as the anti-D2D3 uPAR mAb ATN-658 were administered intraperitoneally 10 mg/kg twice weekly on Monday and Friday. Initially tumor volumes were measured once a week. When the volume in any treatment group exceeded 300 mm$^3$, measurements were obtained twice a week.

At the time of sacrifice, plasma is obtained and the tumor excised from each animal. Half of the tumor is snap frozen for biochemical assessment and the rest is placed in Zinc fixative for histological assessment.

6.2. Binding of uPA to uPAR

Binding of uPA to uPAR was measured using $^{125}$I-labeled uPA and HeLa cells (see FIG. 2). HeLa cells express abundant amounts of uPAR but do not express uPA. Briefly, 100 μg of scuPA was labeled with 100 μCi of [$^{125}$I]NaI using Iodo-Gen™ iodination reagent (Pierce Biotechnology Inc.). Unincorporated labeled NaI was removed from the labeled protein using a size exclusion column and the labeled protein eluted in Tris-buffered saline containing 0.1% bovine serum albumin (BSA). HeLa cells were incubated with increasing concentrations of [$^{125}$I]-scuPA diluted in PBS containing 0.1% BSA for 2 h at 4° C. Cells were washed extensively with PBS/0.1% BSA, the cell monolayers lysed with 1M NaOH and the total number of bound counts determined. Specific binding was determined by incubating cells with [$^{125}$I]-scuPA in the presence of a large excess of unlabeled scuPA. Binding was also performed with MDA-MB231 cells which express both uPA and uPAR. To determine binding of scuPA, endogenous uPA is first removed from the surface of MDA-MB231 cells by washing with a buffer containing 0.1 M glycine/100 mM NaCl, pH 3 for 5 minutes at 4° C. This protocol was also used to determine binding of [$^{125}$I]-ATF to HeLa cells. The ability of Abs to inhibit the binding of either [$^{125}$I]-scuPA or [$^{125}$I]-ATF binding to HeLa cells was determined by incubating cells with increasing amounts of the unlabeled Ab for 15 minutes at 4° C., prior to the addition of the [$^{125}$I]-labeled protein.

ATN-658 does not inhibit the binding of scuPA to uPAR (FIG. 2) on the surface of HeLa cells and is able to bind to HeLa cells in the presence of scuPA. Thus, ATN-658 can target both occupied and unoccupied receptors on the cell surface.

Binding of scuPA to uPAR also was measured using biotinylated scuPA and HeLa cells. Briefly, HeLa cells were plated into 24 well plate at 150,000 cells per well 24 hours prior to carrying out the binding assay. 3 ml of 30 nM biotin-ATN-615, 3 ml of 30 nM biotin-ATN-658 and 3 mL of 100 nM biotin-scuPA were prepared and serial diluted with 2 ml buffer for every 1 ml of reagent. The plated HeLa cells were washed 2 times with 1 ml wash buffer (1×HBSS/0.1% BSA) followed by incubation with biotin-scuPA, biotin-ATN-658 or biotin-ATN-615 for 1 hour at room temperature in binding buffer (1×HBSS/0.1% BSA). Unlabeled ATN-658, ATN-617, or scuPA can be added to assay for non-specific and competitive binding. The cells were then washed 2 times with 1 ml wash buffer. 250 μl Avidin-HRP (1 μl into 20 ml buffer) were added to each well and allowed to incubate for 30 minutes at room temperature, followed by 3 washes. Subsequently, OPD substrate (250 μl) was added to each well, and a yellow color was allowed to develop before the reaction was stopped with 50 μl 1M H$_2$SO$_4$ (for 24-well plate). Readings at OD 490 nm were done to analyze the color of each well of the plate.

6.3. Activities of mAbs In Vivo

Antibodies were tested for their ability to inhibit tumor growth in vivo in two models: the A549 non-small cell human lung cancer model and the A2780 ovarian cancer model using the protocols and conditions described in Section 6.1. Treatment was started the day after tumor inoculation. The IgG control Ab (and the PBS control) as well as the anti-D2D3 UPAR mAb ATN-658 was administered by the intraperitoneal route at 10 mg/kg twice weekly on Monday and Friday.

ATN-658 significantly inhibited growth in both of these models (FIGS. 3 and 4).

6.4. Identification of ATN-658 Epitopes

The ATN-658 epitope was identified by comparing human and green monkey uPAR protein sequences. ATN-658 does not bind to green monkey uPAR so it was hypothesized that the difference in sequences might be responsible for this lack of cross-reactivity. There are 9 amino acids that are different between green monkey and human uPAR in the D2D3 region (see FIG. 5A).

Each of the non-homologous green monkey residues was changed to the corresponding human residue (e.g. amino acid 125 was changed from M to V; amino acid 192 was changed from H to R etc.). All amino acid numbers refer to the mature processed form of human uPAR, i.e., after the 22 amino acid signal peptide is removed. The effects of these changes were evaluated on the ability of ATN-658 to immunoprecipitate the mutated monkey suPAR after transient expression in S2 cells. The only mutation that restored binding was when amino acid 268 was mutated from E to K (see FIG. 5B). Since mutating amino acids 262 and 264 had no effect on binding of ATN-658 to monkey uPAR, the N-terminus of the epitope was defined as amino acid 265. Alanine scanning mutagenesis of human uPAR starting at amino acid 267 identified amino acids 268 (K) through amino acid 277 (D) as being part of the epitope (see FIG. 6). See Vajdos et al., 2002, J Mol Biol. 320(2):415-28; Nisihara et al., 2001, *J Immunol.* 167(6):3266-75; and Zhang et al., 1999, *Int Immunol.* 11(12):1935-44. Mutating amino acids 268 (K), 273 (H), 275 (D), or 277 (D) to Ala in human uPAR resulted in reduced binding of ATN-658 to the mutated human uPAR as demonstrated by co-immunoprecipitation assays. Although the epitope appears to be contiguous, it may be a conformationally dependent epitope in that reduction destroys the ability of uPAR to be recognized by ATN-658. This is likely due to the fact that there is a disulfide loop within the epitope (Cys266-Cys271) that appears to stabilize the epitope. The epitope sequence is set forth below.

C C T K S G C N H P D L D V Q Y R S G    (SEQ ID NO: 9)

This sequence represents amino acids 265-283 of the mature human uPAR sequence. The epitope may stop at Q279 since amino acids 280-283 appear to be floppy and are not visible in the crystal structure.

An additional sequence encompassing amino acids 98-114 of mature uPAR was identified using deuterium exchange mass spectrometry. See Hamuro et al., 2006, *Protein Sci.* 15(8):1883-92; Baerga-Ortiz et al., 2002, *Protein Sci.* 11(6):1300-8. The epitope sequence is set forth below.

C G S S D M S C E R G R H Q S L Q    (SEQ ID NO: 14)

This method measures deuterium exchange of a protein in the presence and absence of an antibody. The binding of an antibody to an epitope on a protein decreases the ability of that epitope to exchange deuterium and a comparison of proteolytic digests from a protein that undergoes deuterium exchange in the presence or absence of antibody using mass spectrometry localizes the epitope that is bound, by detecting reduced deuterium exchange at the epitope (see FIG. 7A). Thus, deuterium exchange of suPAR D2D3 was analyzed by mass spectrometry in the presence and absence of ATN-658. FIGS. 7B and 7C present the results obtained from two independent deuterium exchange experiments. In FIGS. 7B and 7C, the level of deuteration detected at each amino acid residue of D2D3 suPAR in the presence and absence of ATN-658 is shown. The difference in the levels of deuteration detected at each amino acid residue of D2D3 suPAR in the presence and absence of ATN-658 is also shown. Two epitope sequences that had the highest degree of protection in the presence of ATN-658 were identified: a region encompassing amino acids 268-277 (SEQ ID NO: 16) (which is encompassed in the epitope identified using site directed mutagenesis) and a second region encompassing amino acids 98-114 (SEQ ID NO: 14) (see FIGS. 7B and 7C). In particular, the region encompassing acids 268-277 (SEQ ID NO: 16) possessed the highest differences in the level of deuteration in the presence and absence of ATN-658 relative to all other regions of D2D3 suPAR.

6.5. Assay for Antibodies that Recognize the Same Epitope as ATN-658 Using Biotinylated ATN-658

The anti-D2D3 antibody, ATN-658, is biotinylated using EZ-Link™ sulfo-NHS-LC-biotin (Pierce Biotechnology Inc.) according to the manufacturer's instructions. Typically, a 20-fold molar excess of the biotin-labeling reagent is used to label ATN-658 and unincorporated biotin is removed from the labeled Ab using a size exclusion column. To ensure that the labeled antibody retained its affinity for uPAR, Biotin-ATN-658 is tested in an ELISA assay for binding to suPAR. Bound Biotin-ATN-658 is detected using HRP-conjugated streptavidin. To identify antibodies that recognize the same epitope as ATN-658 a competition assay is performed. Briefly, 96-well EIA/RIA high protein binding plates are coated with 100 ng/well of suPAR overnight at 4° C. After the blocking of non-specific binding with 1% casein, plates are washed with PBS and antibodies to be tested, diluted in PBS/0.1% casein containing 0.2 nM Biotin-ATN-658, added to the appropriate wells. Plates are incubated for a further 1 hr at room-temperature, are washed extensively with PBS/0.05% Tween-20 and the bound Biotin-ATN-658 is detected using HRP-conjugated streptavidin and the appropriate substrate.

Those skilled in the art will recognize, or be able to ascertain using no more than routine experimentation, many equivalents to the specific embodiments of the invention described herein. Such equivalents are intended to be encompassed by the following claims.

All publications, patents and patent applications mentioned in this specification are herein incorporated by reference into the specification to the same extent as if each individual publication, patent or patent application was specifically and individually indicated to be incorporated herein by reference.

What is claimed is:

1. An isolated peptide consisting of the amino acid sequence CCTKSGCNHPDLDVQYRSG (SEQ ID NO:9), CCTKSGCNHPDLDVQYRS (SEQ ID NO:10), CCTKSGCNHPDLDVQYR (SEQ ID NO:11), CCTKSGCNHPDLDVQY (SEQ ID NO:12), CCTKSGCNHPDLDVQ (SEQ ID NO:13), CGSSDMSCERGRHQSL (SEQ ID NO:14) or KSGCNHPDLD (SEQ ID NO:16).

2. An isolated peptide, the sequence of which (i) consists of a fragment of human uPAR amino acid sequence (SEQ ID NO:15); and (ii) comprises the amino acid sequence CCTKS-GCNHPDLDVQYRSG (SEQ ID NO: 9), or CGSSDM-SCERGRHQSL (SEQ ID NO:14); wherein said peptide is up to 80 amino acids in length.

3. The isolated peptide of claim 2, wherein said peptide is up to 50 amino acids in length.

4. The isolated peptide of claim 2, wherein said peptide is up to 30 amino acids in length.

5. The isolated peptide of claim 2, wherein said peptide is up to 20 amino acids in length.

6. The isolated peptide of claim 1, wherein the peptide consists of the amino acid sequence CCTKSGCNHPDLD-VQYRSG (SEQ ID NO:9), CCTKSGCNHPDLDVQYRS (SEQ ID NO:10), CCTKSGCNHPDLDVQYR (SEQ ID NO:11), CCTKSGCNHPDLDVQY (SEQ ID NO:12), CCTKSGCNHPDLDVQ (SEQ ID NO:13) or CGSSDM-SCERGRHQSL (SEQ ID NO:14).

7. The isolated peptide of claim 2, the sequence of which
   (i) consists of a fragment of human uPAR amino acid sequence (SEQ ID NO:15) in which Cys 265 is the amino terminus of the peptide; and
   (ii) comprises the amino acid sequence CCTKSGCNHP-DLDVQYRS (SEQ ID NO:10), CCTKSGCNHPDLD-VQYR (SEQ ID NO:11), CCTKSGCNHPDLDVQY (SEQ ID NO:12), or CCTKSGCNHPDLDVQ (SEQ ID NO:13);
wherein said peptide is up to 80 amino acids in length.

8. The isolated peptide of claim 1, wherein the peptide consists of the amino acid sequence KSGCNHPDLD (SEQ ID NO:16).

9. The isolated peptide of claim 2, the sequence of which
   (i) consists of a fragment of human uPAR amino acid sequence (SEQ ID NO:15) in which Lys 268 is the amino terminus of the peptide; and
   (ii) comprises the amino acid sequence KSGCNHPDLD (SEQ ID NO:16);
wherein said peptide is up to 80 amino acids in length.

10. A purified fragment of human uPAR (SEQ ID NO:15), in which the amino terminus of said fragment is at anyone of amino acid positions 93-98 and the carboxy terminus of said fragment is at any one of amino acid positions 277-283,
   with the proviso that the fragment is not a fragment consisting of residues 93-277 or
   consisting of residues 93-283 of SEQ ID NO:15,
or a derivative of said purified fragment containing one or more conservative substitutions relative to the sequence of said fragment, which derivative is bound by monoclonal antibody ATN-658, as deposited with the American Type Culture Collection and assigned ATCC Accession No. PTA-8191.

11. The isolated peptide of claim 7, wherein said peptide is up to 50 amino acids in length.

12. The isolated peptide of claim 7, wherein said peptide is up to 30 amino acids in length.

13. The isolated peptide of claim 7, wherein said peptide is up to 20 amino acids in length.

14. The isolated peptide of claim 9, wherein said peptide is up to 50 amino acids in length.

15. The isolated peptide of claim 9 wherein said peptide is up to 30 amino acids in length.

16. The isolated peptide of claim 9, wherein said peptide is up to 20 amino acids in length.

17. A method of producing an antibody, which comprises:
   (i) immunizing a mammal with a peptide of claim 1;
   (ii) isolating splenocytes from said mammal;
   (iii) fusing said splenocytes to myeloma cells; and
   (iv) selecting a hybridoma that secretes an antibody that binds said peptide.

18. A method of producing an antibody, which comprises:
   (i) immunizing a mammal with a peptide comprising a conformation-dependent epitope defined by
      (a) CCTKSGCNHPDLDVQYRSG (SEQ ID NO:9), CCTKSGCNHPDLDVQYRS (SEQ ID NO:10), CCTKSGCNHPDLDVQYR (SEQ ID NO:11), CCTKSGCNHPDLDVQY (SEQ ID NO:12), CCTKSGCNHPDLDVQ (SEQ ID NO:13) or KSGC-NHPDLD (SEQ ID NO:16); and
      (b) CGSSDMSCERGRHQSL (SEQ ID NO:14) of a human uPAR (SEQ ID NO:15) wherein said peptide is up to 200 amino acids in length;
   (ii) isolating splenocytes from said mammal;
   (iii) fusing said splenocytes to myeloma cells; and
   (iv) selecting a hybridoma that secretes an antibody that binds said conformation-dependent epitope.

19. A method of producing an antibody, which comprises:
   (i) immunizing a mammal with a peptide of claim 2;
   (ii) isolating splenocytes from said mammal;
   (iii) fusing said splenocytes to myeloma cells; and
   (iv) selecting a hybridoma that secretes an antibody that binds said peptide.

20. A method of producing an antibody, which comprises:
   (i) immunizing a mammal with a peptide of claim 6;
   (ii) isolating splenocytes from said mammal;
   (iii) fusing said splenocytes to myeloma cells; and
   (iv) selecting a hybridoma that secretes an antibody that binds said peptide.

21. A method of producing an antibody, which comprises:
   (i) immunizing a mammal with the fragment or derivative of claim 6;
   (ii) isolating splenocytes from said mammal;
   (iii) fusing said splenocytes to myeloma cells; and
   (iv) selecting a hybridoma that secretes an antibody that binds said fragment.

22. A method of producing an antibody, which comprises:
   (i) immunizing a mammal with a peptide of claim 7;
   (ii) isolating splenocytes from said mammal;
   (iii) fusing said splenocytes to myeloma cells; and
   (iv) selecting a hybridoma that secretes an antibody that binds said peptide.

23. The method of claim 18, wherein the immunizing peptide comprises a conformation-dependent epitope defined by
   (a) CCTKSGCNHPDLDVQYRSG (SEQ ID NO:9), CCTKSGCNHPDLDVQYRS (SEQ ID NO:10), CCTKSGCNHPDLDVQYR (SEQ ID NO:11), CCTKSGCNHPDLDVQY (SEQ ID NO:12) or CCTKSGCNHPDLDVQ (SEQ ID NO:13); and
   (b) CGSSDMSCERGRHQSL (SEQ ID NO:14) of a human uPAR (SEQ ID NO:15), wherein said peptide is up to 200 amino acids in length.

\* \* \* \* \*